(12) United States Patent
Martin et al.

(10) Patent No.: US 9,574,202 B2
(45) Date of Patent: Feb. 21, 2017

(54) METHODS FOR INCREASING THE ANTHOCYANIN CONTENT OF CITRUS FRUIT

(71) Applicant: Norfolk Plant Sciences, Ltd., Norwich (GB)

(72) Inventors: Catherine Martin, Norwich (GB); Eugenio Butelli, Norwich (GB)

(73) Assignee: Norfolk Plant Sciences, Ltd., Norwich (GB)

(*) Notice: Subject to any disclaimer, the term of this patent is extended or adjusted under 35 U.S.C. 154(b) by 382 days.

(21) Appl. No.: 13/749,774

(22) Filed: Jan. 25, 2013

(65) Prior Publication Data

US 2014/0007287 A1 Jan. 2, 2014

Related U.S. Application Data

(60) Provisional application No. 61/591,115, filed on Jan. 26, 2012.

(51) Int. Cl.
*C12N 15/82* (2006.01)

(52) U.S. Cl.
CPC ......... *C12N 15/8243* (2013.01); *C12N 15/825* (2013.01)

(58) Field of Classification Search
CPC .................................................. C12N 15/8243
See application file for complete search history.

(56) References Cited

PUBLICATIONS

Guo et al (2004), Proc. Natl. Acad. Sci. USA vol. 101 pp. 9205-9210.*
Ngo et al. in The Protein Folding Problem and Tertiary Structure Prediction, 1994, Merz et al. (ed.), Birkhauser, Boston, MA, pp. 491-495.*
Guo et al, 2004, Proc. Natl. Acad. Sci. USA vol. 101 pp. 9205-9210.*
Barbagallo et al, Enzyme and Microbial Technology (2007) vol. 41 pp. 570-575.*
Lin-Wang et al, BMC Plant Biology (2010) 10: 50 pp. 1-17.*
Tripoli et al, Food Chemistry (2007) 104: 466-479.*
Rose et al Nucleic Acids Research (1998) 26:1628-1635.*
Alquézar et al, Journal of Experimental Botany (2009) 60: 1783-1797.*
Ahrazem et al, Journal of Experimental Botany (2010) 61: 105-119.*
Hoff (2009) BMC Genomics 10: 1-9.*
Butelli, E., et al., "Enrichment of tomato fruit with health-promoting anthocyanins by expression of select transcription factors," *Nature Biotechnology*, Nov. 26, 2008, pp. 1301-1308, vol. 26(11), Nature Publishing Group.
Butelli, E., et al., "Retrotransposons Control Fruit-Specific, Cold-Dependent Accumulation of Anthocyanins in Blood Oranges," *The Plant Cell*, Mar. 1, 2012, pp. 1242-1255, vol. 24(3), American Society of Plant Biologists.
Cultrone, A., et al., "Cloning and molecular characterization of R2R3-MYB and bHLH-MYC transcription factors from *Citrus sinensis*," Tree Genetics& Genomes, Sep. 17, 2009, pp. 101-112, vol. 6(1), Springer, Berlin, Germany (DE).
Heim, M., et al., "The Basic Helix-Loop-Helix Transcription Factor Family in Plants: A Genome-Wide Study of Protein Structure and Functional Diversity," *Molecular Biology and Evolution*, May 1, 2003, pp. 735-747, vol. 20(5), The University of Chicago Press, US.
Li, H. et al., "Maize Lc transcription factor enhances biosynthesis of anthocyanins, distinct proanthocyanidins and phenylpropanoids in apple (*Malus domestica* Borkh.)," *Planta*, Jul. 6, 2007, pp. 1243-1254, vol. 226(5), Springer, Berlin, Germany (DE).
Lo Piero, et al., "Anthocyanins Accumulation and Related Gene Expression in Red Orange Fruit Induced by Low Temperature Storage," *Journal of Agricultural and Food Chemistry*, Nov. 1, 2005, pp. 9083-9088, vol. 53(23), American Chemical Society.

* cited by examiner

*Primary Examiner* — Russell Kallis
(74) *Attorney, Agent, or Firm* — Williams Mullen, PC; David M. Saravitz

(57) ABSTRACT

Methods are provided for making a citrus plant that is capable of producing fruit with increased levels of anthocyanins in the fruit when compared to a citrus fruit from a wild-type or control plant. Such methods involve increasing the expression of Ruby, an R2R3 Myb transcription factor, in a citrus plant, particularly in the fruit of a citrus plant. Further provided are citrus plants, citrus fruit, and citrus plant cells made by such methods, nucleic acid molecules and expression cassettes comprising nucleotide sequences that encode Ruby, and the Ruby proteins encoded thereby.

18 Claims, 10 Drawing Sheets

METHODS FOR INCREASING THE ANTHOCYANIN CONTENT OF CITRUS FRUIT

CROSS-REFERENCE TO RELATED APPLICATION

This application claims the benefit of U.S. Provisional Patent Application No. 61/591,115, filed Jan. 26, 2012, herein incorporated by reference in its entirety.

REFERENCE TO A SEQUENCE LISTING SUBMITTED AS A TEXT FILE VIA EFS WEB

The official copy of the sequence listing is submitted electronically via EFS-Web as an ASCII formatted sequence listing with a file named 429212SeqLst.txt, created on Jan. 24, 2013, and having a size of 68.4 kilobytes, and is filed concurrently with the specification. The sequence listing contained in this ASCII formatted document is part of the specification and is herein incorporated by reference in its entirety.

FIELD OF THE INVENTION

This invention relates to the field of plant molecular biology, particularly the improvement of plants through the use of genetic engineering methods.

BACKGROUND OF THE INVENTION

In addition to their striking color, blood oranges are believed to have significant health-promoting properties, combining the high content of vitamin C, carotenoids and fiber of common blond oranges with the health-promoting properties of anthocyanin pigments (de Pascual-Theresa et al., 2010; Paradez-Lopez et al., 2010; Davies, 2007; Prior and Wu, 2006). The high anthocyanin content of blood oranges underpins their high antioxidant activity (Proteggente et al., 2011; Kelebek et al., 2008; Jayaprakasha and Patl, 2007; Rapisada et al., 1999). Consumption of blood orange juice has been shown to reduce oxidative stress in diabetic patients (Bottina et al., 2002), protect DNA against oxidative damage (Guarnieri et al., 2007; Riso et al., 2005) and may reduce cardiovascular risk factors more generally, as demonstrated for other high-anthocyanin foods (de Pascual-Theresa et al., 2010; Paradez-Lopez et al., 2010; Toufektsian et al., 2008). Recently, blood orange juice has been shown to limit the development of adipocytes and weight gain in mice and to confer resistance to obesity compared to blond orange juice or water (Titta et al., 2010). In a mouse model of obesity, blood orange juice consumption rescued almost completely the transcriptional reprogramming induced by a high fat diet.

Despite increasing consumer interest in their high nutritional quality, blood oranges do not have a global market, largely due to a lack of dependability of color development. All blood orange varieties require strong day-night thermal clines for intense color formation in fruit flesh, and varieties such as Moro, with the potential for high pigmentation, are strongly dependent on the prevailing climatic conditions during fruit ripening for full colour development. Post-harvest storage of fruit in the cold enhances pigmentation, but this is an expensive measure to ensure high levels of pigmentation, and can increase post-harvest losses (Crifò et al., 2011; Latado et al., 2008; Rapisada et al., 1999). The dependency of anthocyanin accumulation on environment means that the most reliable blood orange production, on a commercial scale, is limited to Italy, specifically to the Sicilian area around Mount Etna (Zarba and Pulvirenti, 2006) where it remains highly seasonal. Although blood oranges are grown in other countries, in some years entire harvests are lost due to non-optimal conditions during ripening of fruit, and when they are cultivated in Brazil or Florida (the largest producers of oranges worldwide), coloration is generally weak or absent and unreliable (Latado et al., 2008; Hodgson, 1967). To ensure a stable supply of blood oranges, improved oranges trees which can produce blood oranges with reliably high levels of anthocyanins under a variety of environmental conditions, are desired.

Anthocyanins are natural pigments found typically in red, purple and blue fruit and flowers (Winkel-Shirley, 2001). Many varieties of blood orange have been derived from old Italian varieties such as Doppio Sanguigno and include more recently-derived varieties such as Tarocco and Moro, which generally have higher levels of anthocyanin pigmentation of their fruit (FIG. 1). The history of these varieties is debated although authoritative texts suggest three independent derivations: one Italian/Sicilian from Doppio Sanguigno/Maltaise Sanguine, a second in Spain from Doblefina and a third from Shamouti Orange referred to as Shamouti Blood or Palestinian Blood Jaffa Orange (Hodgson, 1967). In the mid-19th century it was believed that blood oranges arose by bud mutation in the Mediterranean region following the introduction of sweet orange in the $16^{th}$ century (Holmes, 1924). More recently it was suggested that blood oranges originated much earlier in Asia (Hodgson, 1967; Chapot, 1963). The blood orange was first documented in Italy in 'Hesperides' by Ferrari (1646), a Jesuit scholar who wrote of an orange with purple-colored flesh that tasted strangely like a grape (Ferrari, 1646). Ferrari suggested that the blood orange was brought to Sicily by a Genoese missionary after a long journey which started in China. However, claims of Chinese poems referring to scarlet/red oranges, dating from the Tang period to more recent times, are probably based on mistranslation of the term 'orange' and likely refer to mandarins which never accumulate anthocyanins. Some definitively red oranges are portrayed in a picture by Bartolomeo Bimbi, a Florentine artist who painted the Medici Citrus collections early in the $18^{th}$ century.

BRIEF SUMMARY OF THE INVENTION

Methods are provided for making a citrus plant that is capable of producing fruit with increased levels of anthocyanins in the fruit when compared to a citrus fruit from a wild-type or other control plant. The methods of the present invention involve increasing the expression of Ruby in a citrus plant, particularly in the fruit of a citrus plant. Ruby is a novel R2R3 Myb transcription factor that regulates the expression of genes required for anthocyanin biosynthesis in citrus fruit as disclosed hereinbelow. In one embodiment, the methods comprise introducing into at least one citrus plant cell a polynucleotide construct comprising a promoter operably linked to nucleotide sequence encoding Ruby. Preferably, the promoter is capable of driving the expression of the nucleotide sequence encoding Ruby in a citrus fruit or part thereof, particularly the carpels or endocarp. The methods of the invention can further comprise regenerating a citrus plant comprising the polynucleotide construct.

In another embodiment, the methods comprise introducing into at least one citrus plant cell a polynucleotide construct comprising a promoter that is capable of driving the expression of an operably linked nucleotide sequence. In this embodiment, the citrus plant cell comprises stably incorporated in its genome a native or non-native nucleotide sequence encoding a functional Ruby protein. Such a method further comprises the use of homologous recombination methods that are known in the art to incorporate the introduced polynucleotide construct comprising a promoter in operable linkage with the nucleotide sequence encoding a functional Ruby protein, whereby the promoter is capable of driving the expression of the nucleotide sequence encoding a functional Ruby protein. Preferably, the promoter is capable of driving the expression of the nucleotide sequence encoding Ruby in a citrus fruit or part thereof, particularly the carpels or endocarp. The methods of the invention can further comprise regenerating a citrus plant comprising the polynucleotide construct.

Isolated nucleic acid molecules comprising the Ruby nucleotide sequences disclosed herein and fragments and variants thereof that encode functional Ruby proteins are further provided as wells as the Ruby proteins encoded thereby. Also provided are nucleic acid molecules comprising the retrotransposons, Tcs1 and Tcs2. Expression cassettes comprising a promoter operably linked to a nucleotide sequence encoding a Ruby protein are additional provided.

Additionally provided are citrus plants and citrus plant cell made by the methods disclosed herein as well as citrus fruit produced from such plants and food products derived from the citrus fruit including, for example, citrus fruit juice, beverages comprising citrus fruit juice (e.g., sodas, smoothies and other blended beverages). marmalades, and food colorants.

S=Sanguinelli; MS=Maltaise Sanguine; J=Jingxian; O=Oroval. The presence of DNA containing only the solo LTR (band 2) as well as DNA containing the full Tcs1 retroelement (band 1) is apparent in Sanguinelli and Maltaise Sanguine accessions.

Figure 6:
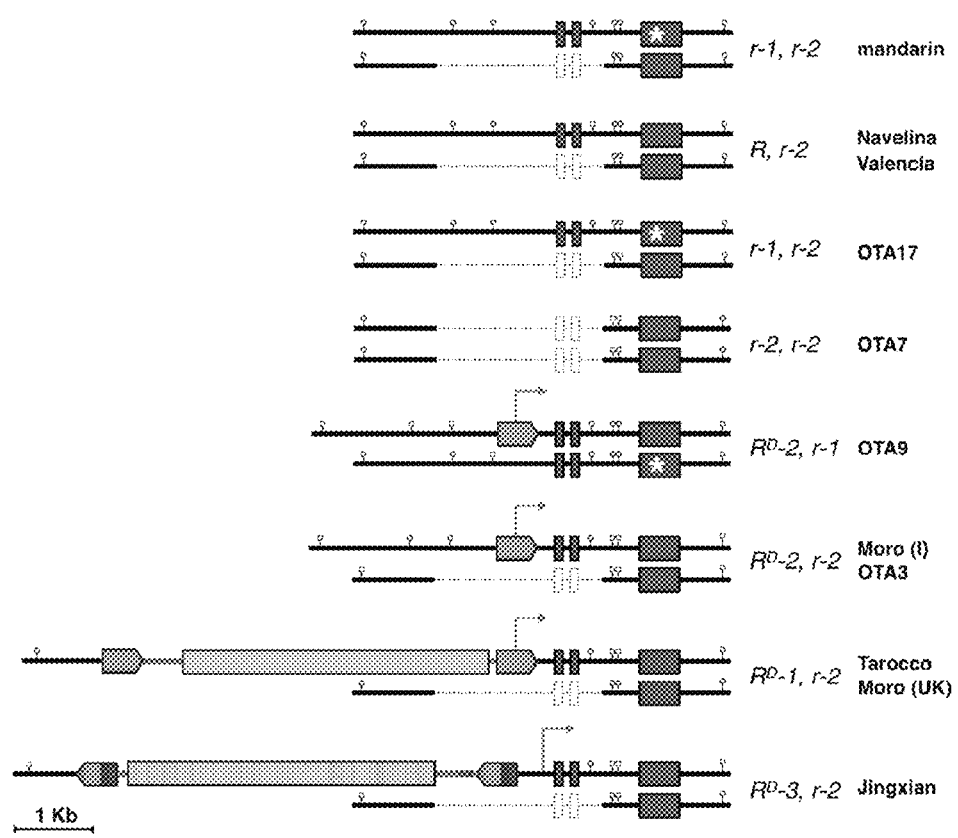

FIG. 6. Maps of structures of the Ruby locus in the different orange accessions and hybrids. Green thick arrows, retrotransposon LTRs; grey thick bars, open reading frame encoding functional Gag-Pol polyprotein; purple thick bars, open reading frame encoding the Ruby protein; thin bars, non-coding regions. The asterisk indicates a stop codon. The differences in sequence between Tcs1 and Tcs2 are indicated by blue lines on the map of Tcs2. The start of transcription of the Ruby mRNA is shown by a grey arrow for each accession. The AseI sites (AseI does not cut in either Tcs1 or Tcs2) in the Ruby locus are shown as vertical line with a circle attached to the upper end. Moro (I) indicates the accession of Moro from CRA, Sicily, and Moro (UK) indicates the accession of Moro from Reeds, UK.

Figure 7:
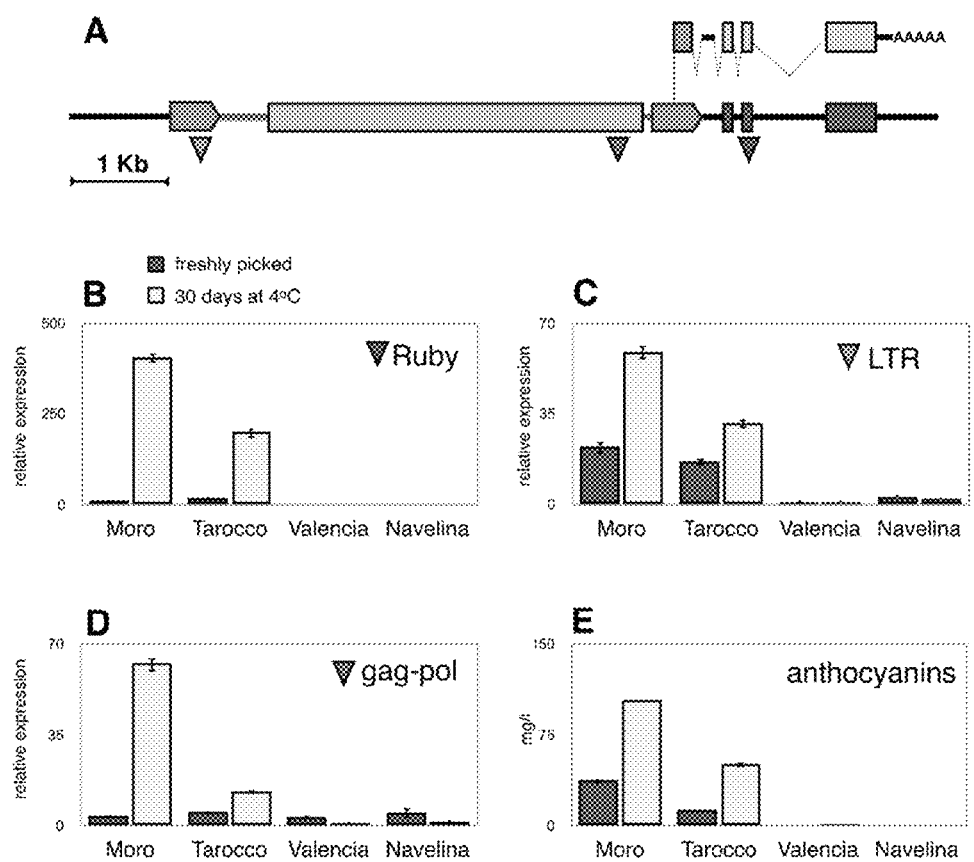

FIG. 7. Expression of Tcs1, Ruby and anthocyanin production in blood and blond oranges in response to cold storage. (A) Detailed map of the Ruby locus with the full Tcs1 retroelement insertion, showing the start of transcription of the Ruby gene. The map of the Ruby transcript is shown above; the thick green bars indicating sequence from the LTR in the 5'UTR, the thick purple bars indicating the open reading frame encoding the Ruby protein, also indicated by thick pink bars in the transcript; the splice sites for the transcript are shown. The positions of the oligonucleotides used for measuring transcript levels of Ruby and Tcs1 are also indicated by colour-coded inverted triangles. (B) Levels of Ruby transcripts in Moro and Tarocco blood orange accessions and in Valencia and Navelina blond orange accessions from CRA in fruit picked fresh and following storage for 30 days at 4° C., determined by qRT-PCR. (C) Levels of Tcs1 transcripts from the LTR in Moro and Tarocco blood orange accessions and in Valencia and Navelina blond orange accessions from CRA in fruit picked fresh and following storage for 30 days at 4° C., determined by qRT-PCR. (D) Levels of Tcs1 and Tcs2 transcripts from the Gag-Pol region of the element in Moro and Tarocco blood orange accessions and in Valencia and Navelina blond orange accessions from CRA in fruit picked fresh and following storage for 30 days at 4° C., determined by qRT-PCR. (E) Levels of anthocyanins in Moro and Tarocco blood orange accessions and in Valencia and Navelina blond orange accessions from CRA in fruit picked fresh and following storage for 30 days at 4° C.

Figure 8:
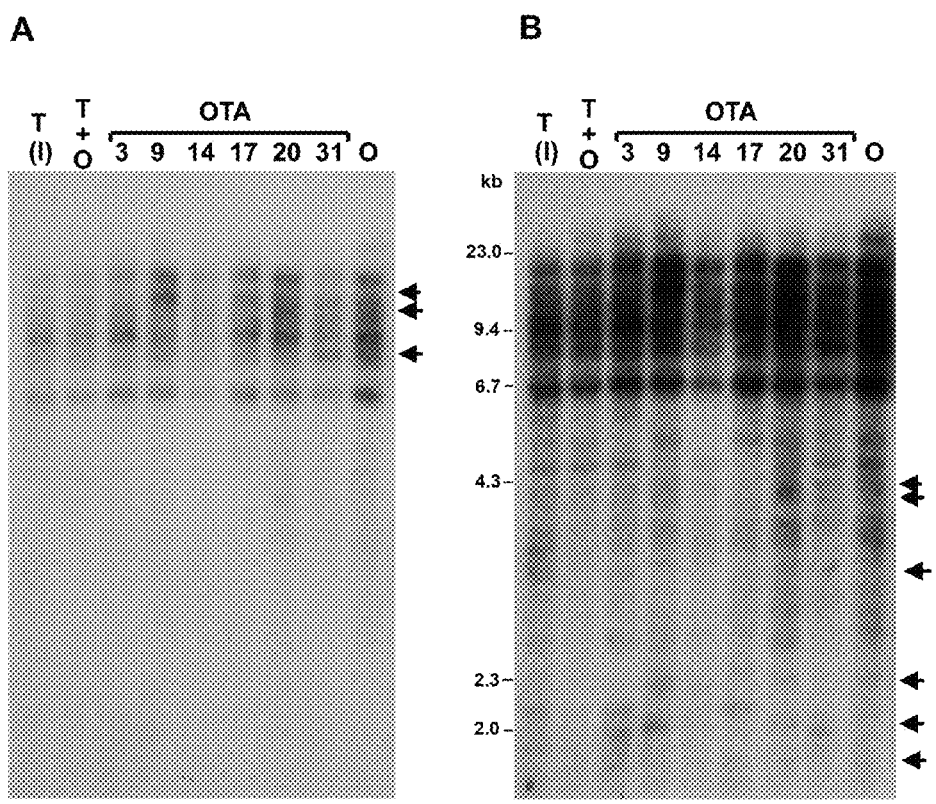

FIG. 8. Southern blots of genomic DNA from Tarocco and Oroval (mandarin) parents and the OTA hybrids. Genomic DNA was digested with AseI and probed with a $^{32}$P-labelled probe of the Tcs1 LTR. AseI does not cut within Tcs1; therefore, fragments larger than 5.4 kb likely represent full length retroelement insertions. (A) Short exposure shows large, strongly hybridising bands (two copies of the LTR). New bands present in the hybrids but not in the parents are arrowed and likely represent new transpositions. (B) Long exposure shows smaller, more weakly hybridizing bands. New bands present in the hybrids but not in the parents are arrowed and likely represent unequal crossing over events between the LTRs to leave solo LTR insertions. T (I)=Tarocco (CRA); O=Oroval; T+O=equimolar mixture of Tarocco and Oroval DNA.

Figure 9:
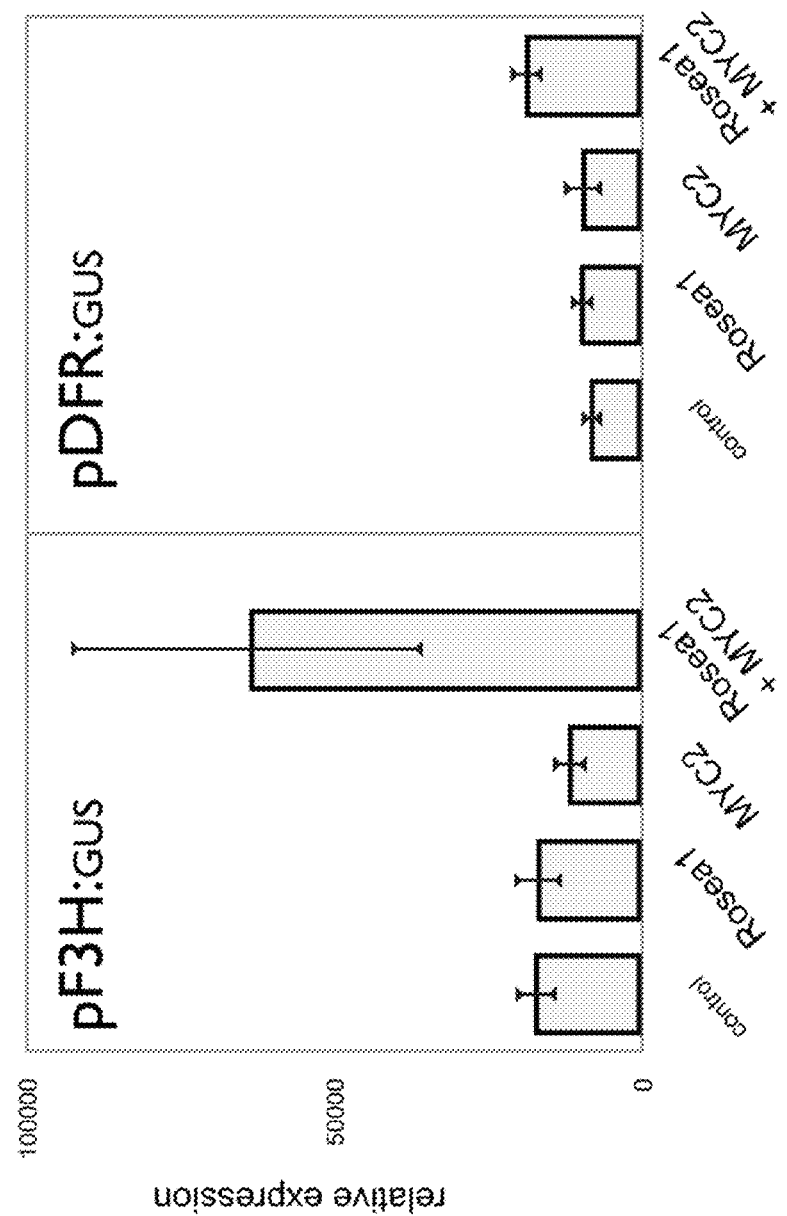

FIG. 9. CsMYC2 regulates anthocyanin biosynthetic gene expression. MYB transcription factors interact with bHLH and WDR proteins in a complex known as the MBW complex. The WDR partner is generally constitutively expressed (Walker et al., 1999) but activity of the bHLH partner can limit anthocyanin production (Hellens et al., 2010; Bradley et al., 1999; Lauter et al., 2004). Transfection assays in tobacco protoplasts using reporter genes driven by the F3H and DFR promoters from *Antirrhinum majus* were used to assay the ability of different transcription factors to activate the expression of anthocyanin biosynthetic genes. No activation of either promoter was observed with CsMYC2 on its own. The MYB gene Rosea1 activated expression of both promoters slightly on its own. The combination of CsMYC2 with Rosea1 significantly enhanced expression from both the F3H and DFR promoters, showing that CsMYC2 can interact in the MBW complex to activate anthocyanin biosynthesis. Control lanes show GUS activity from protoplasts transfected with the reporter construct alone without added regulatory genes. Data are presented as means (±SD) of three biological replicates.

Figure 10:
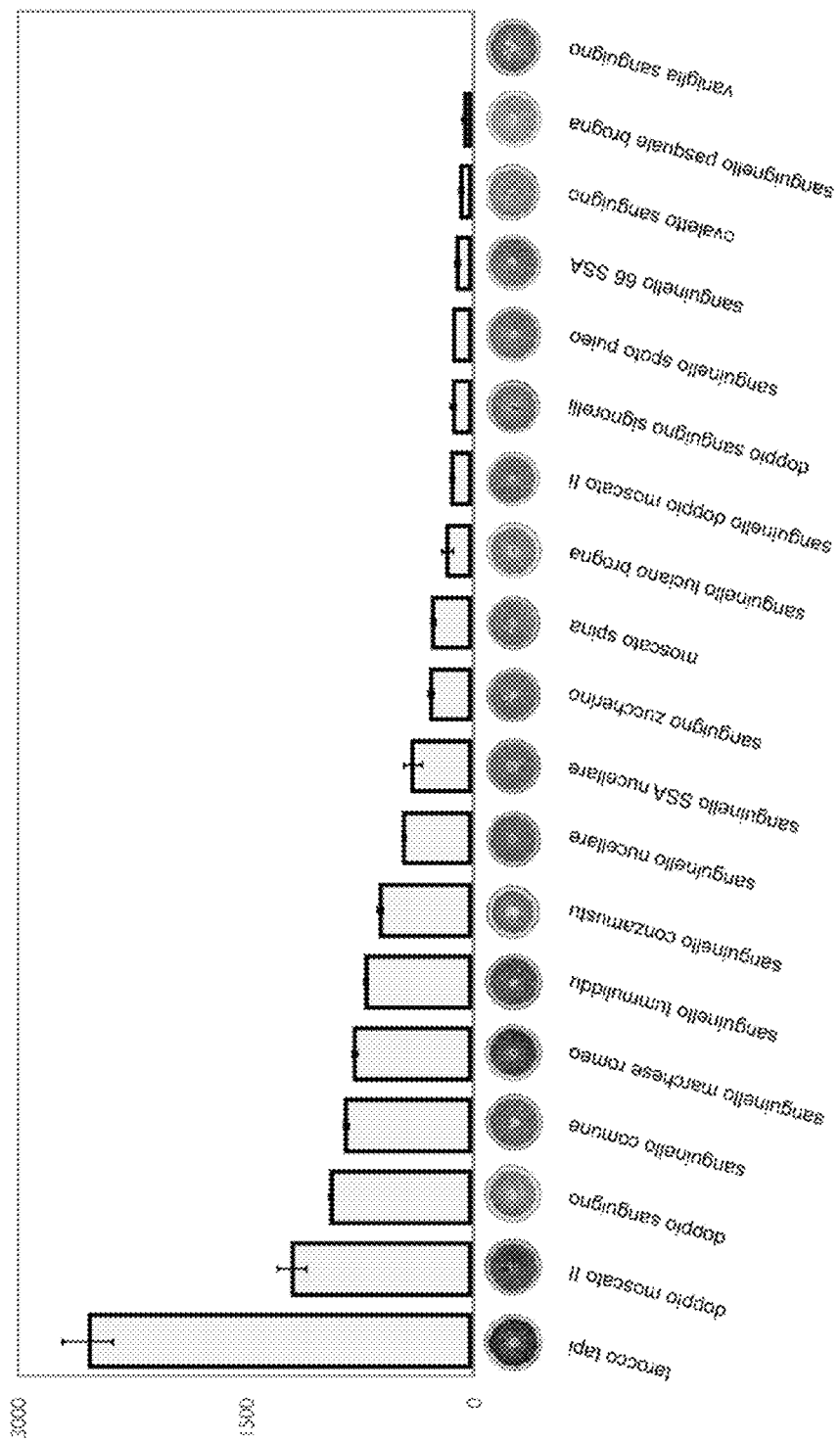

FIG. 10. Expression analysis of Ruby. Expression analysis of Ruby in varieties of the 'Sanguigni,' and 'Sanguinelli' blood orange groups. Red pigmentation in the last sample, Vaniglia Sanguigno, is due to the carotenoid lycopene, not anthocyanins.

SEQUENCE LISTING

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus. The coding sequences of the present invention as used herein do not include the stop codon unless indicated otherwise or apparent from the context. It is understood that a stop codon can be added at the end of any coding sequence for the termination of transcription. Such stop codons include, for example, TAG, TAA, and TGA.

SEQ ID NO: 1 sets forth a nucleotide sequence of the wild-type allele of the Ruby gene from *Citrus sinensis* cv. Navel. The coding sequence comprises nucleotides 681-798, 896-1025, and 1821-2358.

SEQ ID NO: 2 sets forth the amino acid sequence of the wild-type Ruby protein of *Citrus sinensis* cv. Navel, which is encoded by wild-type allele of the Ruby gene set forth in SEQ ID NO: 1.

SEQ ID NO: 3 sets forth a nucleotide sequence of a dominant allele of the Ruby gene from *Citrus sinensis* cv. Moro. The coding sequence comprises nucleotides 1180-1297, 1395-1524, and 2320-2857.

SEQ ID NO: 4 sets forth the amino acid sequence of the Ruby protein of *Citrus sinensis* cv. Moro, which is encoded by the dominant allele of the Ruby gene set forth in SEQ ID NO: 3.

SEQ ID NO: 5 sets forth a nucleotide sequence of a deletion allele of the Ruby gene from *Citrus sinensis*×*Citrus reticulata* cv. OTA7. The coding sequence comprises nucleotides 836-874.

SEQ ID NO: 6 sets forth the amino acid sequence of the Ruby protein of *Citrus sinensis×Citrus reticulata* cv. OTA7, which is encoded by the deletion allele of the Ruby gene set forth in SEQ ID NO: 5.

SEQ ID NO: 7 sets forth a nucleotide sequence of the Tcs1 retrotransposon of *Citrus sinensis* cv. Tarocco. The coding sequence comprises nucleotides 911-4837.

SEQ ID NO: 8 sets forth the amino acid sequence of the polyprotein encoded by the Tcs1 retrotransposon set forth in SEQ ID NO: 7.

SEQ ID NO: 9 sets forth a nucleotide sequence of the Tcs2 retrotransposon of *Citrus sinensis* cv. Jingxian. The coding sequence comprises nucleotides 964-4890.

SEQ ID NO: 10 sets forth the amino acid sequence of the polyprotein encoded by the Tcs2 retrotransposon set forth in SEQ ID NO: 9.

SEQ ID NO: 11 sets forth a nucleotide sequence of a full-length Ruby mRNA of *Citrus sinensis* cv. Moro. The coding sequence comprises nucleotides 324-1109.

SEQ ID NO: 12 sets forth the amino acid sequence encoded by the full-length Ruby mRNA comprising the nucleotide sequence set forth in SEQ ID NO: 11.

SEQ ID NO: 13 sets forth a nucleotide sequence of a Ruby mRNA of *Citrus sinensis* cv. Jingxian. The coding sequence comprises nucleotides 130-915.

SEQ ID NO: 14 sets forth the amino acid sequence encoded by the Ruby mRNA comprising the nucleotide sequence set forth in SEQ ID NO: 13.

SEQ ID NO: 15 sets forth a nucleotide sequence a promoter derived the β-LCY2 gene of *Citrus sinensis*.

SEQ ID NO: 16 sets forth a nucleotide sequence of *Citrus sinensis* capsanthin/capsorubin synthase (CCS) gene of GenBank Accession No. AF169241. The coding sequence comprises nucleotides 1722-3230.

SEQ ID NO: 17 sets forth the amino acid sequence of the capsanthin/capsorubin synthase (CCS) encoded by the nucleotide sequence set forth in SEQ ID NO: 16.

SEQ ID NOS: 18-42 are the oligonucleotide primers that are described in Table 1 below.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The present invention is based on the isolation of the Ruby gene from blood oranges (*Citrus sinensis*) and the discovery that this gene encodes a novel R2R3 Myb transcription factor that regulates the expression of genes required for anthocyanin biosynthesis in citrus fruit as disclosed in the Example below. It was further discovered that the fruit-specific and cold-dependent accumulation of anthocyanins in blood oranges is the result of retrotransposons that regulate the expression of the Ruby gene in a fruit-specific and cold-dependent manner thereby resulting in the production of the Ruby protein which in turn regulates the expression of genes required for anthocyanin biosynthesis in citrus fruit. Although blond oranges (*Citrus sinesis*) contain an allele of Ruby that encodes an apparently functional protein, the expression of the Ruby was not detected in blond orange fruit as described below in the Example.

The present invention provides methods for making a citrus plant that is capable of producing fruit with increased levels of anthocyanins in the fruit when compared to a citrus fruit from a wild-type or other control plant. Such methods find use in making citrus trees that are capable of producing fruit with high levels of anthocyanins, whereby anthocyanin production is not cold-dependent as it is for wild-type blood oranges. Such methods find use in the stable production of blood oranges, particularly in the stable production of blood oranges in citrus-growing regions of the world where cold temperatures do not occur or do not reliably occur during fruit development and maturation. Moreover, the methods of the present invention are applicable to other citrus besides oranges. For example, the methods disclosed herein can used to increase the anthocyanin content of the widely consumed, lycopene-rich red grapefruit that is produced from grapefruit varieties such as, for example, 'Ruby Red', 'Henderson', 'Ray', 'Rio Red', and 'Star Ruby'. Thus, the methods disclosed herein find use in making grapefruit that are rich in not only the carotenoid lycopene but also anthocyanins. Such grapefruits, and juices and other food products make therefrom are expected to be highly desirable for human consumption to the presence the high levels of the antioxidants, lycopene and anthocyanins.

The methods of the present invention comprise increasing the expression of Ruby in a citrus plant, particularly in the fruit of a citrus plant. In one embodiment, the methods comprise introducing into at least one citrus plant cell a polynucleotide construct comprising a promoter operably linked to nucleotide sequence encoding Ruby. Preferably, the promoter is capable of driving the expression of the nucleotide sequence encoding Ruby in a citrus fruit or part thereof, particularly the carpels or endocarp. The methods of the invention can further comprise regenerating a citrus plant comprising the polynucleotide construct.

In another embodiment, the methods comprise introducing into at least one citrus plant cell a polynucleotide construct comprising a promoter that is capable of driving the expression of an operably linked nucleotide sequence. In this embodiment, the citrus plant cell comprises stably incorporated in its genome a native or non-native nucleotide sequence encoding a functional Ruby protein. Such a method further comprises the use of homologous recombination methods that are known in the art to incorporate the introduced polynucleotide construct comprising a promoter in operable linkage with the nucleotide sequence encoding a functional Ruby protein, whereby the promoter is capable of driving the expression of the nucleotide sequence encoding a functional Ruby protein. Preferably, the promoter is capable of driving the expression of the nucleotide sequence encoding Ruby in a citrus fruit or part thereof, particularly the carpels or endocarp. The methods of the invention can further comprise regenerating a citrus plant comprising the polynucleotide construct.

Additional embodiments of the invention are described hereinbelow. Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Embodiments of the invention include, but are not limited to:

1. A method for making a plant that is capable of producing a fruit with an increased level of anthocyanins, said method comprising modifying a plant so was to increase the expression of Ruby in the fruit of the plant, wherein a fruit produced by the plant comprises an increased level of anthocyanins when compared to a control fruit.
2. The method of embodiment 1, wherein modifying the plant comprises introducing into at least one cell of the plant a polynucleotide construct comprising a promoter operably linked to a nucleotide sequence encoding Ruby.
3. The method of embodiment 1 or 2, wherein the nucleotide sequence encoding Ruby comprises a nucleotide sequence selected from the group consisting of:
   (a) the coding sequence set forth in Sequence SEQ ID NO: 1, 3, 11, or 13;
   (b) a nucleotide sequence encoding the amino acid sequence set forth in SEQ ID NO: 2, 4, 12, or 14;
   (c) a nucleotide sequence comprising at least 75% identity to at least one of the full-length coding sequences set forth in SEQ ID NOS: 1, 3, 11, and 13, wherein the nucleotide sequence encodes a polypeptide comprising Ruby transcription factor activity;
   (d) a nucleotide sequence encoding an amino acid sequence comprising at least 75% identity to at least one of the full-length amino acid sequences set forth in SEQ ID NOS: 2, 4, 12, and 14; wherein the nucleotide sequence encodes a polypeptide comprising Ruby transcription factor activity;
   (e) a fragment of any one of (a)-(d), wherein the fragment encodes a polypeptide comprising Ruby transcription factor activity; and
   (f) the nucleotide sequence of any one of (a)-(e), wherein the polypeptide further comprises at least one of the motifs, $DLX_2RX_3LX_6LX_3R$ (SEQ ID NO: 49) and $KPXPR(S/T)F$ (SEQ ID NO: 50).
4. The method of embodiment 2 or 3, wherein the promoter preferentially drives gene expression in a fruit.
5. The method of any one of embodiments 2-4, wherein the promoter comprises the nucleotide sequence set forth in SEQ ID NO: 15.
6. The method of any one of embodiments 1-5, wherein the plant is a citrus plant.
7. The method of embodiment 6, wherein the citrus plant is selected from the group consisting of sweet orange, sour orange, grapefruit, pummelo, citron, lime, mandarin, clementine, and lemon.
8. The method of embodiment 6, wherein the citrus plant is a sweet orange.
9. The method of embodiment 8, wherein the sweet orange is a blond orange.
10. The method of embodiment 8, wherein the sweet orange is a blood orange.
11. The method of any one of embodiments 4-10, wherein the promoter drives expression in the carpels of the fruit.
12. The method of any one of embodiments 1-11, further comprising regenerating a plant comprising the polynucleotide construct.
13. The method of embodiment 12, further comprising growing the plant so as to produce at least one fruit.
14. The method of embodiment 13, wherein the fruit produced by the plant comprises an increased level of anthocyanins when compared to a control fruit.
15. The method of any one of embodiments 2-14, wherein the polynucleotide construct is stably incorporated into the genome of the plant.
16. The method of embodiment 1, wherein modifying the plant comprises introducing into at least cell of the plant a polynucleotide construct comprising a promoter that is capable of driving the expression of an operably linked nucleotide sequence in the plant, whereby the polynucleotide construct integrates into the genome of the plant cell in operable linkage with a nucleotide sequence encoding a functional Ruby protein that is present in the genome of plant.
17. The method of embodiment 16, wherein the nucleotide sequence encoding a functional Ruby protein is native to the genome of the plant.
18. The method of embodiment 16 or 17, wherein the nucleotide sequence encoding a functional Ruby protein is heterologous to the genome of the plant.
19. The method of any one of embodiments 16-18, wherein the promoter preferentially drives gene expression in a fruit.
20. The method of any one of embodiments 16-19, wherein the promoter comprises the nucleotide sequence set forth in SEQ ID NO: 15.
21. The method of any one of embodiments 16-20, wherein the plant is a citrus plant.
22. The method of embodiment 21, wherein the citrus plant is selected from the group consisting of sweet orange, sour orange, grapefruit, pummelo, citron, lime, mandarin, clementine, and lemon.
23. The method of embodiment 21, wherein the citrus plant is a sweet orange.
24. The method of embodiment 23, wherein the sweet orange is a blond orange.
25. The method of embodiment 23, wherein the sweet orange is a blood orange.
26. The method of any one of embodiments 19-25, wherein the promoter drives expression in the carpels of the fruit.
27. The method of any one of embodiments 16-26, further comprising regenerating a plant comprising the polynucleotide construct.
28. The method of embodiment 27, further comprising growing the plant so as to produce at least one fruit.
29. The method of embodiment 30, wherein the fruit produced by the plant comprises an increased level of anthocyanins when compared to a control fruit.
30. The method of embodiment 16, wherein the polynucleotide construct is stably incorporated into the genome of the plant.
31. A plant produced by the method of any one of embodiments 1-30.
32. A scion or other part or cell of the plant of embodiment 31.
33. A fruit produced by the plant of embodiment 31.

34. A juice or food product produced from the fruit of embodiment 33.

35. A transformed plant or plant cell comprising stably incorporated in its genome a polynucleotide construct, said polynucleotide construct comprising a promoter operably linked to a nucleotide sequence, wherein said nucleotide sequence comprises a member selected from the group consisting of:
  (a) the coding sequence set forth in SEQ ID NO: 1, 3, 11, or 13;
  (b) a nucleotide sequence encoding the amino acid sequence set forth in SEQ ID NO: 2, 4, 12, or 14;
  (c) a nucleotide sequence comprising at least 75% identity to at least one of the full-length coding sequences set forth in SEQ ID NOS: 1, 3, 11, and 13, wherein the nucleotide sequence encodes a polypeptide comprising Ruby transcription factor activity;
  (d) a nucleotide sequence encoding an amino acid sequence comprising at least 75% identity to at least one of the full-length amino acid sequences set forth in SEQ ID NOS: 2, 4, 12, and 14; wherein the nucleotide sequence encodes a polypeptide comprising Ruby transcription factor activity;
  (e) a fragment of any one of (a)-(d), wherein the fragment encodes a polypeptide comprising Ruby transcription factor activity;
  (f) the nucleotide sequence of any one of (a)-(e), wherein the polypeptide further comprises at least one of the motifs, $DLX_2RX_3LX_6LX_3R$ (SEQ ID NO: 49) and KPXPR(S/T)F (SEQ ID NO: 50); and
  (g) a nucleotide sequence that is fully complementary to any one of (a)-(f).

36. The plant or plant cell of embodiment 35, wherein the plant is a citrus plant.

37. The plant or plant cell of embodiment 36, wherein the citrus plant is selected from the group consisting of sweet orange, sour orange, grapefruit, pummelo, citron, lime, mandarin, clementine, and lemon.

38. The plant or plant cell of embodiment 36, wherein the citrus plant is a sweet orange.

39. The plant or plant cell of embodiment 38, wherein the sweet orange is a blond orange.

40. The plant or plant cell of embodiment 38, wherein the sweet orange is a blood orange.

41. The plant or plant cell of any one of embodiments 35-40, wherein the promoter preferentially drives gene expression in a fruit.

42. The plant or plant cell of any one of embodiments 35-40, wherein the promoter comprises the nucleotide sequence set forth in SEQ ID NO: 15.

43. The plant or plant cell of embodiment 41 or 42, wherein the promoter drives expression in the carpels of the fruit.

44. The plant of any one of embodiments 36-43, wherein a fruit produced by the plant comprises an increased level of anthocyanins when compared to a control fruit.

45. The plant cell of any one of embodiments 36-43, wherein the plant cell is a fruit cell.

46. A fruit produced by the citrus plant of any one or embodiments 36-44.

47. A transformed plant or plant cell comprising stably incorporated in its genome a polynucleotide construct, said polynucleotide construct comprising a promoter, wherein the polynucleotide construct is in operable linkage with a nucleotide sequence encoding a functional Ruby protein that is present in the genome of plant.

48. The transformed plant or plant cell of embodiment 47, wherein Ruby expression is increased in the plant or at least one part thereof relative to a control plant.

49. The transformed plant or plant cell of embodiment 47 or 48, wherein the nucleotide sequence encoding a functional Ruby protein is native to the genome of the plant.

50. The transformed plant or plant cell of embodiment 47 or 48, wherein the nucleotide sequence encoding a functional Ruby protein is heterologous to the genome of the plant.

51. The plant or plant cell of any one of embodiments 47-50, wherein the plant is a citrus plant.

52. The plant or plant cell of embodiment 51, wherein the citrus plant is selected from the group consisting of sweet orange, sour orange, grapefruit, pummelo, citron, lime, mandarin, clementine, and lemon.

53. The plant or plant cell of embodiment 51, wherein the citrus plant is a sweet orange.

54. The plant or plant cell of embodiment 53, wherein the sweet orange is a blond orange.

55. The plant or plant cell of embodiment 53, wherein the sweet orange is a blood orange.

56. The plant or plant cell of any one of embodiments 47-55, wherein the promoter preferentially drives gene expression in a fruit.

57. The plant or plant cell of any one of embodiments 47-56, wherein the promoter comprises the nucleotide sequence set forth in SEQ ID NO: 15.

58. The plant or plant cell of embodiment 56 or 57, wherein the promoter drives expression in the carpels of the fruit.

59. The plant of any one of embodiments 47-58, wherein a fruit produced by the plant comprises an increased level of anthocyanins when compared to a control fruit.

60. The plant cell of any one of embodiments 47-58, wherein the plant cell is a fruit cell.

61. A fruit produced by the citrus plant of any one or embodiments 47-59.

62. An isolated nucleic acid molecule comprising a nucleotide sequence selected from the group consisting of:
  (a) the coding sequence set forth in SEQ ID NO: 1, 3, 11, or 13;
  (b) a nucleotide sequence encoding the amino acid sequence set forth in SEQ ID NO: 2, 4, 12, or 14;
  (c) a nucleotide sequence comprising at least 75% identity to at least one of the full-length coding sequences set forth in SEQ ID NOS: 1, 3, 11, and 13, wherein the nucleotide sequence encodes a polypeptide comprising Ruby transcription factor activity;
  (d) a nucleotide sequence encoding an amino acid sequence comprising at least 75% identity to at least one of the full-length amino acid sequences set forth in SEQ ID NOS: 2, 4, 12, and 14; wherein the nucleotide sequence encodes a polypeptide comprising Ruby transcription factor activity;
  (e) a fragment of any one of (a)-(d), wherein the fragment encodes a polypeptide comprising Ruby transcription factor activity;
  (f) the nucleotide sequence of any one of (a)-(e), wherein the polypeptide further comprises at least one of the motifs, $DLX_2RX_3LX_6LX_3R$ (SEQ ID NO: 49) and KPXPR(S/T)F (SEQ ID NO: 50); and
  (g) a nucleotide sequence that is fully complementary to any one of (a)-(f).

63. An expression cassette comprising a promoter operably linked to the nucleic acid molecule of embodiment 62.
64. A host cell comprising the expression cassette of embodiment 63.
65. The host cell of embodiment 64, wherein the host cell is a plant cell.
66. A plant comprising the expression cassette of embodiment 63.
67. A fruit, a fruit juice, or other food product comprising the expression cassette of embodiment 63.
68. A polypeptide comprising an amino acid sequence selected from the group consisting of:
   (a) the amino acid sequence set forth in SEQ ID NO: 2, 4, 12, or 14;
   (b) an amino acid sequence encoded by the nucleotide sequence set forth in SEQ ID NO: 1, 3, 11, or 13;
   (c) an amino acid sequence comprising at least 75% identity to at least one of the full-length amino acid sequences set forth in SEQ ID NOS: 2, 4, 12, and 14, wherein the polypeptide comprises Ruby transcription factor activity;
   (d) an amino acid sequence comprising a nucleotide sequence comprising at least 75% identity to at least one of the full-length coding sequences set forth in SEQ ID NOS: 1, 3, 11, and 13, wherein the polypeptide comprises Ruby transcription factor activity; and
   (e) a fragment of any one of (a)-(d), wherein the polypeptide comprises Ruby transcription factor activity.
69. An isolated nucleic acid molecule comprising a nucleotide sequence selected from the group consisting of:
   (a) the nucleotide sequence set forth in SEQ ID NO: 7 or 9;
   (b) the coding sequence set forth in SEQ ID NO: 7 or 9;
   (c) a nucleotide sequence encoding the amino acid sequence set forth in SEQ ID NO: 8 or 10;
   (d) a functional variant or fragment of the nucleotide sequence of (a), wherein the functional fragment or variant comprise at least 75% identity to at least one of the full-length nucleotide sequences set forth in SEQ ID NOS: 7 and 8;
   (e) a nucleotide sequence encoding a functional fragment or variant of the protein encoding by (b) or (c), wherein the functional fragment or variant comprises at least 75% identity to at least one of the full-length amino acid sequences set forth in SEQ ID NOS: 8 and 10; and
   (f) a nucleotide sequence that is fully complementary to any one of (a)-(e).
70. A plant, plant cell, or expression cassette comprising the nucleic acid of embodiment 69.
71. A polypeptide comprising an amino acid sequence selected from the group consisting of:
   (a) the amino acid sequence set forth in SEQ ID NO: 8; and
   (b) the amino acid sequence set forth in SEQ ID NO: 9.

Isolated nucleic acid molecules comprising the Ruby nucleotide sequences disclosed herein and fragments and variants thereof that encode functional Ruby proteins are further provided as wells as the Ruby proteins encoded thereby. Also provided are nucleic acid molecules comprising the retrotransposons, Tcs1 and Tcs2, set forth in SEQ ID NOS: 7 and 9, respectively, and fragments and variants thereof that encode functional retrotransposons. Such nucleic acid molecule acid molecules find use in methods of transposon tagging or for regulating gene expression in citrus in a fruit-specific, cold-dependent manner as disclosed hereinbelow. Expression cassettes comprising a promoter operably linked to a nucleotide sequence encoding a Ruby protein and plants, plant parts, plant cells and other host cells comprising a nucleotide sequence encoding a Ruby protein are also provided. Further provided are plants, plant parts, plant cells, and other host cells comprising the nucleotide sequence or Tcs1 and/or Tcs2 and fragments and variants thereof that encode functional retrotransposons.

Additionally provided are citrus plants and citrus plant cell made by the methods disclosed herein as well as citrus fruit produced from such plants and food products derived from the citrus fruit including, for example, citrus fruit juice, beverages comprising citrus fruit juice (e.g., sodas, smoothies and other blended beverages). marmalades, and food colorants.

The invention encompasses isolated or substantially purified polynucleotide (also referred to herein as "nucleic acid molecules") or protein (also referred to herein as "polypeptide") compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the native protein and hence R2R3 Myb transcription factor as disclosed herein below for Ruby. Fragments of polynucleotide comprising retrotransposon sequences retain biological activity of the native the native Tcs1 or Tcs2 retrotransposon. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

A fragment of a Ruby polynucleotide that encodes a biologically active portion of a Ruby protein of the invention will encode at least 15, 25, 30, 50, 100, 150, 200, or 250 contiguous amino acids, or up to the total number of amino acids present in a full-length Ruby protein of the invention (for example, 262 amino acids for the amino acid sequences set forth in SEQ ID NOS: 2, 4, 12, and 14). Fragments of a Ruby polynucleotide that are useful as hybridization probes or PCR primers generally need not encode a biologically active portion of a Ruby protein.

Thus, a fragment of a Ruby polynucleotide may encode a biologically active portion of a Ruby protein, or it may be a fragment that can be used as a hybridization probe or PCR primer using methods disclosed below. A biologically active portion of a Ruby protein can be prepared by isolating a portion of one of the Ruby polynucleotides of the invention, expressing the encoded portion of the Ruby protein (e.g., by recombinant expression in vitro), and assessing the activity of the encoded portion of the Ruby protein. Polynucleotides that are fragments of a Ruby nucleotide sequence comprise at least 16, 20, 50, 75, 100, 125, 150, 175, 200, 250, 300, 350, 400, 450, 500, 550, 600, 650, 700, or 750 contiguous nucleotides, or up to the number of nucleotides present in a full-length Ruby polynucleotide disclosed herein (for example, 786 nucleotides for the coding sequence set forth in SEQ ID NO: 11; the coding sequence of SEQ ID NO: 11 comprises nucleotides 324 to 1109 with the stop codon immediately thereafter at nucleotides 1110-1112).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the Ruby polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a Ruby protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the Ruby polypeptide the Ruby comprising the amino acid sequence set forth in SEQ ID NO: 2 or 4. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, that is, Ruby transcription factor activity as described in the Example hereinbelow. Such variants may result from, for example, genetic polymorphism or from human manipulation. Biologically active variants of a native Ruby protein of the invention will have at least about 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

To assess if variants and fragments of Ruby are functional or active, Ruby transcription factor activity can be assessed by determining if a variant or fragment protein can activate anthocyanin biosynthesis under the control of the constitutive CaMV 35S promoter in tobacco by the method disclosed in the Example hereinbelow.

The proteins of the invention may be altered in various ways including amino acid substitutions, deletions, truncations, and insertions. Methods for such manipulations are generally known in the art. For example, amino acid sequence variants and fragments of the proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found, Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired biological activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity of a Ruby protein be can be evaluated by the assay as described hereinbelow. Those fragments and variants of an Ruby protein will retain the ability of Ruby to activate anthocyanin biosynthesis in a plant or plant cell and thus, comprise Ruby transcription factor activity.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have promoter activity and which hybridize under stringent conditions to at least one of the polynucleotides disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire nucleic acid molecule of polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among one or more of the polynucleotide sequences of the present invention and are optimally at least about 10 nucleotides in length, and most optimally at least about 20 nucleotides in length. Such probes may be used to amplify corresponding polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the polynucleotide molecules of the present invention encompass polynucleotide molecules comprising a nucleotide sequence that is sufficiently identical to one of the nucleotide sequences set forth in SEQ ID NOS: 6, 7, 9, 11, 13-18, 20, 22, or 24. The term "sufficiently identical" is used herein to refer to a first amino acid or nucleotide sequence that contains a sufficient or minimum number of identical or equivalent nucleotides to a second nucleotide sequence such that the first and second nucleotide sequences have a common structural domain and/or common functional activity. For example, nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used (available on the World Wide Web at ncbi.nlm.nih.gov. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, Md., USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website on the World Wide Web at: ebi.ac.uk/Tools/clustalw/index).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The Ruby polynucleotides of the invention comprising Ruby protein coding sequences can be provided in expression cassettes for expression in the plant or other organism or non-human host cell of interest. The cassette will include 5' and 3' regulatory sequences operably linked to a Ruby polynucleotide of the invention. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the Ruby polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), polynucleotide to be expressed, and a transcriptional and translational termination region (i.e., termination region) functional in plants or other organism or host cell. The regulatory regions (i.e., promoters, transcriptional regulatory regions, and translational termination regions) and/or the polynucleotide to be expressed may be native/analogous to the host cell or to each other. Alternatively, any of the regulatory regions and/or the polynucleotide to be expressed may be heterologous or non-native to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

For expression of the Ruby protein in a plant or plant cells, the methods of the invention comprise introducing a polynucleotide construct into a plant comprising a promoter that drives expression in a plant or part or cell thereof. Any promoter known in the art can be used in the methods of the invention including, but not limited to, the tissue-preferred promoters, fruit-preferred promoters, chemical-regulated promoters, and the like. Preferred promoters of the invention are promoters that drive expression in fruit or part thereof. For expression of Ruby in citrus fruit, preferred promoters of the invention are promoters that drive expression in fruit or part thereof, particularly the carpels or endocarp. An example of a preferred promoter of the present invention is set forth in the drawing labeled as SEQ ID NO: 15. Another promoter that can be used in the methods disclosed herein is the promoter of the *Citrus sinensis* capsanthin/capsorubin synthase (CCS) gene set forth in the drawing labeled as SEQ ID NO: 16.

The termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants. Such constitutive promoters include, for example, the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced Ruby expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.—Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; *Guo Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" what is intended is presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant. In preferred embodiments of the invention, the plants are plants that are stably transformed with a polynucleotide construct of the invention.

Certain embodiments of the methods of the invention involve stably transforming a plant or cell thereof with a polynucleotide construct comprising a promoter operably linked to a Ruby coding sequence. The present invention is not limited to introducing the polynucleotide construct into the plant or plant cell as a single nucleic acid molecule but also includes, for example, introducing two or more nucleic acid molecules that comprise portions of the polynucleotide construct into the plant or plant cell, wherein the two or more nucleic acid collectively comprise the polynucleotide construct. It is recognized that the two or more nucleic acid molecules can be recombined into the polynucleotide construct within a plant cell via homologous recombination methods that are known in the art.

Alternatively, the two or more nucleic acid molecules that comprise portions of the polynucleotide construct can be introduced a plant or cell thereof in a sequential manner. For example, a first nucleic acid molecule comprising a first portion of a polynucleotide construct can be introduced into a plant cell, and the transformed plant cell can then be regenerated into a plant comprising the first nucleic acid molecule. A second nucleic acid molecule comprising a second portion of a polynucleotide construct can then be introduced into a plant cell comprising the first nucleic acid molecule, wherein the first and second nucleic acid molecules are recombined into the polynucleotide construct via homologous recombination methods.

Methods of homologous recombination involve inducing double breaks in DNA using zinc-finger nucleases or homing endonucleases that have been engineered to make double-strand breaks at specific recognition sequences in the genome of a plant, other organism, or host cell. See, for example, Durai et al., (2005) *Nucleic Acids Res* 33:5978-90; Mani et al. (2005) *Biochem Biophys Res Comm* 335:447-57; U.S. Pat. Nos. 7,163,824, 7,001,768, and 6,453,242; Arnould et al. (2006) *J Mol Biol* 355:443-58; Ashworth et al., (2006) *Nature* 441:656-9; Doyon et al. (2006) *J Am Chem Soc* 128:2477-84; Rosen et al., (2006) *Nucleic Acids Res* 34:4791-800; and Smith et al., (2006) *Nucleic Acids Res* 34:e149; U.S. Pat. App. Pub. No. 2009/0133152; and U.S. Pat. App. Pub. No. 2007/0117128; all of which are herein incorporated in their entirety by reference.

TAL effector nucleases can also be used to make double-strand breaks at specific recognition sequences in the genome of a plant for gene modification or gene replacement through homologous recombination. TAL effector nucleases are a new class of sequence-specific nucleases that can be used to make double-strand breaks at specific target sequences in the genome of a plant or other organism. TAL effector nucleases are created by fusing a native or engineered TAL effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. Genetics (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

In certain embodiments of the invention, such methods of homologous recombination can be used to insert a promoter that is introduced into a plant cell at a position that is in the vicinity of and linked to a native or non-native Ruby coding sequence that is in the genome of the plant cell, whereby the inserted promoter is in operably linkage with the Ruby coding sequence and can drive the expression of the Ruby coding sequence in the plant cell or a plant regenerated therefrom or in any part or parts of the regenerated plant. A preferred plant part for the expression of Ruby is a fruit or cell or tissue thereof. In some embodiments of the invention, the preferred plant is a citrus plant and the preferred plant part is the fruit or the carpels therein. It is recognized that the endocarp of a citrus fruit is comprised of multiple carpels and that it is the carpels which comprise the source of the juice that can be extracted from citrus fruit.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.*, 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No.

5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the a protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In specific embodiments, the nucleotide sequences of the invention can be provided to a plant using a variety of transient transformation methods. Such transient transformation methods include, but are not limited to, the introduction of the nucleotide sequence or variants and fragments thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the nucleotide sequence can be transiently transformed into the plant using techniques known in the art. Such techniques include viral vector system and *Agrobacterium tumefaciens*-mediated transient expression as described below.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), petunia (*Petunia* spp., e.g., *Petunia×hybrida* or *Petunia hybrida*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferred plant species are all *Citrus* spp. including, but are not limited to, cultivated citrus species, such as, for example, orange, lemon, meyer lemon, lime, key lime, Australian limes, grapefruit, mandarin orange, clementine, tangelo, tangerine, kumquat, pomelo, ugli, sweet orange, blond orange, blood orange, citron, Buddha's hand, and bitter orange. Preferred citrus species are sweet orange (including, for example, blond orange and blood orange), sour orange, grapefruit, pummelo, citron, lime, mandarin, clementine, and lemon.

As used herein, the term "plant" includes plant cells, plant protoplasts, plant cell tissue cultures from which plants can be regenerated, plant calli, plant clumps, and plant cells that are intact in plants or parts of plants such as embryos, pollen, ovules, seeds, leaves, cotyledons, flowers, stems, shoots, hypocotyls, epicotyls, branches, fruits, roots, root tips, buds, anthers, scions, rootstocks, and the like. The present invention encompasses all plants derived from the regenerated plants of invention provided that these derived plants comprise the introduced polynucleotides. Such derived plants can also be referred to herein as derivative plants or derivatives. The term "plant" also encompasses a tree.

The derivative plants or derivatives include, for example, sexually and asexually produced progeny, variants, mutants, and other derivatives of the regenerated plants that comprise at least one of the polynucleotides of the present invention. Also within the scope of the present invention are vegetatively propagated plants including, for example, plants regenerated by cell or tissue culture methods from plant cells, plants tissues, plant organs, other plant parts, or seeds, plants produced by rooting a stem cutting, and plants produced by grafting a scion (e.g., a stem or part thereof, or a bud) onto a rootstock which is the same species as the scion or a different species. Such vegetatively propagated plants or at least one part thereof comprise at least one polynucleotide of the present invention. It is recognized that vegetatively propagated plants are also known as clonally propagated plants, asexually propagated, or asexually reproduced plants.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed. As used herein a control fruit is a fruit produced by a control plant. Similarly, a wild-type fruit is a fruit produced by a wild-type plant.

The invention provides host cells comprising at least one polynucleotide construct or nucleic acid molecule of the present invention. Such host cells include, for example, bacterial cells, fungal cells, animal cells, and plant cells. Preferably, the host cells are non-human, host cells. More preferably, the host cells are plant cells. Most preferably, the host cells are citrus plant cells. Additionally, the invention encompasses viruses and viroids comprising at least one polynucleotide construct or nucleic acid molecule of the present invention.

The present invention provides fruit, particularly citrus fruit, with increased level of anthocyanins when compared to a wild-type fruit. It is recognized that the anthocyanins are water-soluble vacuolar pigments that may appear red, purple, or blue according to the pH, which belong to a parent class of molecules called flavonoids synthesized via the phenylpropanoid pathway. Anthocyanins are known to occur in the tissues of higher plants. Anthocyanins are derivatives of anthocyanidins, which include pendant sugars. As used herein, a fruit has an increased level of anthocyanins when the fruit has an increased level of at least one anthocyanin and/or anthocyanin derivative thereof, when compared to a wild-type or control fruit. In preferred embodiments, a fruit of the invention fruit has an increased level of total anthocyanins when compared to a wild-type or control fruit. In some embodiments, total anthocyanin content in a fruit is the total content of anthocyanins and anthocyanin derivatives in the fruit. In other embodiments, total anthocyanin content in a fruit is the total content of anthocyanins in the fruit exclusive of anthocyanin derivatives.

To further increase the anthocyanin content of the fruit, the method of the present invention comprise increasing the expression of other genes that are known in the art to be involved in the biosynthesis of anthocyanins in a plant, particularly in a fruit. The expression of such genes can be can be modified as disclosed herein for Ruby. An example of one such gene is CsMYC2.

The following examples are offered by way of illustration and not by way of limitation.

EXAMPLE

Retrotransposons Control Fruit-Specific, Cold-Dependent Accumulation of Anthocyanins in Blood Oranges Traditionally, Sicilian blood oranges have been associated with cardiovascular health and consumption has been shown to prevent obesity in mice fed a high fat diet. Despite increasing consumer interest in these health-promoting attributes, production of blood oranges remains unreliable, due largely to a dependency on cold for full color formation. We show that Sicilian blood orange arose by insertion of a Copia-like retrotransposon, which controls the expression of an adjacent gene encoding a transcriptional activator of anthocyanin production. Cold dependency reflects the induction of the retroelement by stress. A blood orange of Chinese origin results from an independent insertion of a similar retrotransposon and color formation in its fruit is also cold-dependent. Our results suggest that transposition and recombination of retroelements are likely major sources of variation in Citrus.

Materials and Methods

Plant Material

*Citrus sinensis* L. Osbeck cv. Moro, Tarocco, Doppio Sanguigno, Cadenera, Navelina and Valencia were grown at the CRA-ACM experimental farm (Palazzelli, Sicily, Italy). Different accessions of Moro, Tarocco and Navelina and the varieties Maltaise Sanguine and Sanguinelli (Spanish) were obtained from the UK National Citrus collection, (Reeds Nursery, Loddon, UK). Fruit and leaves of *Citrus sinensis* L. Osbeck cv. Jingxian were obtained from Jingzhou, Huannan Province, China. OTA and OMO hybrids grown in Palazzelli were obtained by conventional Citrus breeding methods using controlled pollinations between Oroval mandarin (*C. clementina*), used as the female parent, and Tarocco 57-1E-1 or Moro NL 58-8D-1 (*C. sinensis* L. Osbeck), used as the male parent.

Isolation of Ruby cDNA

Total RNA was extracted from Moro (CRA, Sicily) fruit flesh and reverse transcribed using a T7-oligo5 dT primer and SuperScript III RT (Invitrogen). First-strand cDNA was amplified by PCR using degenerate primers BUT-F3 and BUT-R3. The full-length cDNA was isolated using 5' and 3' SMART RACE Amplification Kit (Clontech) and gene-specific primers PMC-F1 and PMC-R1. For Jingxian, total RNA was extracted from juice and reverse transcribed using the gene-specific primer PMC-Z and SuperScript III RT. Ruby cDNA was obtained using a 5' RACE kit (Invitrogen) and gene-specific primers PMC-R1 and LeLe-R1. Primer sequences are provided in Table 1.

TABLE 1

Primers

| Name | Sequence | Description |
|---|---|---|
| BUT-F3 | GGRKTKAGRAARGGTDCATGGAC (SEQ ID NO: 18) | Degenerate primers to isolate Ruby partial cDNA |
| BUT-R3 | CCARWARTTYTTSACATCRTTWGC (SEQ ID NO: 19) | |
| PMC-R1 | TTCCCGGAAGCCTGCCCACAATCA (SEQ ID NO: 20) | Ruby 5' and 3' RACE from Moro flesh cDNA |
| PMC-F1 | CATGGACAGGAGAGGAAGATGATCT (SEQ ID NO: 21) | |
| PMC-Z | CTTACTTTGCATTGAGAAGATCCCA (SEQ ID NO: 22) | Ruby 5' and 3' RACE from Jingxian juice cDNA |
| PMC-R1 | TTCCCGGAAGCCTGCCCACAATCA (SEQ ID NO: 23) | |
| LeLe-R1 | CAACTTCATCTGCTGCAAATTCTCCT (SEQ ID NO: 24) | |
| PMC-GWF | GGGGACAAGTTTGTACAAAAAAGCAGGCTATGGCGGATTCCTTAGGAGTT (SEQ ID NO: 25) | Expression of Ruby in tobacco |
| PMC-GWR | GGGACCACTTTGTACAAGAAAGCTGGGTCTTACTTTGCATTGAGAAGATC (SEQ ID NO: 26) | |
| PMC-47 | TCCTCTCCTGTCCATGCACCTTTACGAAC (SEQ ID NO: 27) | Chromosome walking for Isolation of Ruby promoters |
| PMC-109 | GAGGAACTTGATGCCATTTTGCTTCCCCA (SEQ ID NO: 28) | |
| PMC-CF | CATTGAAGCAGGCCAGAGTTGTCCGACTGATGAC (SEQ ID NO: 29) | iPCR for isolation of Tcs1 |
| PMC-NR1 | CTCTCCTGTCCATGCACCTTTACGAACTCCTAAG (SEQ ID NO: 30) | |
| PMC-G3 | GAGAGTATACCGTATGCGTACACA (SEQ ID NO: 31) | Isolation of full-length Tcs1 |
| PMC-U | ACACGTAGCTATTGGACCACCCT (SEQ ID NO: 32) | |
| PMCi4 | GCCGAAAAGTCTCCAGTAGTGACAAAGGTGACAG (SEQ ID NO: 33) | iPCR for isolation of deletion allele and Tcs2 |
| PMCiD | TCGCTGTTCTTCCCGGAAGCCTGCCCACAATCAG (SEQ ID NO: 34) | |
| PMC-G2 | CCGAAATACAGAATGCTCAAATGGGA (SEQ ID NO: 35) | Isolation of full-length Tcs2 |
| PMC-S5 | AGCACCTACACTTACTCAACTCTC (SEQ ID NO: 36) | |
| PMC2ES-Fw | AGCTGCTGGGCAACAGATGGT (SEQ ID NO: 37) | Ruby expression qRT-PCR |
| PMC2ES-Rev | CTTCACATCGTTCGCTGTTC (SEQ ID NO: 38) | |
| GAL-POL1-Fw | GCCCGTGGACGTAGGCTAA (SEQ ID NO: 39) | Tcs1 LTR expression qRT-PCR |
| GAL-POL1-Rev | AAGAACAAGCACAAAAGAAAATACCA (SEQ ID NO: 40) | |
| GAL-POL4-Fw | TGACAGTCAGAGTGCCTTGCA (SEQ ID NO: 41) | Tcs1 Gag-Pol expression qRT-PCR |
| GAL-POL4-Rev | TCCTATGTGCTTTGTCCTGGAA (SEQ ID NO: 42) | |

Phylogenetic Analysis

Protein sequences from *Arabidopsis* and selected Myb proteins from other species belonging to subgroups 2, 4, 5, 6 and 7 were aligned using PRANK (Loytynoja and Goldman, 2008). The alignment of the DNA binding domain only was used to calculate distance estimates (the Jones Taylor Thornton matrix (JTT) model of evolution) for a neighbour-joining tree with the PHYLIP software package (Felsenstein et al, 1994). To provide statistical support for each node in the tree, a consensus tree was generated from 1000 bootstrap data sets.

Ectopic Expression of Ruby in Tobacco

The coding sequence of the Ruby cDNA was amplified with primers PMC-GWF and PMC-GWR and cloned in a pBin19-derived binary vector, previously equipped with a double CaMV 35S promoter, the CaMV Terminator with attR recombination sites in between, using Gateway® recombination technology (Invitrogen). The resulting plasmid was transferred to *Agrobacterium tumefaciens* strain LBA4404 and used to transform *Nicotiana tabacum* (cv. Samsun).

Protoplast Transfection Assays

Tobacco protoplasts were isolated from 3-5 week old leaves of *Nicotiana Tabacum* cv Samsun following the procedure described by Negrutiu et al. (Negrutiu et al., 1987). For each transfection, 10 µg of plasmid DNA containing the flavanone-3-hydroxylase (F3H) or dihydroflavonol-4-reductase (DFR) promoters from *Antirrhinum majus* fused to the β-glucuronidase (GUS) reporter gene were used. To measure expression from the promoters, plasmid DNA containing the cDNA sequences coding for the transcriptional activators AmRosea1 (4 µg: Schwinn et al., 2006) and CsMYC2 (5.5 µg) under the control of the double CaMV35S promoter were used. Different amounts of an empty plasmid containing the double CaMV35S promoter were used to ensure that equal amounts of total DNA and viral promoter were used for each transfection. After incubation for 40 h, protoplasts were collected by centrifugation and GUS activity in the cell lysate was determined according to Jefferson (Jefferson, 1987) and expressed as nmol methylumbelliferone per mg protein per minute. All transfections were performed in triplicate and GUS activity was measured in duplicate for each transfection.

Southern Blots

Citrus leaves were ground in liquid nitrogen and DNA was extracted using caesium chloride density gradient purification. DNA (10 g per sample) was digested with AseI (and numerous other restriction enzymes for mapping) for 5 h and then separated by electrophoresis. Denatured DNA was transferred to nitrocellulose membrane filters. Filters were hybridised with $^{32}$P-labelled probes overnight at 60° C. and washed in 0.1×SSC, 0.5% SDS at 60° C. for 2 h before exposure to X-Ray film (Fuji RX-100).

Isolation of Ruby Promoters

The upstream regions of Ruby from Moro and Cadenera (CRA, Sicily) were isolated by chromosome walking using the GenomeWalker Kit (Clontech) and gene-specific primers PMC-47 and PMC-109.

Isolation of Tcs1, Tcs2 and Ruby Deletion Allele

A Tcs1 fragment was initially obtained from Tarocco and Moro (Reeds, UK) DNA from leaves was digested with BsrGI and self-ligated. The Tcs1 fragment was isolated by inverse PCR using primers PMC-CF and PMC-NR1. Full-length Tcs1 was obtained by conventional PCR using primers PMC-G3 and PMC-U. A Tcs2 fragment was initially obtained from Jingxian DNA, digested with BstYI, self-ligated and amplified by inverse PCR using primers PMCi4 and PMCiD. Full-length Tcs2 was obtained by conventional PCR using primers PMC-G2 and PMC-S5. The sequence of the Ruby deletion allele (r) was obtained from OTA7 DNA using the same inverse PCR procedure and primers PMCi4 and PMCiD.

Expression Analysis of Ruby and Tcs1

Total RNA was extracted from 3 ml of juice of Moro, Tarocco, Navelina and Valencia fruit (all from CRA, Sicily) using a modified protocol described in Ancillo et al. (2007). DNAse-treated total RNA was further purified using the RNA Cleanup protocol (Qiagen) and retrotranscribed into cDNA using a High-Capacity cDNA Archive kit (Applied Biosystems). Quantitative real-time PCR was performed in optical 96-well plates with an ABI PRISM 7000 Sequence Detection System (Applied Biosystems). The PCR mixture (final volume 25 µl) contained 15 µl Power SYBR Green mix, 0.2 µM of each gene specific forward and reverse primers, 100 ng of cDNA sample, using the protocol for the Power SYBR Green PCR Master Mix (Applied Biosystems). The following standard thermal profile was used for all PCRs: 50° C. for 2 min; 95° C. for 10 min; 40 cycles of 95° C. for 15 s, and 60° C. for 1 min. Three replicates were assayed and a no-template negative control (H$_2$O control) was performed. The analyses used the relative quantification standard curve method.

Bioinformatic Analysis of LTR-Retrotransposons in Citrus

To estimate the proportion of the orange genome made up of full-length Tcs1-like elements the genome sequence of *C. sinensis* was scanned for Tcs1 sequences using the BLASTN program and the 5,413 bp Tcs1 transposon as the query sequence. Only hits with an e-value less than $e^{-50}$ and sequence identity to the Tcs1 sequence greater than 80% were used and filter masking was turned off.

The number of complete transposons identified was 78 where the BLAST high-scoring segment pair (HSP) covered greater than 70% of the length of the Tcs1 sequence. A further 47 LTR regions were identified that covered greater than 80% of the Tcs1 LTR region. Many of these hits to the LTR region had flanking hits to other regions of the transposon and were assumed to be full length transposons. Therefore, the estimated number of full length transposons is 125 and the proportion of the haploid genome sequence (296 mega bases; derived from the file called Csinensis_154.fa (July 2010) from the Phytozome website) occupied by these Tcs1-like elements is 0.23%.

To estimate the number of potentially active transposons, a Perl script was written to retrieve and translate the DNA sequence in the region of the open reading frame of the 78 complete transposons identified above. None of these translated regions were found to be without an internal stop codon therefore the corresponding elements are likely to be inactive.

Results

Identification of a Gene Encoding an R2R3 MYB Transcription Factor Expressed in the Fruit of Blood Orange Varieties Anthocyanin biosynthesis is regulated mainly at the transcriptional level (Winkel-Shirley, 2001). A regulatory complex, composed of proteins of the Myb, Basic Helix-Loop-Helix (bHLH) and WD-Repeat (WDR) families of transcription factors, governs the expression of the structural genes required for anthocyanin biosynthesis, modification and transport (Ramsay and Glover, 2005; Butelli et al., 2008). In blood orange several anthocyanin biosynthetic genes show increased expression compared to blond orange (Bernardi et al., 2010; Coltrone et al., 2010; Licciardello et al., 2008). Variation in pigment intensity or tissue specificity is governed largely by the activity of the R2R3 Myb transcription factors in the complex (Espley et al., 2007; Geekiyanage et al., 2007; Walker et al., 2007; Takos et al., 2006; Schwinn et al., 2006; Kobayashi et al., 2004). Therefore, a partial cDNA fragment encoding the conserved Myb DNA binding domain, typical of the R2R3 Myb regulators of anthocyanin biosynthesis, was isolated from RNA from Moro flesh using degenerate PCR. This fragment was extended using 5' and 3' RACE PCR on cDNA prepared from the flesh of Moro fruit, to obtain a full-length cDNA and to map the start of transcription. We were unable to amplify an equivalent cDNA from fruit of common blond oranges and found no ESTs for the gene in the database collections. We named this R2R3 Myb gene, Ruby.

Figure 1:
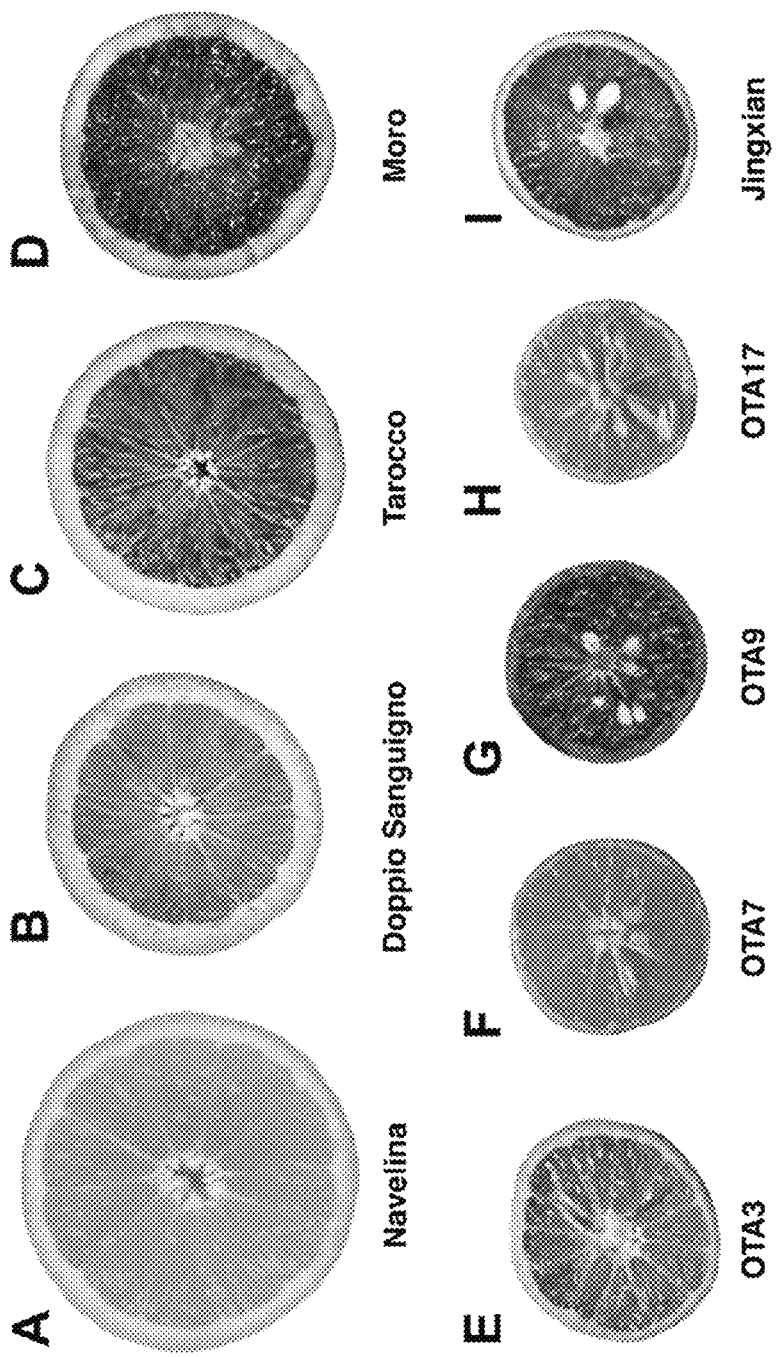
FIG. 1. Phenotypes and genotypes of orange varieties and hybrids: (A) Navelina R, r-2; (B) Doppio Sanguigno $R^D$-1, r-2; (C) Tarocco (CRA) $R^D$-1, r-2; (D) Moro (CRA) $R^D$-2, r-2; (E) OTA3 $R^D$-2, r-2; (F) OTA7 r-2, r-2; (G) OTA9 $R^D$-2, r-1; (H) OTA17 r-1, r-2; and (I) Jingxian $R^D$-3, r-2.
Figure 2:
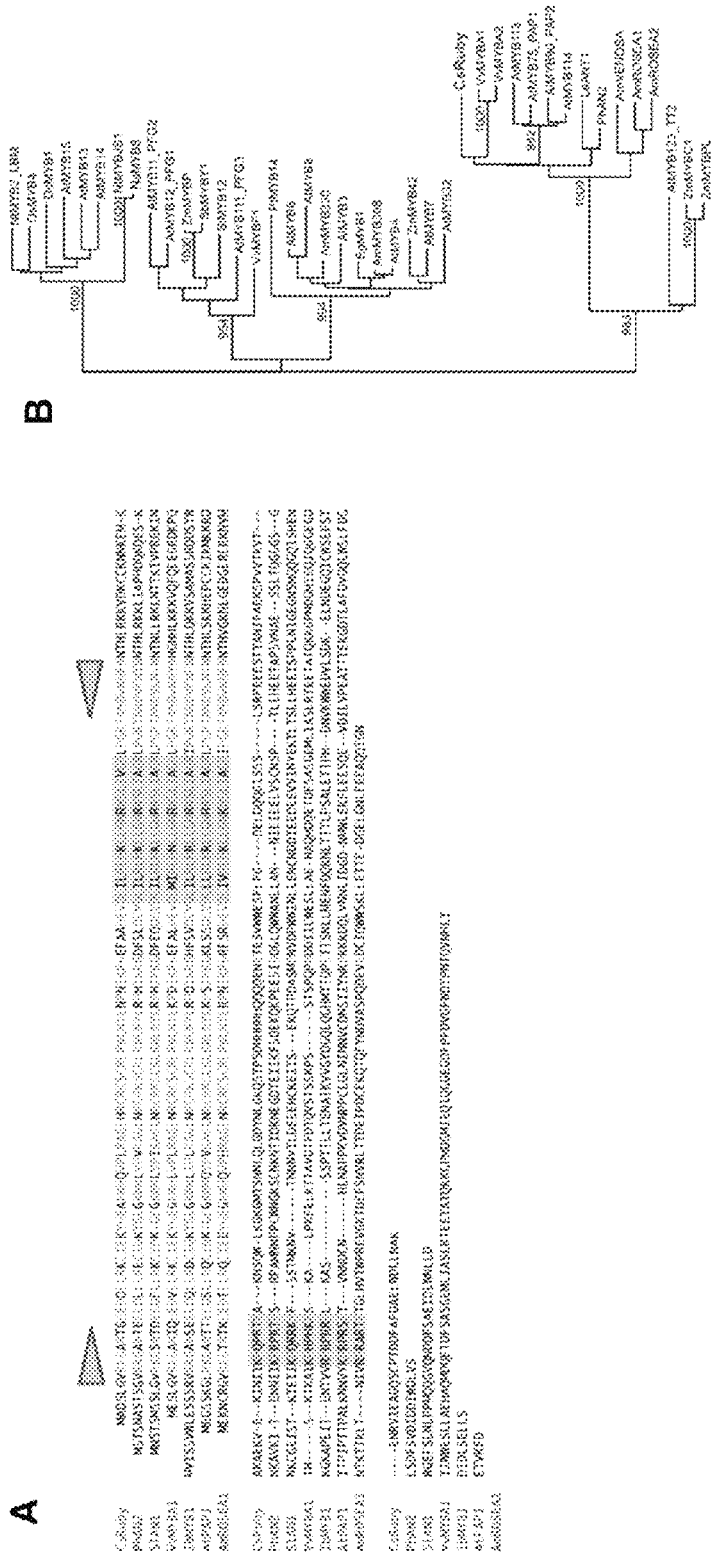
FIG. 2. Features of the protein encoded by the Ruby transcript. (A) Protein alignment of Ruby (CsRuby; SEQ ID NO: 2) with characterised members of the anthocyanin-specific family of Myb factors (available on the World Wide Web at multalin.toulouse.inra.fr/multalin/). Identical amino acids are shown in pink. The GenBank accession numbers of these proteins are as follows: PhAN2 (Petunia×hybrida), GenBank: AAF66727.1 (SEQ ID NO: 43); SlAN1 (Solanum lycopersicum), AAQ55181.1 (SEQ ID NO: 44); VvMYBA1 (Vitis vinifera), ABB87013.1 (SEQ ID NO: 45); IbMYB1 (Ipomoea batatas), BAF45118.1 (SEQ ID NO: 46); AtPAP1 (Arabidopsis thaliana), ABB03877.1 (SEQ ID NO: 47); AmROSEA1 (Antirrhinum majus), ABB83826.1 (SEQ ID NO: 48). Arrows indicate the region to which degenerated primers were designed. The signature motif for interaction with bHLH proteins within the R3 Myb DNA binding domain and the conserved motif defining members of R2R3 Myb subgroup 6 are boxed in grey. (B) Phylogenetic analysis showing that the Ruby transcription factor clusters with anthocyanin-specific members of subgroup 6 from the R2R3MYB family. Bootstrap values are shown if significant at or above the 90 percent confidence limit. Locus identifiers for Arabidopsis proteins: AtMYB3, At1g22640; AtMYB4, At4g38620; AtMYB6, At4g09460; AtMYB7, At2g16720; AtMYB8, At1g35515; AtMYB13, At1g06180; AtMYB14, At2g31180; AtMYB15, At3g23250; AtMYB32, At4g34990; AtMYB11, At3g62610; AtMYB12, At2g47460; AtMYB111, At5g49330; AtMYB113, At1g66370; AtMYB114, At1g66380; AtMYB75, At1g56650; AtMYB90, At1g66390; AtMYB123, At5g35550. Identifiers for other proteins: CsRuby, (this study, BankIt accession number: 1469607); NtMYB2, AB028649 (Nt, tobacco); DcMYB1, AB218778 (carrot); NtMYBJS1, AB236951; OsMYB4, Y11414 (rice); NaMYB8, GU451752 (Nicotiana attenuate); EgMYB1, AJ576024 (eucalyptus); AmMYB308, P81393 (Am, Antirrhinum); AmMYB330, P81395; ZmMYB42, AM156908 (Zm, maize); PtMYB14, DQ399056 (Pinus taeda); ZmMYBP, U57002; SlMYB12, EU419748 (tomato); SbMYBY1, AY860968 (Sorghum bicolour); VvMYBF1, FJ948477 (Vv, grape); AmROSEA1, DQ275529; AmROSEA2, DQ275530; AmVENOSA, DQ275531; VvMYBA1, AB097923; VvMYBA2, AB097924; LeANT1, AY348870 (Lycopersicon esculentum); PhAN2, AF146702 (Petunia hybrida); ZmMYBC1, X06333; ZmMYBPL, L19494.

The Ruby cDNA encodes a 262 amino acid protein containing an R2R3 Myb domain with a signature motif for interaction with bHLH proteins from the clade 3f (DLX$_2$RX$_3$LX$_6$LX$_3$R, SEQ ID NO: 49; Lin-Wang et al., 2010; Zimmermann et al., 2004; Heim et al., 2003; FIG. 2A). It also has a conserved sequence motif KPXPR(S/T)F (SEQ ID NO: 50) in its C-terminal domain found in other R2R3 Myb regulators of anthocyanin biosynthesis (Lin-Wang et al., 2010; Stracke et al., 2001) Phylogenetic analysis revealed that Ruby clusters with members of R2R3 Myb subgroup 6, known to regulate anthocyanin biosynthesis in dicotyledonous plants (Lin-Wang et al., 2010; Bailey et al., 2008; FIG. 2B).

Ruby is a Regulator of Anthocyanin Biosynthesis

Figure 3:
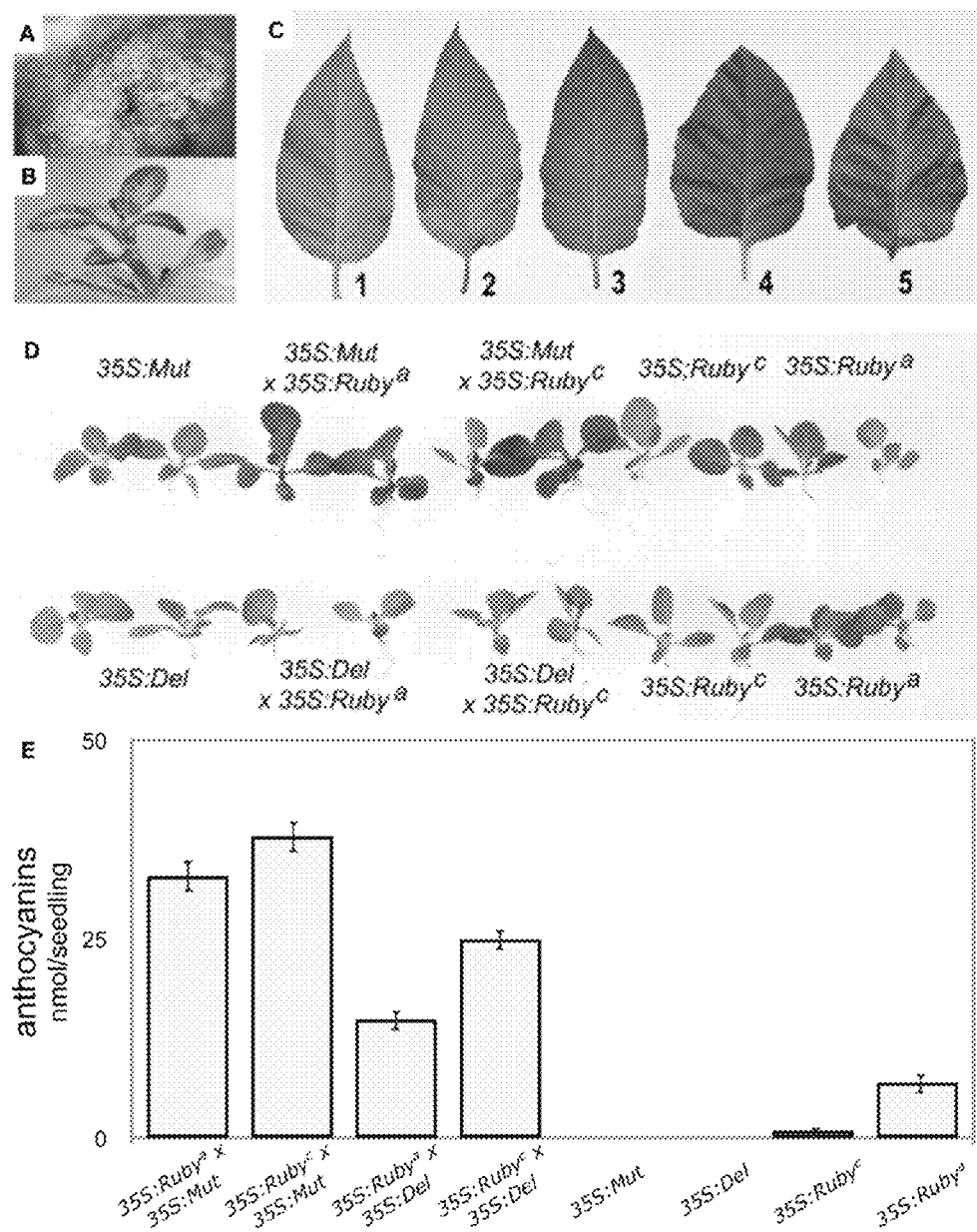
FIG. 3. Ruby is a regulator of anthocyanin biosynthesis. Constitutive expression of Ruby cDNA under the control of the 35S promoter in tobacco results in strong anthocyanin-based pigmentation in (A) undifferentiated callus and (B) regenerating shoots. (C) Coexpression of the bHLH regulatory genes Delila and Mutabilis increases further anthocyanin accumulation in mature leaves: (1) 35S:Ruby (2) 35S: Ruby×35S:Delila (3) 35S:Ruby×35S:Mutabilis (4) 355: Rosea1×35S: Delila (5) 355:Rosea1×35S: Mutabilis (D) Ruby partners more successfully with the bHLH protein Mutabilis than with the bHLH protein Delila to activate anthocyanin biosynthesis in tobacco. Anthocyanin accumulation in two seedlings of each genotype are shown. (E) Anthocyanin content in tobacco seedlings transformed with different regulatory genes.

The ability of Ruby to activate anthocyanin biosynthesis was verified by its ectopic expression under the control of the constitutive CaMV 35S promoter in tobacco, where it resulted in visible purple-red pigmentation in undifferentiated callus and in developed tissues of regenerated plants (FIG. 3A). Co-expression of Ruby with the Delila and Mutabilis genes encoding bHLH transcription factors of clade 3f from *Antirrhinum majus* (Schwinn et al., 2006), known to interact with anthocyanin-specific Myb factors, enhanced pigmentation in tobacco (FIG. 3B). Ruby promoted stronger pigmentation in combination with Mutabilis than with Delila, suggesting some selectivity in the ability of the Ruby MYB protein to interact with different bHLH partners (FIG. 3B). These bioassays confirmed the functionality of Ruby as a regulator of anthocyanin biosynthesis. A cDNA encoding a clade 3f bHLH protein (CsMYC2) has been identified in orange (Coltrone et al., 2010). We showed, using transfection assays, that this bHLH protein will induce expression from the promoters of anthocyanin biosynthetic genes in combination with the Rosea1 R2R3 Myb regulator of anthocyanin biosynthesis from *Antirrhinum majus* (FIG. 9). These data support the idea that it is the expression of Ruby that limits anthocyanin biosynthesis in blood oranges because the CsMYC2 gene (encoding the bHLH partner in the MBW complex) is expressed at detectable levels in both blond and blood oranges (Coltone et al., 2010).

Expression of Ruby in Blood and Blond Orange Accessions

Figure 4:
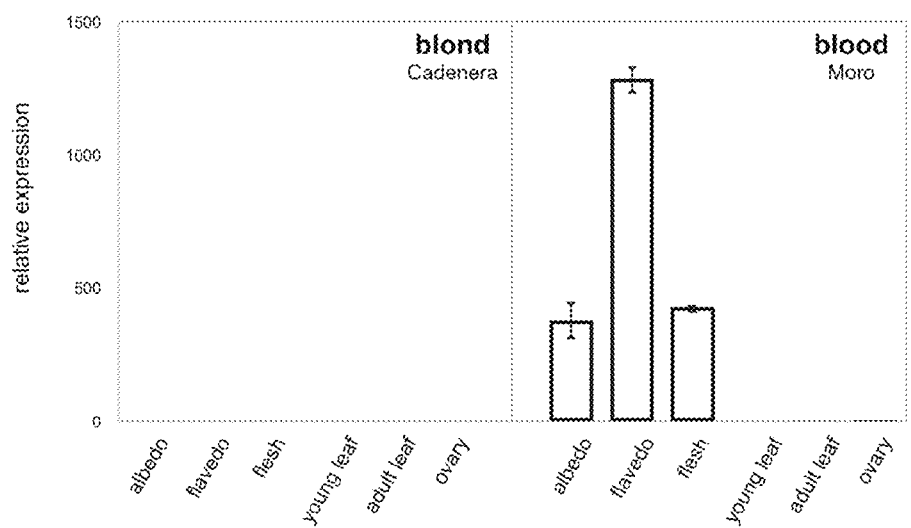
FIG. 4. Expression analysis of Ruby. (A) Expression of Ruby in different tissues of blond Cadenera and blood Moro oranges. Albedo is the spongey white layer of the orange peel. The flavedo is the peripheral surface of the pericarp. (B) Expression of Ruby in diploid hybrids obtained crossing mandarin (C. clementina cv. Oroval) with C. sinensis cv. Moro (OMO series) or C. sinensis cv. Tarocco (OTA series). Hybrids lacking anthocyanins (OMO41,3,5, OTA11,17,31, 35) appear slightly different colours due to varying carotenoid levels in the fruit flesh.
Figure 4:
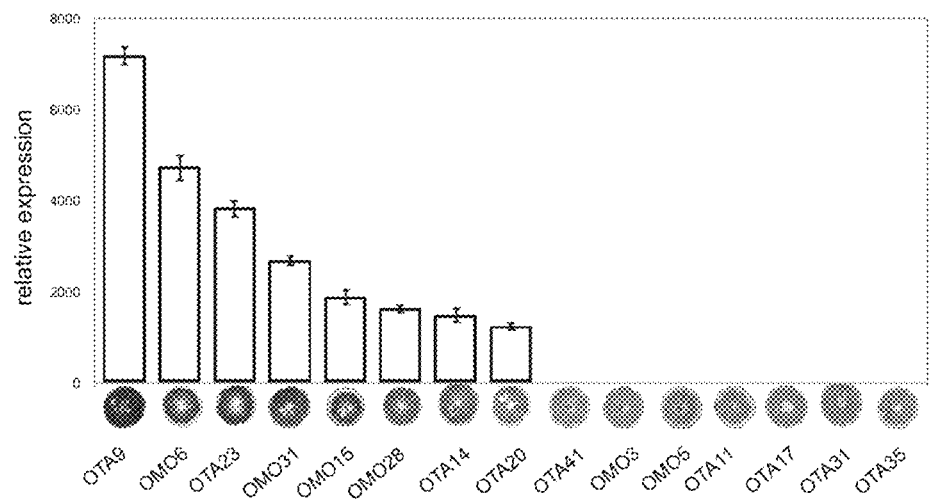

In blood oranges, Ruby expression was limited to the fruit (FIG. 4A). High levels of Ruby expression were detected in flesh and rind, including the white, spongy inner lining (albedo). Expression of Ruby was not detected in blond oranges (FIG. 4A). We tested the levels of Ruby expression in different accessions of blood orange and in hybrids between Moro and mandarin (OMO) and Tarocco and mandarin (OTA), produced in the experimental orchard of the Centro di Ricerca per l'Agrumicoltura e le Colture Mediterranee (CRA; Rapisada et al., 2009). The different orange accessions and the hybrids displayed a range of pigmentation levels when grown under equivalent conditions, from very high pigmentation (OTA9), medium pigmentation (OMO6, OTA23, OMO31, OMO15), low pigmentation (OMO28, OTA14, OTA20) through to no pigmentation (OTA41, OMO3, OMO5, OTA11, OTA17, OTA31, OTA35). The levels of Ruby transcript in the flesh of fruit grown under the same conditions at the field station were determined by qRT-PCR. There was a clear correlation between the levels of Ruby transcript and the levels of anthocyanin in fruit flesh (FIG. 4B). Expression of Ruby was also detected in ancient varieties belonging to the Sanguigno/Sanguinello group, generally characterized by light pigmentation of their flesh (FIG. 10).

Molecular Constitution of Ruby in Sweet Oranges

Blood orange is a derivative of sweet orange which is believed to be an interspecific hybrid between pummelo and mandarin (Li et al. 2011; Moore, 2001; Mabberley, 1997). To establish the genotypic constitution of different orange varieties at the Ruby locus, genomic DNA was extracted from leaves of pummelo, mandarin, and different sweet orange accessions. Pummelo contains two similar potentially functional alleles of Ruby, one of which showed complete sequence identity over 1.7 kb with the R allele identified in blond orange varieties. Mandarin was heterozygous at the Ruby locus. One allele contains a stop codon in the third exon of the gene which is predicted to result in an inactive Ruby protein. We termed this allele r-1. To characterise the second Ruby allele we used inverse PCR to identify a 2006 bp deletion which encompasses the first two exons of the Ruby gene and 1.4 kb of the region upstream (FIG. 6), creating a non-functional allele, which we named r-2. This second Ruby allele was present in mandarin and all orange varieties (FIG. 6). Our data from the Ruby locus confirm that sweet orange is a hybrid between pummelo and mandarin, and has inherited the R allele from pummelo and the r-2 allele from mandarin. Diploid mandarin carries two non-functional alleles of Ruby (r-1, r-2) implying that the generation of a 'blood' mandarin would be highly improbable. The haploid sequenced genome of mandarin (available on the World Wide Web at phytozome.net) carries the r-1 allele.

Molecular Differences at the Ruby Locus Between Blood and Blond Oranges

Figure 5:
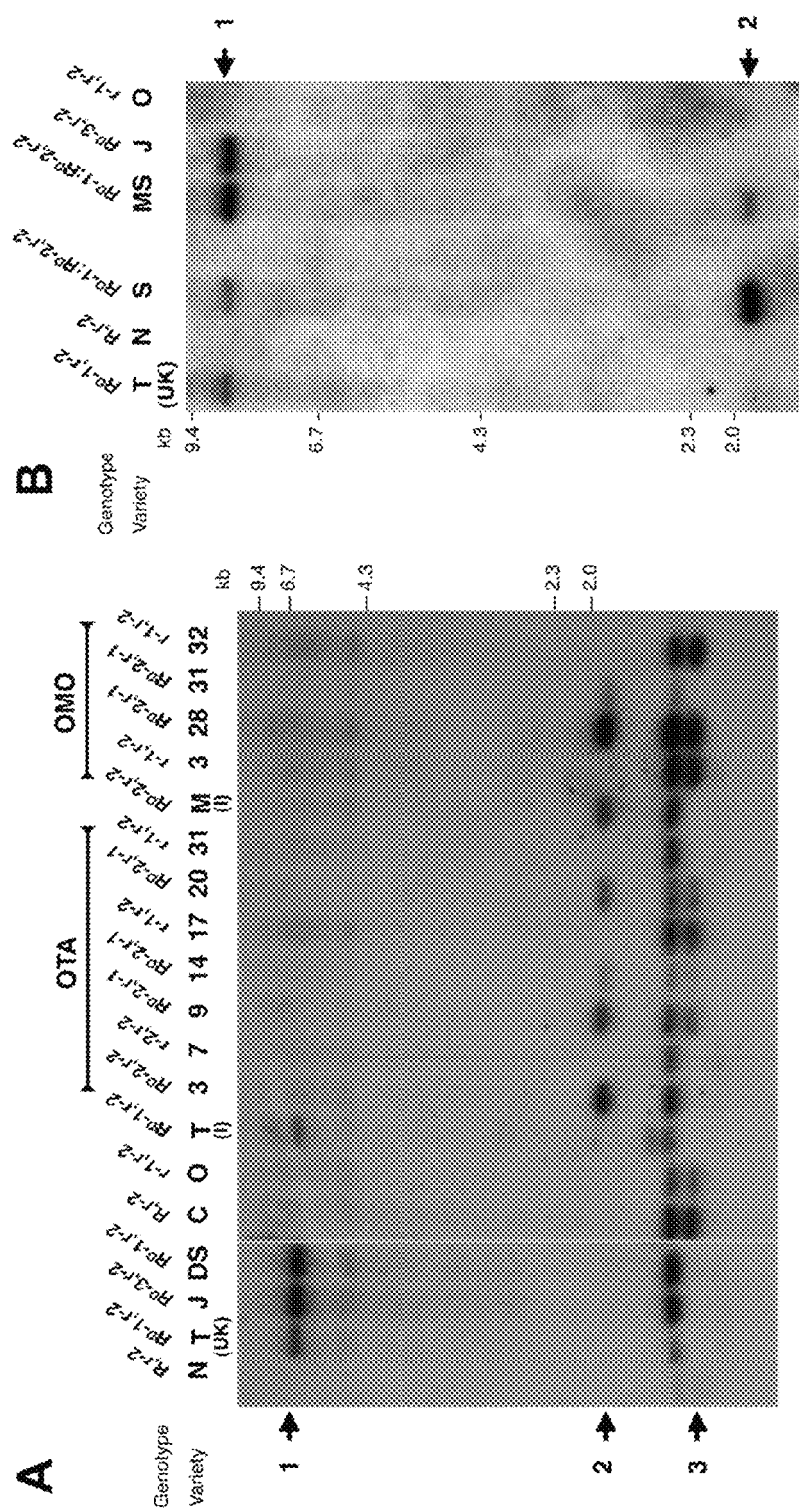
FIG. 5 Genomic characterization of the Ruby locus. (A) Southern blot of genomic DNA from different blood and blond orange varieties and from hybrids between Tarocco and mandarin (OTA) and Moro and mandarin (OMO) digested with AseI and probed with a $^{32}$P-labelled probe of the Ruby gene from 465 bp upstream of the ATG to the stop codon of the gene. Varieties: N=Navelina; T (UK)=Tarocco from Reeds (UK); J=Jingxian; DS=Doppio Sanguigno; C=Cadenera; O=Oroval Clementine (mandarin); T (I)=Tarocco from CRA, Italy; M (I)=Moro from CRA; OTA hybrids 3, 9, 14, and 20 are pigmented with anthocyanin; OMO hybrids 28 and 31 are pigmented with anthocyanin. Band 1 is the AseI fragment at the 5' end of the Ruby gene with the full retroelement insertion (Tcs1 for Tarocco and Doppio Sanguigno and Tcs2 for Jingxian). Band 2 is the AseI fragment at the 5' end of the Ruby gene containing the solo LTR insertion. Band 3 is the AseI fragment at the 5' end of the Ruby gene without any insertion (ie the wild type R allele) present in blond oranges. (B) Southern blot of genomic DNA from different blood and blond orange varieties. Genomic DNA was digested with AseI and probed with a $^{32}$P-labelled probe of the Ruby gene from 465 bp upstream of the ATG to the stop codon of the gene. The gel was run for longer than that shown in FIG. 2A, so that only the 5' fragments of the Ruby gene with insertions remained on the gel. Varieties: T=Tarocco (Reeds, UK); N=Navelina.

The Ruby gene was cloned from three blood (Sanguinelli, Maltaise Sanguine and Moro) and three blond (Navelina, Salustiana and Cadenera) varieties by PCR of genomic DNA. Sequence analysis revealed 100% nucleotide identity in the three exons and two introns that constitute the gene among the 6 varieties. The dramatic differences in expression of Ruby between blood and blond oranges suggested that they resulted from differences in the regulation of transcription of Ruby. The upstream regulatory regions of Ruby from Moro and Cadenera were isolated by chromosome walking and sequencing revealed an insertion of 501 nucleotides in Moro, 254 bp upstream of the initiating ATG in Ruby, compared with the otherwise identical Ruby promoter from the blond Cadenera orange (FIG. 5 and FIG. 6). The insertion showed sequence homology to the Long Terminal Repeats (LTRs) of the Copia family of retrotransposons, and included a 5 bp direct repeat, typical of LTR retroelement insertion sites (Kim et al., 1998).

DNA from the different blood orange accessions and from hybrids derived from the crosses between Moro (OMO hybrids) or Tarocco (OTA hybrids) and mandarin (Rapisada et al., 2009) was then mapped, amplified and sequenced (FIG. 5A). An accession of Moro from the UK National Citrus collection (Reeds Nursery Loddon, UK) had a larger insertion in the region upstream of the Ruby gene than the Moro accession from CRA, Acireale, Sicily. The same, larger insertion (termed $R^D$-1) was present in accessions of Tarocco from both CRA and the Reeds collection, in Maltaise Sanguine and Doppio Sanguigno representing older varieties of Italian blood oranges (Hodgson, 1967; Chapot, 1963) as well as in the Spanish Sanguinelli derived from Doblefina (FIG. 5A,B). The large insertions in Moro (Reeds), Tarocco, Maltaise Sanguine, Doppio Sanguigno and Sanguinelli were identical and corresponded to a complete retrotransposon, which we named Tcs1.

Tcs1 is 5413 nucleotides in length and shows all the features of a typical Copia-like long terminal repeat (LTR) retrotransposon. It contains an open reading frame, which encodes the proteins (Gag and Pol) required for the reverse transcription of the element and integration into the host genome, flanked by two identical LTRs of 496 nucleotides, identical to the solo LTR insertion in the Sicilian Moro (CRA). Because Tcs1 encodes complete Gag and Pol proteins it is likely an active retrotransposon and because the LTRs of Tcs1 at the Ruby locus are identical, it is likely that this is a very recent insertion.

A precise copy of Tcs1 is not present in the recently released sequence of the diploid *C. sinensis* genome (available on the World Wide Web at phytozome.net). Two closely related elements are present in the more accurately sequenced genome of a haploid *C. reticulata* (mandarin). They have identical LTRs to Tcs1 but differ in the non-coding region downstream of the 5'LTR. Several hundred Tcs1-like sequences can be identified in both species, the vast majority predicted to be inactive. In *C. sinensis*, LTR-retrotransposons have been estimated to constitute around 23% of the genome (Rico-Cabanas and Martinez-Izquierdo, 2007), but we calculate full length Tcs1-like copies, which have two LTRs available for recombination, constitute only about 0.23% of the genome and we could find no 'active' Tcs1-like copies with complete open reading frames in the available sequence.

Recombination Between LTRs of Tcs1 Gives Plants Chimeric at the Ruby Locus or Progeny with Just the LTR Insertion at the Ruby Locus In addition to the insertion of the full Tcs1 element at the Ruby locus (which generated the dominant $R^D$-1 allele), the DNA from the leaves of Maltaise Sanguine and Sanguinelli accessions also contained versions of the Ruby locus with just the LTR inserted upstream, as shown by Southern blots and PCR (FIG. 5B). We deduced that these accessions are chimeric for insertions of the full element and the solo LTR. The intensity of the signal from the fragment containing the solo LTR from both Maltaise Sanguine and Sanguinelli suggests that these accessions are periclinal chimeras for the Ruby locus; a recombination could have occurred in the L1 or L2/L3 layers and then have been maintained over long periods of time because these varieties are propagated largely by grafting, as has been reported to occur commonly in other clonally propagated crops like grape (Pelsy, 2010).

Amongst the hybrids between Tarocco and mandarin (OTA hybrids) all those with pigmented fruit flesh had an insertion of the solo-LTR at the Ruby locus although a vegetative clone of the Tarocco parent plant used for the crosses had the full Tcs1 insertion (FIG. 5A). This showed that recombination can occur in the germline and suggested that it might be induced by meiosis. We also identified two accessions of Moro, one (Reeds UK) with the full Tcs1 retroelement insertion and the other, (CRA), with just the solo-LTR at Ruby indicating that unequal crossing over can also occur somatically (because blood orange is propagated by cuttings) and give rise to non-chimaeric progeny.

Retroelement Expression Controls the Expression of Ruby in Blood Orange

Retrotransposons can insert within or near transcriptionally active regions and can cause mutations by disrupting genes, altering their expression or driving genomic rearrangements (Shapiro, 2005; Feschotte et al., 2002; McClintock, 1984). We mapped the start of Ruby transcription by 5' RACE PCR on cDNA prepared from RNA from Moro fruit flesh. The start of transcription mapped to an A, 551 nucleotides upstream of the initiating ATG of the Ruby gene. A TATA box was identified 32 bp upstream of the start of transcription within the LTR, whereas it was not possible to identify a TATA box in the sequence upstream of the Ruby gene in the R allele from blond oranges. The LTR also provided a 5' donor splice site for the first intron in the Ruby transcript, the 3' acceptor site being located within the sequences upstream of the Ruby open reading frame. A second intron detected in the Ruby transcript from Moro blood orange, was defined by donor and acceptor sites within the 5'UTR of the Ruby sequence (FIG. 7). We concluded that when Tcs1 is inserted at the Ruby locus, it must provide the regulatory sequences for initiating expression of the Ruby gene, since the transcription start site maps to the LTR.

Transcription of active retroelements, a prerequisite for transposition, is usually repressed by the host. However, activation in response to a variety of biotic and abiotic stresses is a common feature of most retrotransposons (Wessler, 1996). McClintock's theory of genome shock suggested that enhanced transposition under stress might represent an evolutionary strategy to increase the chances of survival under unfavorable conditions (McClintock, 1984). We therefore investigated whether the expression pattern of Ruby in blood oranges was a function of the expression of Tcs1 particularly in response to cold stress.

To assess the activity of Tcs1 and Tcs1-like elements, two sets of primers corresponding to the transcribed portion of the LTR or internal to the 'Gag-Pol' region of the element (FIG. 7) were used for qRT-PCR. The downstream primer for the transcript of the LTR corresponded to a sequence which is spliced from the Ruby transcript in the first intron in blood oranges (FIG. 7). Consequently, the Tcs1 LTR transcript levels we measured did not include those from the Ruby locus.

Tcs1 transcripts could be detected in fruit, but not in leaves, of blood oranges. Elevated levels of Tcs1 transcripts were observed in Tarocco and Moro blood varieties following storage of fruit in the cold, indicating that Tcs1 and Tcs1-like elements are activated by cold and ultimately are responsible for temperature-dependent anthocyanin accumulation in blood oranges (FIG. 7). The expression of Tcs1 matched well the change in transcript levels of Ruby in blood orange varieties in response to cold storage (FIG. 7). Since in Moro (CRA) the solo LTR controls expression of Ruby, cold-dependent transcriptional activation appears to be an intrinsic feature of Tcs1-like elements, irrespective of their association with the Ruby locus. Consequently, in the Sicilian blood orange varieties, the fruit-specific, cold-inducible production of anthocyanin (FIG. 7) is a feature of the regulation of the Tcs1 element, which controls expression of Ruby as a result of the positioning of the strong promoter provided by the 3' LTR adjacent to the Ruby gene. Moro produces higher levels of anthocyanins than Tarocco. The higher anthocyanin production in Moro fruit is accompanied by higher expression of Tcs1. Consequently, the selection of sports producing more deeply pigmented fruit flesh likely reflects selection for higher levels of Tcs1 transcription during the derivation of improved blood orange cultivars.

An Independent Blood Orange Accession from Jingxian, China

Today, blood oranges are grown in places as far apart as Japan, Australia, South Africa, Pakistan, Calif., China and Iran. However, the unreliable production associated with existing commercial blood orange varieties due to their cold dependency, means that the availability and consumption of blood orange on a global scale has declined in recent years (Zarba and Pulvirenti, 2005). There is considerable interest in identifying independent blood orange types that might be free from these production problems. We therefore looked amongst existing blood orange accessions for any independent events. Because of apomixis and a long juvenile phase, oranges, like most Citrus species, are almost exclusively propagated by grafting on selected rootstocks. Striking phenotypic diversity is due to the selection of superior or unusual branches derived from bud mutations. Our molecular analyses showed that Sanguinelli, which is a derivative of the Spanish Doblefina, shared a common origin with Sicilian blood oranges. Shamouti Blood Orange has been reported to be a chimera (Spiegel-Roy, 1979), possibly derived from grafting with Maltaise Sanguine (Hodgson, 1967), and is, therefore, also unlikely to represent an independent event.

Most of the blood orange cultivars grown in China are of direct or indirect Sicilian origin. However, one old variety, Jingxian, has been retained and is believed to be the only blood orange of Chinese origin (Yuan et al., 2008). Jingxian blood orange was first recorded in the *Official Record for Huaihua Region* in 1996. In 1965, when people began to select out this variety, the oldest tree they found in the countryside was about 70 years old. Consequently, the Jingxian blood orange has existed for at least 110 years.

Southern blot analysis indicated that Jingxian contains a DNA insertion in the Ruby locus of similar size to Tcs1 (FIG. 5A). However, inverse PCR showed this to be a different element, which we named Tcs2 (FIG. 6). Tcs2 is 5454 bp long, generates a 5 bp direct duplication upon insertion and is similar in sequence to Tcs1, except for the first half of the two LTRs that differ considerably. Like Tcs1, Tcs2 appears to be an active retroelement. In Jingxian blood orange, Tcs2 is inserted in the Ruby locus just 196 nucleotides upstream of the Tcs1 insertion site and 450 bp upstream of the Ruby ATG, but it is inserted in the opposite orientation to Tcs1 relative to the Ruby gene (FIG. 6).

The blood phenotypes in both Jingxian and the Sicilian group of blood oranges are therefore of independent origin showing that different members of the same family of retrotransposons may alter the expression of nearby genes through parallel but distinct mechanisms.

Despite smaller fruit size and higher seed content, confirming that Jingxian is a relatively distant cousin of Sicilian blood oranges, Jingxian fruit display the same pattern of cold-induced, fruit-specific anthocyanin accumulation as Sicilian and Spanish blood oranges, suggesting Tcs2 to be cold-inducible as well. For the LTR of Tcs2 to drive expression of Ruby, it must provide a bidirectional activator sequence. We mapped the start of transcription of Ruby in Jingxian juice to a position 321 nucleotides downstream of the Tcs2 insertion (FIG. 6). No TATA box was evident in the sequence ~30 bp upstream of this transcriptional start site. Our data suggest that Tcs2 provides an upstream activating sequence that controls the expression of Ruby and the production of anthocyanin concordant with its own expression.

Activity of Copia-Like Retroelements in Citrus

A priori, the probability of independent gain-of-function mutations involving the same family of retroelements is low, especially given that Citrus varieties are almost exclusively vegetatively propagated. However, genome shock of the type caused by interspecific hybridisation does induce retroelement expression and transposition. It may be that the relatively recent origin (in terms of meiotic cycles) of sweet orange through interspecific hybridization between pummelo and mandarin (Li et al. 2011; Moore, 2001; Mabberley, 1997) induced accompanying high levels of retroelement activity which have been further selected during breeding of blood orange. Indeed, active retroelements may represent a major source of variation available to breeders of Citrus who depend on mutation-based differences that arise in buds (de Felice et al., 2008; Tao et al., 2005). Comparison of the DNA of the OTA hybrids and their parental lines showed new insertions of Tcs1-like elements following this interspecific cross (FIG. 8A). However, more striking was the high frequency of unequal crossing over between the LTRs of the full element to leave solo LTR insertions (FIG. 8B). This has also occurred at the Ruby locus in our accessions of Sanguinelli, Maltaise Sanguine, Moro and Tarocco. Sweet orange is a relatively recent derivative from an interspecific hybridization and the genome shock resulting from such hybridization may have stimulated higher levels of unequal crossing over. Interestingly, Parisod et al., (2009) highlighted significant structural changes occurring as a result of recombination involving retroelements, rather than transposition, during interspecific hybridization and allopolyploidisation in plants (Parisod et al., 2009).

Discussion

The molecular analysis of the Ruby locus indicates that the genomes of pummelo (Citrus maxima) and mandarin (Citrus reticulata) combined to generate the genome of sweet orange (Citrus sinensis), confirming its reported hybrid origin (Li et al., 2010; Moore, 2001; Mabberley, 1997). At the Ruby locus the genetic contributions of the two parental species were equal and the functional allele of Ruby was provided by the pummelo parent. Although encoding a functional protein, this allele appears to be inactive in common blond orange, because we were unable to amplify any transcripts from this locus from any tissues of blond orange plants. Confirming its apparent lack of expression, no ESTs are available in the Citrus EST databases. Lack of Ruby expression may explain why anthocyanins, common pigments in most plant species, are rare in Citrus, and why mandarins, which carry only non-functional alleles of Ruby, never produce anthocyanins.

Our results indicate that all commercial blood orange varieties have a common origin. Anthocyanin pigmentation of fruit must have originated once either in a Mediterranean sweet orange or in a Chinese sweet orange which has since been lost. Citrus breeders have derived all the diversity in modern blood orange varieties from this original event. The molecular basis of the blood orange trait is retrotransposon-mediated transcriptional activation of the Ruby Myb gene. This is particularly clear in Sicilian blood oranges where the start of transcription of Ruby lies within the 3' LTR of Tcs1. This provides a striking example of the role of transposable elements as controlling elements in the regulation of gene expression, adaptation to environmental stresses and genome evolution. Our discovery of a second independent insertion of a retroelement giving the same gain-of-function phenotype as in Sicilian blood oranges, illustrates the strength of the LTR as a promoter and also as an upstream activating sequence in the independent Jingxian blood orange. Both Tcs1 and Tcs2 insertions in Ruby give rise to induction of anthocyanin biosynthesis specifically in fruit, which is heavily influenced by environment. The cold dependency of anthocyanin production in blood orange results from the cold induction of retroelement transcription. The expression of Copia-like retrotransposons is determined by sequences within the LTRs which, in blood oranges, provide either a surrogate promoter with a TATA box and a transcriptional start as seen in commercial blood oranges, or an upstream activator sequence as seen in Jingxian orange. Consequently Ruby expression mirrors retroelement expression and is fruit-specific and cold-inducible.

Different accessions of blood orange demonstrate the high levels of recombination and transposition associated with the retroelements and suggest that they may be responsible for generating much of the diversity available to Citrus breeders (de Felice et al., 2009; Rico-Cabanas, and Martínez-Izquierdo, 2007; Tao et al., 2005). However, recombination between Tcs1 LTRs at the Ruby locus does not result in phenotypic changes in the levels of anthocyanins produced, confirming that the solo LTR carries all the information for the control of Ruby expression in Sicilian blood oranges. This is unlike the situation in grape. In grape, insertion of the Gypsy-like retrotransposon, Gret1, suppresses expression of a Myb gene (VvMYBA1) and it is believed that this insertion underpinned the development of white-skinned berries (Fournier-Level et al., 2010; Kobayashi et al., 2004). Recombination between Gret1 LTRs results in some restoration of Myb gene function and blush-skinned sports such as Chardonnay Rose and Flame Muscat (Pelsy, 2010).

The two independent blood orange derivatives, Jingxian and Sicilian blood oranges represent parallel gains of function, and therefore our results offer little hope of generating or identifying new varieties of blood orange that are free from the major limitation of cold dependency by conventional Citrus breeding methods. However, our improved understanding of the genetic and molecular basis of the blood orange trait could offer relatively straightforward solutions to the requirement for blood orange varieties with dependable production in warmer climates, through genetic engineering. Such strategies could provide new blood orange varieties suitable for the major areas of Citrus cultivation and could contribute significantly to increasing production of health-promoting blood oranges.

REFERENCES

Ancillo, G., Gadea, J., Forment, J., Guerri, J., and Navarro, L. (2007) Class prediction of closely related plant varieties using gene expression profiling. J Exp Bot. 58: 1927-33.

Bailey, P. C., Dicks, J., Wang, T. L., and Martin, C. (2008). IT3F: A web-based tool for functional analysis of transcription factors in plants. Phytochem. 69: 2417-2425.

Bernardi, J., Licciardello, C., Russo, M. P., Chiusano, M. L., Carletti, G., Recupero, G. R., and Marocco, A. (2010) Use of a custom array to study differentially expressed genes during blood orange (Citrus sinensis L. Osbeck) ripening. J. Plant Physiol. 167: 301-310.

Bonina, F. P., Leotta, C., Scalia, G., Puglia, C., Trombetta, D., Tringali, G., Roccazzello, A. M., Rapisarda, P., and Saija, A. (2002) Evaluation of oxidative stress in diabetic patients after supplementation with a standardised red orange extract. Diabetes Nutr. Metab. 15: 14-19.

Bradley, J. M., Deroles, S. C., Boase, M. R., Bloor, S., Swinny, E., and Davies, K. M. (1999) Variation in the ability of the maize Lc regulatory gene to upregulate flavonoid biosynthesis in heterologous systems. Plant Sci., 140: 31-39.

Butelli, E., Titta, L., Giorgio, M., Mock, H. P., Matros, A., Peterek, S., Schijlen, E. G. W. M., Hall, R. D., Bovy, A. G., Luo, J., and Martin, C. (2008) Enrichment of tomato fruit with health-promoting anthocyanins by expression of select transcription factors. Nature Biotech. 26: 1301-1308.

Chapot, H. (1963) Quelques oranges sanguines. Cah. Rech. Agron. [Rabat] 18: 61-87.

Coltrone, A., Controneo, P. S., and Reforgiato-Recupero, G. (2010). Cloning and molecular characterisation of R2R3-MYB and bHLH-MYC transcription factors from Citrus sinensis. Tree Genet. Genom. 6: 101-112.

Crifò T., Puglisi I., Petrone G., Recupero G. R., and Lo Piero A. R. (2011). Expression analysis in response to low temperature stress in blood oranges: implication of the flavonoid biosynthetic pathway. Gene 476: 1-9.

de Felice, B., Wilson, R. R., Argenziano, C., Kafantaris, I., and Conicella, C. (2009) A transcriptionally active Copia-like retroelement in Citrus limon. Cell. Mol. Biol. Lett. 14: 289-304.

de Pascual-Teresa, S., Moreno, D. A., and Garcia-Viguera, C. (2010) Flavanols and Anthocyanins in Cardiovascular Health: A Review of Current Evidence. Int. J. Mol. Sci. 11: 1679-1703.

Davies, K. M. (2007) Genetic modification of plant metabolism for human health benefits. Mut. Res. 622: 122-137.

Espley R. V., Hellens, R. P., Putterill, J., Stevenson, D. E., Kutty-Amma, S., and Allan, A. C. (2007) Red colouration in apple fruit is due to the activity of the MYB transcription factor, MdMYB10. Plant J. 49: 414-427.

Felsenstein, J. (2004). PHYLIP (Phylogeny Inference Package) version 3.6. Distributed by the author. Department of Genome Sciences, University of Washington, Seattle.

Ferrari, G. B. (1646) Hesperides Sive Malorum Aureorum Cultura et Usu. (Romae, sumptibus Hermanni Scheus., 1646), Libri Quatuor.

Feschotte, C., Jiang, N., and Wessler, S. R. (2002) Plant transposable elements: Where genetics meets genomics. Nature Rev. Genet. 3: 329-341.

Geekiyanage, S., Takase, T., Ogura, Y., and Kiyosue, T. (2007) Anthocyanin production by over-expression of grape transcription factor gene VlmybA2 in transgenic tobacco and Arabidopsis. Plant Biotech. Rep. 1: 11-18.

Guarnieri, S., Riso, P., and Parrini, M. (2007) Orange juice vs Vitamin C: effect on hydrogen peroxide-induced DNA damage in mononuclear blood cells. Brit. J. Nutr. 97: 639-643.

Hellens, R. P., Moreau, C., Lin-Wang, K., Schwinn, Kathy E., Thomson, S. J., Fiers, M. W. E. J., Frew, T. J., Murray, S. R., Hofer, J. M. I., Jacobs, J. M. E., Davies, K. M., Allan, A. C., Bendahmane, A., Coyne, C. J., Timmerman-Vaughan, G. M., and Ellis, T. H. N. (2010) Identification of Mendel's White Flower Character PLOS ONE, 5: e13230.

Hodgson, R. W. (1967) in The Citrus Industry. Vol. I. History, World Distribution, Botany and Varieties, W. Reuther, H. J. Webber, L. D. Batchelor Eds. (Univ. of California), pp. 431-591.

Holmes, E. M. (1924) The origin of the Maltese blood orange. Pharm. J. and Pharmacist. 614-615.

Jayaprakasha, G. K., and Patl, B. S. (2007) In vitro evaluation of the antioxidant activities in fruit extracts from citron and blood orange. Food Chem. 101: 410-418.

Jefferson, R. A. (1987). Assaying chimeric genes in plants: the GUS gene fusion system. Plant Mol. Biol. Rep. 5: 387-405.

Kelebek, H., Canbas, A., and Selli, S. (2008) Determination of phenolic composition and antioxidant capacity of blood orange juices obtained from cvs Moro and Sanguinelli (Citrus sinensis (L) Osbeck) grown in Turkey. Food Chem. 107: 1710-1716.

Kim, J. M., Vanguri, S., Boeke, J. D., Gabriel, A., and Voytas, D. F. (1998) Transposable elements and genome organization: A comprehensive survey of retrotransposons revealed by the complete Saccharomyces cerevisiae genome sequence. Gen. Res. 8: 464-478.

Kobayashi, S., Goto-Yamamoto, N., and Hirochika, H. (2004) Retrotransposon-induced mutations in grape skin color. Science 304: 982.

Latado, R. R., Tognato, P. C., Silva-Stenico, M. E., do Nascimento, L. M., and dos Santos, P. C. (2008) Anthocyanin accumulation and physical and chemical characteristics of blood orange fruits during cold storage. Rev. Bras. Frutic. 30: 604-610.

Lauter, N., Gustus, C., Westerbergh, A., and Doebley, J. (2004) The inheritance and evolution of leaf pigmentation and pubescence in Teosinte. Genetics 167: 1949-1959.

Li, X., Xie, R., Lu, Z., and Zhou, Z. (2010) The origin of cultivated Citrus as inferred from internal transcribed spacer and chloroplast DNA sequence and amplified fragment length polymorphism fingerprints. Journal of the American Society for Horticultural Science 135: 341-350.

Licciardello, C., Russo, M. P., Vale', G., and. Recupero-Reforiato, G. (2008) Identification of differentially expressed genes in the flesh of blood and common oranges. Tree Genet. Genom. 4: 315-331.

Lin-Wang, K., Bolitho, K., Grafton, K., Kortstee, A., Karunairetnam, S., McGhie, T. K., Espley, R. V., Hellens R. P., and Allan, A. C. (2010) An R2R3 MYB transcription factor associated with regulation of the anthocyanin biosynthetic pathway in Rosaceae, BMC Plant Biology 10: 50.

Loytynoja, A., and Goldman, N. (2008) Phylogeny-aware gap placement prevents errors in sequence alignment and evolutionary analysis. Science 320: 1632-1635.

Mabberley, D. J. (1997) A classification of edible citrus (Rutaceae). Telopea 7: 167-172.

Martin, C., Prescott, A., Lister, C., and Mackay, S. (1989) Activity of the transposon Tam3 in *Antirrhinum* and tobacco: possible role of DNA methylation. EMBO J. 8: 997-1004.

McClintock, B. (1984) The significance of responses of the genome to challenge. Science 226: 792-801.

Moore, G. A. (2001) Oranges and lemons: clues to the taxonomy of Citrus from molecular markers. Trends Genet. 17: 536-540.

Negrutiu, I., Shillito, R., Potrykus, I., Biasini, G., and Sala, F. (1987). Hybrid genes in the analysis of transformation conditions. I. Setting up a simple method for direct gene transfer into plant protoplasts. Plant Mol. Biol. 8: 363-373.

Parades-Lopez, O. Cervantes-Ceja, M. L., Vigna-Perez, M., and Hern, andez-Perez, T. (2010) Berries: Improving human health and healthy aging, and promoting quality of life—a review. Plant Foods Hum. Nutr. 65: 299-308.

Parisod, C., Alix, K., Just, J., Petit, M., Sarilar, V., Mhiri, C., Ainouche, M., Chalhoub, M., and Grandbastien, M. A. (2009) The impact of transposable elements on the organization and function of allopolyploid genomes. New Phytol. 186: 37-45.

Pelsey, F. (2010) Molecular and cellular mechanisms of diversity within grapevine varieties. Heredity 104, 331-340.

Prior, R. L., and Wu, X. L. (2006) Anthocyanins: Structural characteristics that result in unique metabolic patterns and biological activities. Free Rad. Res. 40: 1014-1028.

Proteggente A. R., Saija A., De Pasquale A., and Rice-Evans C. A. (2003). The compositional characterisation and antioxidant activity of fresh juices from sicilian sweet orange (*Citrus sinensis* L. Osbeck) varieties. Free Rad. Res. 37: 681-687.

Ramsay, N. A., and Glover, B. J. (2005) MYB-bHLH-WD40 protein complex and the evolution of cellular diversity. Trends Plant Sci. 10: 63-70 (2005).

Rapisada, P., Tomaino, A., lo Cascio, R., Bonina, F., De Pascuale, A., and Saija, A. (1999) Anitoxidant effectiveness as influenced by phenolic content of fresh orange juice. J. Agric. Food Chem. 47: 4718-4723 (1999).

Rapisarda, P., Fabroni, S., Peterek, S., Russo, G., and Mock, H. P. (2009) Juice of new citrus hybrids (*Citrus clementina* Hort. ex Tan.×*C.sinensis* L. Osbeck) as a source of natural antioxidants. Food Chem. 117: 212-218.

Rico-Cabanas, L., and Martinez-Izquierdo, J. A. (2007) CIRE1, a novel transcriptionally active Tyl-copia retrotransposon from *Citrus sinensis*. Mol Genet Genomics 277: 365-77.

Riso, P., Visioli, F., Gardana, C., Gr, ande, S., Brusamolino, A., Galvano, F., Galvano, G., and Parrini, M. (2005) Effects of blood orange juice intake on antioxidant bioavailability and on different markers related to oxidative stress. J. Agric. Food Chem. 53: 941-947.

Schwinn K., Venail, J., Shang, Y. J., Mackay, S., Alm, V., Butelli, E., Oyama, R., Bailey, P., Davies, K., and Martin, C. (2006) A small family of MYB-regulatory genes controls floral pigmentation intensity and patterning in the genus *Antirrhinum*. Plant Cell 18: 831-851.

Shapiro, J. A. (2005) Retrotransposons and regulatory suites. Bioessays 27: 122-125.

Spiegel-Roy, P. (1979) Chimeral nature of the shamouti orange. Euphytica 28: 361-365.

Stracke, R., Werber, M., and Weisshaar, B. (2001) The R2R3-MYB gene family in *Arabidopsis thaliana*. Curr Opin Plant Biol. 4: 447-456.

Takos, A. M., Jaffe, F. W., Jacob, S. R., Bogs, J., Robinson, S. P., and Walker, A. R. (2006) Light-induced expression of a MYB gene regulates anthocyanin biosynthesis in red apples. Plant Physiol. 142: 1216-1232.

Tao, N-G., Xu, J., Cheng, Y-J., Hong, L., Guo, W-W., Yi, H-L., and Deng, X-X. (2005) Isolation and characterization of Copia-like retrotransposons from 12 sweet orange (*Citrus sinensis* Osbeek) cultivars. J. Int. Biol. 47: 1507-1515.

Titta, L., Trinei, M., Stendardo, M., Berniakovich, I., Petroni, K., Tonelli, C., Riso, P., Porrini, M., Minucci, S., Pelicci, P. G., Rapisarda, P., Recupero, G. R., and Giorgio, M. (2010) Blood orange juice inhibits fat accumulation in mice. Int. J. Obesity 34: 578-585.

Toufektsian M. C., de Lorgeril, M., Nagy, N., Salen, P., Donati, M. B., Giordano, L., Mock, H. P., Peterek, S., Matros, A., Petroni, K., Pilu, R., Rotilio, D., Tonelli, C., de Leiris, J., Boucher, F., and Martin, C. (2008) Chronic dietary intake of plant-derived anthocyanins protects the rat heart against ischemia-reperfusion injury. J. Nutr. 138: 747-752.

Walker, A. R., Davison, P. A., Bolognesi-Winfield, A. C., James, C. M., Srinivasan, N., Blundell, T. L., Esch, J. J., Marks, M, D., and Gray, J. C. (1999) The TRANSPARENT TESTA GLABRA1 locus, which regulates trichome differentiation and anthocyanin biosynthesis in *Arabidopsis*, encodes a WD40 repeat protein. Plant Cell 11: 1337-1349.

Walker A. R., Lee, E., Bogs, J., McDavid, D. A. J., Thomas, M. R., and Robinson, S. P. (2007) White grapes arose through the mutation of two similar and adjacent regulatory genes. Plant J. 49: 772-785.

Wessler, S. R. (1996) Plant retrotransposons: Turned on by stress. Curr. Biol. 6: 959-961.

Winkel-Shirley, B. (2001) Flavonoid biosynthesis. A colorful model for genetics, biochemistry, cell biology, and biotechnology. Plant Physiol. 126: 485-493.

Yuan, F., Long, G., and Deng, Z. (2008) Jingxian blood orange: the only pigmented sweet orange cultivar originated in China. Abstracts of the 11th International Citrus Congress, Wuhan.

Zarba, A. S., and Pulvirenti, G. (2006) The consumption of Sicilian red oranges: implications for firms involved in commercialization. J. Business Chemistry 3: 22-41.

Zimmermann, I. M., Heim, M. A., Weisshaar, B., and Uhrig, J. F. (2004) Comprehensive identification of *Arabidopsis thaliana* MYB transcription factors interacting with RIB-like BHLH proteins. Plant J. 40: 22-34.

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for making a plant that is capable of producing a fruit with an increased level of anthocyanins, said method comprising introducing into at least one cell of a plant a heterologous polynucleotide construct, wherein the heterologous polynucleotide construct comprises a promoter operably linked to a nucleotide sequence selected from the group consisting of:
   (a) the full-length coding sequence set forth in SEQ ID NO: 1, 3, 11, or 13;
   (b) a nucleotide sequence encoding the full-length amino acid sequence set forth in SEQ ID NO: 2; and
   (c) a nucleotide sequence encoding an amino acid sequence comprising at least 98% identity to the full-length amino acid sequence set forth in SEQ ID NO: 2; wherein the nucleotide sequence encodes a polypeptide comprising Ruby transcription factor activity;
wherein a fruit produced by the plant comprises an increased level of anthocyanins when compared to a control fruit.

2. The method of claim 1, wherein the promoter drives expression of the operably linked nucleotide sequence in a fruit.

3. The method of claim 2, wherein the promoter comprises the nucleotide sequence set forth in SEQ ID NO: 15.

4. The method of claim 1, wherein the plant is a citrus plant.

5. The method of claim 4, wherein the promoter drives expression of the operably linked nucleotide sequence in the carpels of the fruit.

6. The method of claim 1, further comprising regenerating a plant comprising the polynucleotide construct.

7. The method of claim 6, further comprising growing the plant so as to produce at least one fruit.

8. The method of claim 7, wherein the fruit produced by the plant comprises an increased level of anthocyanins when compared to a control fruit.

9. The method of claim 1, wherein the polynucleotide construct is stably incorporated into the genome of the plant.

10. A transformed plant or plant cell comprising stably incorporated in its genome a heterologous polynucleotide construct, said polynucleotide construct comprising a promoter operably linked to a nucleotide sequence, wherein said nucleotide sequence comprises a member selected from the group consisting of:
    (a) the full-length coding sequence set forth in SEQ ID NO: 1, 3, 11, or 13;
    (b) a nucleotide sequence encoding the full-length amino acid sequence set forth in SEQ ID NO: 2;
    (c) a nucleotide sequence encoding an amino acid sequence comprising at least 98% identity to the full-length amino acid sequence set forth in SEQ ID NO: 2; wherein the nucleotide sequence encodes a polypeptide comprising Ruby transcription factor activity; and
    (d) a nucleotide sequence that is fully complementary to any one of (a)-(c).

11. The plant or plant cell of claim 10, wherein the plant is a citrus plant or the plant cell is a citrus plant cell.

12. The citrus plant of claim 11, wherein the citrus plant is a citrus fruit.

13. A heterologous expression cassette comprising a promoter operably linked to a nucleotide sequence selected from the group consisting of:
    (a) a coding sequence consisting of nucleotides 681-798, 896-1025, and 1821-2358 of SEQ ID NO: 1, nucleotides 1180-1297, 1395-1524, and 2320-2857 of SEQ ID NO: 3, nucleotides 324-1109 of SEQ ID NO: 11, or nucleotides 130-915 of SEQ ID NO: 13, wherein the nucleic acid molecule is a DNA molecule;
    (b) a nucleotide sequence encoding the full-length amino acid sequence set forth in SEQ ID NO: 2, wherein the nucleotide sequence contains at least one deletion, addition, or substitution relative to each of SEQ ID NOS: 1, 3, 11, and 13;
    (c) a nucleotide sequence encoding an amino acid sequence comprising at least 98% identity to the full-length amino acid sequence set forth in SEQ ID NO: 2, wherein the nucleotide sequence encodes a polypeptide comprising Ruby transcription factor activity, and wherein the nucleotide sequence contains at least one deletion, addition, or substitution relative to each of SEQ ID NOS: 1, 3, 11, and 13; and
    (d) a nucleotide sequence that is fully complementary to any one of (a)-(c).

14. A non-human host cell comprising the expression cassette of claim 13.

15. The host cell of claim 14, wherein the host cell is a plant cell.

16. A plant comprising the expression cassette of claim 13.

17. A fruit, a fruit juice, or other food product comprising the expression cassette of claim 13.

18. An expression cassette comprising a heterologous promoter operably linked to a nucleotide sequence, wherein the nucleotide sequence is selected from the group consisting of:
(a) the full-length coding sequence set forth in SEQ ID NO: 1, 3, 11, or 13;
(b) a nucleotide sequence encoding the full-length amino acid sequence set forth in SEQ ID NO: 2; and
(c) a nucleotide sequence encoding an amino acid sequence comprising at least 98% identity to the full-length amino acid sequence set forth in SEQ ID NO: 2, wherein the nucleotide sequence encodes a polypeptide comprising Ruby transcription factor activity.

\* \* \* \* \*

```
                             SEQUENCE LISTING

<160> NUMBER OF SEQ ID NOS: 50

<210> SEQ ID NO 1
<211> LENGTH: 2362
<212> TYPE: DNA
<213> ORGANISM: Citrus sinensis cv. Navel

<400> SEQUENCE: 1
gagagtatac cgtatgcgta cacatcaata ttgatactag ctagatagct aggttggtcc      60
ctggctatag ctattaaaaa aaaaaaaaag ttatgtgctt aattattgcc accaaaagag     120
tcattgggct ggaagttagt tggagaaaat attgtacaga aaaaaaaaaa aaaacgatg      180 gagtttgggc ttgagttctc attgcgtccc cttggcggga agcactgtac aagaactta      240 ggccgttcaa aactttaatt atcacacggc atttttttt tttttttta atagctgtag      300 ccagggacat ctggagtttg atgaaagaca ctcaatattc aacagataag cattagacgc     360
acttgttttt tctgtttcaa cttgttaatg gttttgggaa ttgttaactt ggactggtag     420
ttgtaattaa caagtattgt ttactatttt tggacgaaga atagtagaag tagtttcctt     480
gtggatgcaa gacaagcacg tcactctctc cgaaaaggct taattgatcg acgtagcatg     540
aagtgaggag cacgtattat tatacaagca gctgttctgt aggctcttta aattttataa     600
aaaaagagag ttgagtaagt gtaggtgcta attaaattt gatttttag gtaagcacat       660 atactacaca tagggtcttt atggcggatt ccttaggagt tcgtaaaggt gcatggacag     720
gagaggaaga tgatcttctt aggaaatgca ttgagaaata tggggaagca aaatggcatc     780
aagttcctct aagagcaggt aaatagtttc agtactattt caagtagttt tcacaggagc     840
tgcttctatt tatgcaattt caacagttta tattctctct tttgaacaat ttcaggattg     900
catcgatgcc ggaaaagctg tagactgcgg tggctgaact atctcaaccc gaatatcaaa     960
cgaggagaat ttgcagcaga tgaagttgat ttaattttaa ggctccataa gctgctgggc    1020
aacaggcaag tgcagaaagt agaacggaag ccgaactgag gctccgttta gtattaccgt    1080
ctaccagcgg tgacttttaa ttaagccatt tcaacaaaca cttataacta ttatttggga    1140
gttaatcata gttatttta ctccacatta atttgatgag acacctatat tccttttatt     1200
atcttgtcca aatatatgat taacattaaa ttttaatcat gtagatcgaa cactatagga    1260
aaatatacta attggagtaa agagaaacta aaagggtggt ccaatagcta cgtgtgcata    1320
ttggttgagc aacatatagc atacacataa actaccccat catctaacaa aacacttgtc    1380
acaaagtttt cgcaaattag aactcttact atattagcag attttctttt tcgtggcatg    1440
tacatagggt tacaggttgt aggccggaat taaataggaa ttaatcagaa atttatgatg    1500
tacttttcag ggaatggtga catgttagac ctttcaaatt cagcctttta caataacacg    1560
acgatggatg gttatccaat tattaatttc tattctttaa tttcttatta ttcgaatatg    1620
gatggttatc caacctctcg gccacccttt taaagctgca gaatatatat ttaagtagta    1680
ctaaacttac aaaattatga cacagaattt gtaacaggat gtgggttcaa ctttactttt    1740
attataaatt atcgttttgt cccttttttg ttggcaaaat gcaattctga tatactgtaa    1800
tttggttgaa ttgcatgtag atggtcactg attgtgggca ggcttccggg aagaacagcg    1860
```

```
aacgatgtga agaattttg gaacacgcac ctgcgcaaga agtggataaa atgctgcaag    1920
aataataaag agatgaaagc aaaagctgag aaggtggaaa agatcaatat cataaaacct    1980
caacctcgga ccttcgctaa aaactcacaa tggttgaagg gcaagggaat gacttcaaat    2040
aatttgcaat taggagatta caatctcggc aaacaatcca ccccgtctga tcatcatcat    2100
catcatcaac agcagcagga gaatgaaact gaatctgtat ggtgggaaag cttttattc     2160 ggagatgaat tggatcaaca aggaatttca agctcattga gtcggccaga agaggaatct    2220
actacggcaa atattttgc cgaaaagtct ccagtagtga caaaggtgac agaaaataga    2280
gtcattgaag caggccagag ttgtccgact gatgacttcg ctttcgacgc ggaactttgg    2340
gatcttctca atgcaaagta ag                                              2362
```

<210> SEQ ID NO 2
<211> LENGTH: 262
<212> TYPE: PRT
<213> ORGANISM: Citrus sinensis cv. Navel

<400> SEQUENCE: 2

```
Met Ala Asp Ser Leu Gly Val Arg Lys Gly Ala Trp Thr Gly Glu Glu
  1               5                  10                  15

Asp Asp Leu Leu Arg Lys Cys Ile Glu Lys Tyr Gly Glu Ala Lys Trp
             20                  25                  30

His Gln Val Pro Leu Arg Ala Gly Leu His Arg Cys Arg Lys Ser Cys
         35                  40                  45

Arg Leu Arg Trp Leu Asn Tyr Leu Asn Pro Asn Ile Lys Arg Gly Glu
     50                  55                  60

Phe Ala Ala Asp Glu Val Asp Leu Ile Leu Arg Leu His Lys Leu Leu
 65                  70                  75                  80

Gly Asn Arg Trp Ser Leu Ile Val Gly Arg Leu Pro Gly Arg Thr Ala
                 85                  90                  95

Asn Asp Val Lys Asn Phe Trp Asn Thr His Leu Arg Lys Lys Val Asp
            100                 105                 110

Lys Cys Cys Lys Asn Asn Lys Glu Met Lys Ala Lys Ala Glu Lys Val
        115                 120                 125

Glu Lys Ile Asn Ile Ile Lys Pro Gln Pro Arg Thr Phe Ala Lys Asn
    130                 135                 140

Ser Gln Trp Leu Lys Gly Lys Gly Met Thr Ser Asn Asn Leu Gln Leu
145                 150                 155                 160

Gly Asp Tyr Asn Leu Gly Lys Gln Ser Thr Pro Ser Asp His His His
                165                 170                 175

His His Gln Gln Gln Gln Glu Asn Glu Thr Glu Ser Val Trp Trp Glu
            180                 185                 190

Ser Phe Leu Phe Gly Asp Glu Leu Asp Gln Gln Gly Ile Ser Ser Ser
        195                 200                 205

Leu Ser Arg Pro Glu Glu Glu Ser Thr Thr Ala Asn Ile Phe Ala Glu
    210                 215                 220

Lys Ser Pro Val Val Thr Lys Val Thr Glu Asn Arg Val Ile Glu Ala
225                 230                 235                 240

Gly Gln Ser Cys Pro Thr Asp Asp Phe Ala Phe Asp Ala Glu Leu Trp
                245                 250                 255

Asp Leu Leu Asn Ala Lys
            260
```

<210> SEQ ID NO 3

```
<211> LENGTH: 2861
<212> TYPE: DNA
<213> ORGANISM: Citrus sinensis cv. Moro

<400> SEQUENCE: 3
gagagtatac cgtatgcgta cacatcaata ttgatactag ctagatagct aggttggtcc      60
ctggctatag ctattaaaaa aaaaaaaagt tatgtgctta attattgcca ccaaaagagt     120
cattgggctg gaagttagtt ggagaaaata ttgtacagaa aaaaaaaaaa aaaacgatgg     180
agtttgggct tgagttctca ttgcgtcccc ttggcgggaa gcactgtaca agaactttag     240
gccgttcaaa actttaatta tcacacggca ttttttttt tttttttaat agctgtagcc      300
agggacatct ggagtttgat gaaagacact caatattcaa cagataagca ttagacgcac     360
ttgttttttc tgtttcaact tgttaatggt tttgggaatt gttaacttgg actggtagtt     420
gtaattaact gtcaaagtcg gtggccacaa ggcaaattca agttggcttt gacaagccgg     480
ccaaagaaaa tggtgcagcc ggccaaagaa aatggtgccg tccaaatgga gaaaagaag      540 aagttggcaa caacatttga aatatgtata tattatttta attaccatt tttggctata      600 aaagggagaa ctccctaatt catttatcat ccaattttgt agagagaatt gagagttgtg     660
agaagtgatt cttgcaagag caaagaattt tgtgtgctta gtgatttgag agtttgggtg     720
tattggggtt ttgggtagtg agctaaaata ctacaatact tgtaactcct tttcactagt     780
ataatatttc tttctgtctt cgcccgtgga cgtaggctaa aagccgaacc acgtaatttc     840 tggtatttc ttttgtgctt gttctttatt tttctatcaa ttttacttta gctgcgtgtc      900
tgcttcaccc accaatttcc taacattaac aagtattgtt tactatttt ggacgaagaa      960 tagtagaagt agtttccttg tggatgcaag acaagcacgt cactctctcc gaaaaggctt    1020
aattgatcga cgtagcatga agtgaggagc acgtattatt atacaagcag ctgttctgta    1080
ggctctttaa attttataaa aaaagagagt tgagtaagtg taggtgctaa ttaaattttg    1140
attttttagg taagcacata tactacacat agggtctta tggcggattc cttaggagtt    1200
cgtaaaggtg catggacagg agaggaagat gatcttctta ggaaatgcat tgagaaatat    1260
ggggaagcaa aatggcatca agttcctcta agagcaggta aatagtttca gtactatttc    1320
aagtagtttt cacaggagct gcttctattt atgcaatttc aacagtttat attctctctt    1380
ttgaacaatt tcaggattgc atcgatgccg gaaaagctgt agactgcggt ggctgaacta    1440
tctcaacccg aatatcaaac gaggagaatt tgcagcagat gaagttgatt taattttaag    1500
gctccataag ctgctgggca acaggcaagt gcagaaagta gaacggaagc cgaactgagg    1560
ctccgtttag tattaccgtc taccagcggt gacttttaat taagccattt caacaaacac    1620
ttataactat tatttgggag ttaatcatag ttattttac tccacattaa tttgatgaga    1680
cacctatatt cctttatta tcttgtccaa atatatgatt aacattaaat tttaatcatg    1740
tagatcgaac actataggaa aatatactaa ttggagtaaa gagaaactaa aagggtggtc    1800
caatagctac gtgtgcatat tggttgagca acatatagca tacacataaa ctaccccatc    1860
atctaacaaa acacttgtca caaagttttc gcaaattaga actcttacta tattagcaga    1920
ttttctcttt cgtggcatgt acataggggtt acaggttgta ggccggaatt aaataggaat    1980
taatcagaaa tttatgatgt acttttcagg gaatggtgac atgttagacc tttcaaattc    2040
agccttttac aataacacga cgatggatgg ttatccaatt attaatttct attctttaat    2100
ttcttattat tcgaatatgg atggttatcc aacctctcgg ccacccttt aaagctgcag    2160 aatatatatt taagtagtac taaacttaca aaattatgac acagaatttg taacaggatg    2220
```

```
tgggttcaac tttactttta ttataaatta tcgttttgtc cctttttgt tggcaaaatg    2280 caattctgat atactgtaat ttggttgaat tgcatgtaga tggtcactga ttgtgggcag    2340
gcttccggga agaacagcga acgatgtgaa gaattttgg aacacgcacc tgcgcaagaa    2400
agtggataaa tgctgcaaga ataataaaga gatgaaagca aaagctgaga aggtggaaaa    2460
gatcaatatc ataaaacctc aacctcggac cttcgctaaa aactcacaat ggttgaaggg    2520
caagggaatg acttcaaata atttgcaatt aggagattac aatctcggca acaatccac    2580 cccgtctgat catcatcatc atcatcaaca gcagcaggag aatgaaactg aatctgtatg    2640
gtgggaaagc tttttattcg gagatgaatt ggatcaacaa ggaatttcaa gctcattgag    2700
tcggccagaa gaggaatcta ctacggcaaa tattttgcc gaaaagtctc cagtagtgac    2760
aaaggtgaca gaaaatagag tcattgaagc aggccagagt tgtccgactg atgacttcgc    2820
tttcgacgcg gaactttggg atcttctcaa tgcaaagtaa g    2861
```

<210> SEQ ID NO 4
<211> LENGTH: 262
<212> TYPE: PRT
<213> ORGANISM: Citrus sinensis cv. Moro

<400> SEQUENCE: 4

```
Met Ala Asp Ser Leu Gly Val Arg Lys Gly Ala Trp Thr Gly Glu Glu
  1               5                  10                  15

Asp Asp Leu Leu Arg Lys Cys Ile Glu Lys Tyr Gly Glu Ala Lys Trp
                 20                  25                  30

His Gln Val Pro Leu Arg Ala Gly Leu His Arg Cys Arg Lys Ser Cys
             35                  40                  45

Arg Leu Arg Trp Leu Asn Tyr Leu Asn Pro Asn Ile Lys Arg Gly Glu
         50                  55                  60

Phe Ala Ala Asp Glu Val Asp Leu Ile Leu Arg Leu His Lys Leu Leu
 65                  70                  75                  80

Gly Asn Arg Trp Ser Leu Ile Val Gly Arg Leu Pro Gly Arg Thr Ala
                 85                  90                  95

Asn Asp Val Lys Asn Phe Trp Asn Thr His Leu Arg Lys Lys Val Asp
            100                 105                 110

Lys Cys Cys Lys Asn Asn Lys Glu Met Lys Ala Lys Ala Glu Lys Val
        115                 120                 125

Glu Lys Ile Asn Ile Ile Lys Pro Gln Pro Arg Thr Phe Ala Lys Asn
    130                 135                 140

Ser Gln Trp Leu Lys Gly Lys Gly Met Thr Ser Asn Asn Leu Gln Leu
145                 150                 155                 160

Gly Asp Tyr Asn Leu Gly Lys Gln Ser Thr Pro Ser Asp His His His
                165                 170                 175

His His Gln Gln Gln Gln Glu Asn Glu Thr Glu Ser Val Trp Trp Glu
            180                 185                 190

Ser Phe Leu Phe Gly Asp Glu Leu Asp Gln Gln Gly Ile Ser Ser Ser
        195                 200                 205

Leu Ser Arg Pro Glu Glu Glu Ser Thr Thr Ala Asn Ile Phe Ala Glu
    210                 215                 220

Lys Ser Pro Val Val Thr Lys Val Thr Glu Asn Arg Val Ile Glu Ala
225                 230                 235                 240

Gly Gln Ser Cys Pro Thr Asp Asp Phe Ala Phe Asp Ala Glu Leu Trp
                245                 250                 255
```

Asp Leu Leu Asn Ala Lys
        260

<210> SEQ ID NO 5
<211> LENGTH: 878
<212> TYPE: DNA
<213> ORGANISM: Citrus sinensis x Citrus reticulata cv. OTA7

<400> SEQUENCE: 5

```
accttatcga cagataacat tatgacaatc ttattggttg acctcttgag tcttgatctg      60
agatcaagga ataagagtgt tgtgagact gtttgtttta agaggcaagt ataatttgga     120
gtgggaaaat gtggaatgca atatgtaatt aaaacaaata aatttaaaat atgcaaggaa    180
ctaactcgga tacatccaat ttgcggttgg gtgggtaaag acgtaggtga agtgtactgt    240
aacttgaaaa aagaaattaa aaagaagtt attatatttt tcttaataaa ttgattgtat     300
aatgataata actatagaat tgagcaacat gtgcatattg gttgagcaac atatagcata    360
cgcataaact accccatcat ctaacaaaac acttgtcaca agttttcgt aaaatagaac     420
tcttactata ttagcagact tttcttttcg tggcatgtac ataggtttac aggttgtagg    480
ccggaattaa ataggaatta atcagaaatt tatgatgtac ttttcaggga atggtgacat   540
gttagacctt tcaaattcag cctttacaa taacacgacg atggatggtt atccagttat    600
taatttctat tctttaattt cttcttattc gaatatggat ggttatccaa cctctcggcc    660
acccttttaa agctgcagaa tatatatcta agtagtacta aacttacaaa attatgacac   720
tgaatttgta acaggatgtg ggttcaactt tacttttatt ataaattatc gttttgtccc   780
ttttttgttg gcaaaatgca attctgatat actgtaattt ggttgaattg catgtagatg   840
gtcactgatt gtgggcaggc ttccgggaag aacagcga                           878
```

<210> SEQ ID NO 6
<211> LENGTH: 180
<212> TYPE: PRT
<213> ORGANISM: Citrus sinensis x Citrus reticulata cv. OTA7

<400> SEQUENCE: 6

Arg Trp Ser Leu Ile Val Gly Arg Leu Pro Gly Arg Thr Ala Asn Asp
 1               5                  10                  15

Val Lys Asn Phe Trp Asn Thr His Leu Arg Lys Lys Val Asp Lys Cys
            20                  25                  30

Cys Lys Asn Asn Lys Glu Met Lys Ala Lys Ala Glu Lys Val Glu Lys
        35                  40                  45

Ile Asn Ile Ile Lys Pro Gln Pro Arg Thr Phe Ala Lys Asn Ser Gln
    50                  55                  60

Trp Leu Lys Gly Lys Gly Met Thr Ser Asn Asn Leu Gln Leu Gly Asp
65                  70                  75                  80

Tyr Asn Leu Gly Lys Gln Ser Thr Pro Ser Asp His His His His
                85                  90                  95

Gln Gln Gln Gln Glu Asn Glu Thr Glu Ser Val Trp Trp Glu Ser Phe
            100                 105                 110

Leu Phe Gly Asp Glu Leu Asp Gln Gln Gly Ile Ser Ser Ser Leu Ser
        115                 120                 125

Arg Pro Glu Glu Glu Ser Thr Thr Ala Asn Ile Phe Ala Glu Lys Ser
    130                 135                 140

Pro Val Val Thr Lys Val Thr Glu Asn Arg Val Ile Glu Ala Gly Gln
145                 150                 155                 160

Ser Cys Pro Thr Asp Asp Phe Ala Phe Asp Ala Glu Leu Trp Asp Leu
                165                 170                 175

Leu Asn Ala Lys
        180

<210> SEQ ID NO 7
<211> LENGTH: 5413
<212> TYPE: DNA
<213> ORGANISM: Citrus sinensis cv. Tarocco

<400> SEQUENCE: 7

| | | | | | |
|---|---|---|---|---|---|
| tgtcaaagtc | ggtggccaca | aggcaaattc | aagttggctt | tgacaagccg | gccaaagaaa | 60 |
| atggtgcagc | cggccaaaga | aaatggtgcc | gtccaaatgg | agaaaaagaa | gaagttggca | 120 |
| acaacatttg | aaatatgtat | atattatttt | aattaccatt | ttttggctat | aaaagggaga | 180 |
| actccctaat | tcatttatca | tccaattttg | tagagagaat | tgagagttgt | gagaagtgat | 240 |
| tcttgcaaga | gcaaagaatt | ttgtgtgctt | agtgatttga | gagtttgggt | gtattggggt | 300 |
| tttgggtagt | gagctaaaat | actacaatac | ttgtaactcc | ttttcactag | tataatattt | 360 |
| ctttctgtct | tcgcccgtgg | acgtaggcta | aaagccgaac | cacgtaattt | ctggtatttt | 420 |
| cttttgtgct | tgttctttat | ttttctatca | attttacttt | agctgcgtgt | ctgcttcacc | 480 |
| caccaatttc | ctaacagtgg | tatcagagct | attggttgta | ttttggagt | caggaactgt | 540 |
| tcacgtaagg | ggtactattc | acgtatacgg | caccgtacac | gtatacgta | ctgttcatgt | 600 |
| acacggtgtt | gttcacatag | actgaactat | tcacgtatac | ggtactattc | acgtgaagcg | 660 |
| gtggaagcga | tccaagaatt | tgcggtgca | agcagggaa | tagtggtgtg | agtaaagcaa | 720 |
| ctgtgtggtt | tgtacatgt | ctaggaaagt | tctgtcacaa | aggcgataag | agcttaagga | 780 |
| gtctgggttt | taagtgggac | cattgtgacc | cctccagtct | ttcctgggaa | ctttcctggt | 840 |
| gtgcattctt | acacatactc | acaactattc | aaggtggtat | acttgcttgt | gtgcagtatt | 900 |
| tatcaacaaa | atggcggcaa | agtatgaaat | tgagaaattt | aacggaaata | attttttcgtt | 960 |
| gtggaaaatg | aagatgaaag | ctgtattgag | gaaaaataat | tgcttggcag | caattggaga | 1020 |
| aagacccatg | gagataactg | atgacaagtg | gaacgaggta | gacggcaacg | ccatttctga | 1080 |
| tctacacttg | gcacttgcag | acggagtatt | atccagtgtg | gcagagaaaa | acacagcgaa | 1140 |
| ggaaatatgg | gatactctca | caaaattgta | tgaggccaag | tcactacaca | acaaaatctt | 1200 |
| cttgaagaga | aaactctata | ctcttcgaat | ggcagaatct | acaatggtga | ccgaccacat | 1260 |
| caacacattg | aagactctat | tttcacaact | cacaacgttg | ggtcataata | tagaggaaaa | 1320 |
| tgaacgtgca | gagcttctac | ttcaaagtct | accagattcg | tatgatcaac | tcatcatcaa | 1380 |
| cctaacgaac | aacaatccag | tggagagtct | agttttcgac | gatgttgcag | cctccgtatt | 1440 |
| aaatgaggag | agcaggcgga | aaaataagga | aaacagacaa | gcaagttcgc | agcaagcgga | 1500 |
| ggcgctatca | gtgacgagag | ggagatcaac | ggaacgtggc | cccagtggga | gtcaaaatca | 1560 |
| gggtagatca | aaattcagag | gtaagaagaa | tgttaaatgc | tacaactgtg | gcaagaaagg | 1620 |
| gcacgttaag | aaagaatgtt | ggagtaacca | gaagagaaga | gagggcaaag | aacctgagac | 1680 |
| atcaaatgct | caggggtgtg | tagcaagtac | ctcggatgat | ggcgaaattc | tctacagtga | 1740 |
| ggcaacaact | gtttcagaag | gcagaaaacg | actttctgat | gtctggctta | tagactcagg | 1800 |
| agctacctgg | cacatgacct | ctaggagaga | atggttccac | acatatgaac | ctatctcagg | 1860 |
| aggatctgta | tatatgggta | acgatcatgc | cttggagatc | gctggtattg | gtactatcaa | 1920 |
| aataaaaatg | tttgatggta | caattcgcac | aattggagag | gtacgacatg | tcaacggcct | 1980 |

```
gaagaaaaat ctattgtctt tgggacaaat ggatagtcat gggtacaaaa ctcatgtgga    2040
gaatggaatt atgaagatcg ttaaaggcgc gcttgtattg atgaaggtag aaaagatcgg    2100
tgctaatcta ttcatgctta aaggagaaac actacaggag gctgatgcgt gtgtcgcatc    2160
aaatggagaa gagtcaacga tgatgtggca tctcaaactt ggccacatgt cggaacaagg    2220
tttgaagatt ctctctgagc gaaaattgct tccagggctc aaatcggtaa gtttaccatt    2280
ttgcgagcat tgtgttacaa gtaagcagca tagattaaaa ttcagtagat ctattgctag    2340
aagtaaatgc attctcgact tgattcattc tgatgtttgg gaatcaccgg atatatccat    2400
gggaggtgca aagtacatgg tgactttcat tgatgattat tccagaagat gttgggtgta    2460
tccaattaag aaaaagtcag atgtatttcc tgtgtttaaa gaatacaaag cgtgggtgga    2520
acttgaatct ggtaaaaaga tcaagtgctt gaggacagat aatggtggag aatatacaga    2580
cggcgagttt cttgctttct gtaagcaaga aggtattcag agacagttca cggtggcata    2640
cactcctcaa caaaatggag tggcagaacg atgaacaga actcttacag aaagaataag    2700
agctatgttg aggactgctg gtctacccaa ttcattctgg gcagaagcag ccaaaactgc    2760
ctgttatata gtaaatcggt cgccatctac agctattggg ttgaagacag cgatggagat    2820
gtggactgga aagccagctg attattccta cctacatgca tttggatgtc ctatgtacgt    2880
gatgtacaat gcccaagaaa gaacaaagct ggatgcaaaa tctagaagat gtatcttctt    2940
ggggtatgct gatggagtaa aggggtatcg tctgtgggac cccactgccc ataagatcgt    3000
catcagcaga gatgttatct ttgtagaaga tcaactgcaa agaaaagatg gagatgatgg    3060
cactgtaaaa gaaaagtctg agactgtgcc agtatatgtc gaaaataatc cagaaaattc    3120
agattcttct gaagcagcac cagagcacga ggaacaagaa ccagttgagt ccgaggctcc    3180
agaagttcgt cggtcaactc gtgagagacg accgccaacg tggcactcgg agtatgtcac    3240
agagatcaat gttgcatact gtcttctaac agaggatgga gagccttcaa ctttccatga    3300
agctttaaac agttcagatg ttgctttgtg gatgacagca atgcaggaag aaattgaagc    3360
tctacacaag aacaagacat gggaacttgt accactacca cgtggaagaa aagccattgg    3420
aaacaaatgg gtctacaaga tcaaacgtga tggtaatgac caagtggagc ggtatcgtgc    3480
gagattggtg gtgaaaggat atgctcagaa agaaggtatt gacttcaatg agatattttc    3540
tccggtggtt cgactcacaa cagtcagaat agtcttggca atgtgtgcca catttgacct    3600
acatctagag cagttagatg tgaaaactgc atttcttcat ggagaacttg aagaagaaat    3660
atatatgctc caaccagaag gttttgcaga aacaggaaag gagaacttgg tttgcaggtt    3720
gaacaaatct ctatacggtc tcaaacaggc gccgaggtat tggtataaga gatttgattc    3780
cttcattatg agccttggat acaacagact cagttcagac cattgtgcat attacaagag    3840
gtttgaagat aatgatttca tcattttgct gttgtatgtg gatgacatgt tggtagcagg    3900
tcccaataaa gatcgaatcc aagaattgaa ggcacagttg gctagggagt ttgaaatgaa    3960
ggacttggga ccagcaaaca agattctagg gatgcaaatt caccgagaca gaaataacat    4020
gaagatttgg ctttcgcaga agaattattt gaagaaaatc ttgcggcgct tcaacatgca    4080
agattgtaag tcaatttcta cctcacttcc tgttaatttc aaattatcct caagtatgtg    4140
tcctagcaat gaagcggaga ggaaggagat gtctcgagta ccgtatgcat cagcagtggg    4200
aagtttgatg ttcgctatga tatgtactag accggacatt gcacaagcag tgggagtagt    4260
cagtcgatac atggcgaatc ctggtggaga gcattggata gctgtgaaaa ggattctgag    4320
```

-continued

```
atacatcaga ggaacctcag atgttgcatt atgttatgga ggatcagagt ttactgtcag    4380
gggttatgtg gattcagatt ttgcaggaga tcttgataaa agaaaatcca ctactggtta    4440
tgtgtttaca cttgcgggag cagctgtaag ctgggtttcg aaactgcaga ccgttgtggc    4500
tttatctaca acagaagcag aatacatggc agctacacaa gcttgcaaga aagctatttg    4560
gatacaaagg ttattggagg agctcgggca caaacaacag aaaattcttg tgttttgtga    4620
cagtcagagt gccttgcaca ttgcaaggaa tccagccttt cattccagga caaagcacat    4680
aggagttcag tatcacttcg ttcgtgaagt agtggaagat ggaagtgtgg atttgcagaa    4740
aatccatacc aaagagaacc tagcagatgt tttgaccaag ccgataaaata ctgataagtt    4800
tgtctggagt agatcctctt gtggcctagc agaaacgtag gcaacatgat tatggcgaag    4860
cagaaaggat gatgtggaga ttgattgatt ctcaatcaaa tctccaagtg ggagaaatgt    4920
caaagtcggt ggccacaagg caaattcaag ttggctttga caagccggcc aaagaaaatg    4980
gtgcagccgg ccaaagaaaa tggtgccgtc caaatggaga aaagaagaa gttggcaaca    5040
acatttgaaa tatgtatata ttattttaat taccattttt tggctataaa agggagaact    5100
ccctaattca tttatcatcc aattttgtag agagaattga gagttgtgag aagtgattct    5160
tgcaagagca aagaattttg tgtgcttagt gatttgagag tttgggtgta ttggggtttt    5220
gggtagtgag ctaaaatact acaatacttg taactccttt tcactagtat aatatttctt    5280
tctgtcttcg cccgtggacg taggctaaaa gccgaaccac gtaatttctg gtattttctt    5340
ttgtgcttgt tctttatttt tctatcaatt ttactttagc tgcgtgtctg cttcacccac    5400
caatttccta aca                                                       5413
```

<210> SEQ ID NO 8
<211> LENGTH: 1309
<212> TYPE: PRT
<213> ORGANISM: Citrus sinensis cv. Tarocco

<400> SEQUENCE: 8

```
Met Ala Ala Lys Tyr Glu Ile Glu Lys Phe Asn Gly Asn Asn Phe Ser
1               5                   10                  15

Leu Trp Lys Met Lys Met Lys Ala Val Leu Arg Lys Asn Asn Cys Leu
            20                  25                  30

Ala Ala Ile Gly Glu Arg Pro Met Glu Ile Thr Asp Asp Lys Trp Asn
        35                  40                  45

Glu Val Asp Gly Asn Ala Ile Ser Asp Leu His Leu Ala Leu Ala Asp
    50                  55                  60

Gly Val Leu Ser Ser Val Ala Glu Lys Asn Thr Ala Lys Glu Ile Trp
65                  70                  75                  80

Asp Thr Leu Thr Lys Leu Tyr Glu Ala Lys Ser Leu His Asn Lys Ile
                85                  90                  95

Phe Leu Lys Arg Lys Leu Tyr Thr Leu Arg Met Ala Glu Ser Thr Met
            100                 105                 110

Val Thr Asp His Ile Asn Thr Leu Lys Thr Leu Phe Ser Gln Leu Thr
        115                 120                 125

Thr Leu Gly His Asn Ile Glu Glu Asn Glu Arg Ala Glu Leu Leu Leu
    130                 135                 140

Gln Ser Leu Pro Asp Ser Tyr Asp Gln Leu Ile Ile Asn Leu Thr Asn
145                 150                 155                 160

Asn Asn Pro Val Glu Ser Leu Val Phe Asp Asp Val Ala Ala Ser Val
                165                 170                 175
```

-continued

```
Leu Asn Glu Glu Ser Arg Arg Lys Asn Lys Glu Asn Arg Gln Ala Ser
            180                 185                 190
Ser Gln Gln Ala Glu Ala Leu Ser Val Thr Arg Gly Arg Ser Thr Glu
        195                 200                 205
Arg Gly Pro Ser Gly Ser Gln Asn Gln Gly Arg Ser Lys Phe Arg Gly
    210                 215                 220
Lys Lys Asn Val Lys Cys Tyr Asn Cys Gly Lys Lys Gly His Val Lys
225                 230                 235                 240
Lys Glu Cys Trp Ser Asn Gln Lys Arg Arg Glu Gly Lys Glu Pro Glu
                245                 250                 255
Thr Ser Asn Ala Gln Gly Cys Val Ala Ser Thr Ser Asp Asp Gly Glu
            260                 265                 270
Ile Leu Tyr Ser Glu Ala Thr Thr Val Ser Glu Gly Arg Lys Arg Leu
        275                 280                 285
Ser Asp Val Trp Leu Ile Asp Ser Gly Ala Thr Trp His Met Thr Ser
    290                 295                 300
Arg Arg Glu Trp Phe His Thr Tyr Glu Pro Ile Ser Gly Gly Ser Val
305                 310                 315                 320
Tyr Met Gly Asn Asp His Ala Leu Glu Ile Ala Gly Ile Gly Thr Ile
                325                 330                 335
Lys Ile Lys Met Phe Asp Gly Thr Ile Arg Thr Ile Gly Glu Val Arg
            340                 345                 350
His Val Asn Gly Leu Lys Lys Asn Leu Leu Ser Leu Gly Gln Met Asp
        355                 360                 365
Ser His Gly Tyr Lys Thr His Val Glu Asn Gly Ile Met Lys Ile Val
    370                 375                 380
Lys Gly Ala Leu Val Leu Met Lys Val Glu Lys Ile Gly Ala Asn Leu
385                 390                 395                 400
Phe Met Leu Lys Gly Glu Thr Leu Gln Glu Ala Asp Ala Cys Val Ala
                405                 410                 415
Ser Asn Gly Glu Glu Ser Thr Met Met Trp His Leu Lys Leu Gly His
            420                 425                 430
Met Ser Glu Gln Gly Leu Lys Ile Leu Ser Glu Arg Lys Leu Leu Pro
        435                 440                 445
Gly Leu Lys Ser Val Ser Leu Pro Phe Cys Glu His Cys Val Thr Ser
    450                 455                 460
Lys Gln His Arg Leu Lys Phe Ser Arg Ser Ile Ala Arg Ser Lys Cys
465                 470                 475                 480
Ile Leu Asp Leu Ile His Ser Asp Val Trp Glu Ser Pro Asp Ile Ser
                485                 490                 495
Met Gly Gly Ala Lys Tyr Met Val Thr Phe Ile Asp Asp Tyr Ser Arg
            500                 505                 510
Arg Cys Trp Val Tyr Pro Ile Lys Lys Lys Ser Asp Val Phe Pro Val
        515                 520                 525
Phe Lys Glu Tyr Lys Ala Trp Val Glu Leu Glu Ser Gly Lys Lys Ile
    530                 535                 540
Lys Cys Leu Arg Thr Asp Asn Gly Gly Glu Tyr Thr Asp Gly Glu Phe
545                 550                 555                 560
Leu Ala Phe Cys Lys Gln Glu Gly Ile Gln Arg Gln Phe Thr Val Ala
                565                 570                 575
Tyr Thr Pro Gln Gln Asn Gly Val Ala Glu Arg Met Asn Arg Thr Leu
            580                 585                 590
Thr Glu Arg Ile Arg Ala Met Leu Arg Thr Ala Gly Leu Pro Asn Ser
```

```
                595                 600                 605
    Phe Trp Ala Glu Ala Ala Lys Thr Ala Cys Tyr Ile Val Asn Arg Ser
    610                 615                 620
    Pro Ser Thr Ala Ile Gly Leu Lys Thr Ala Met Glu Met Trp Thr Gly
625                 630                 635                 640
    Lys Pro Ala Asp Tyr Ser Tyr Leu His Ala Phe Gly Cys Pro Met Tyr
                645                 650                 655
    Val Met Tyr Asn Ala Gln Glu Arg Thr Lys Leu Asp Ala Lys Ser Arg
                660                 665                 670
    Arg Cys Ile Phe Leu Gly Tyr Ala Asp Gly Val Lys Gly Tyr Arg Leu
                675                 680                 685
    Trp Asp Pro Thr Ala His Lys Ile Val Ile Ser Arg Asp Val Ile Phe
            690                 695                 700
    Val Glu Asp Gln Leu Gln Arg Lys Asp Gly Asp Gly Thr Val Lys
705                 710                 715                 720
    Glu Lys Ser Glu Thr Val Pro Val Tyr Val Glu Asn Asn Pro Glu Asn
                        725                 730                 735
    Ser Asp Ser Ser Glu Ala Ala Pro Glu His Glu Glu Gln Glu Pro Val
                740                 745                 750
    Glu Ser Glu Ala Pro Glu Val Arg Arg Ser Thr Arg Glu Arg Arg Pro
                755                 760                 765
    Pro Thr Trp His Ser Glu Tyr Val Thr Glu Ile Asn Val Ala Tyr Cys
770                 775                 780
    Leu Leu Thr Glu Asp Gly Glu Pro Ser Thr Phe His Glu Ala Leu Asn
785                 790                 795                 800
    Ser Ser Asp Val Ala Leu Trp Met Thr Ala Met Gln Glu Glu Ile Glu
                        805                 810                 815
    Ala Leu His Lys Asn Lys Thr Trp Glu Leu Val Pro Leu Pro Arg Gly
                820                 825                 830
    Arg Lys Ala Ile Gly Asn Lys Trp Val Tyr Lys Ile Lys Arg Asp Gly
                835                 840                 845
    Asn Asp Gln Val Glu Arg Tyr Arg Ala Arg Leu Val Val Lys Gly Tyr
                850                 855                 860
    Ala Gln Lys Glu Gly Ile Asp Phe Asn Glu Ile Phe Ser Pro Val Val
865                 870                 875                 880
    Arg Leu Thr Thr Val Arg Ile Val Leu Ala Met Cys Ala Thr Phe Asp
                        885                 890                 895
    Leu His Leu Glu Gln Leu Asp Val Lys Thr Ala Phe Leu His Gly Glu
                        900                 905                 910
    Leu Glu Glu Glu Ile Tyr Met Leu Gln Pro Glu Gly Phe Ala Glu Thr
                915                 920                 925
    Gly Lys Glu Asn Leu Val Cys Arg Leu Asn Lys Ser Leu Tyr Gly Leu
930                 935                 940
    Lys Gln Ala Pro Arg Tyr Trp Tyr Lys Arg Phe Asp Ser Phe Ile Met
945                 950                 955                 960
    Ser Leu Gly Tyr Asn Arg Leu Ser Ser Asp His Cys Ala Tyr Tyr Lys
                        965                 970                 975
    Arg Phe Glu Asp Asn Asp Phe Ile Ile Leu Leu Leu Tyr Val Asp Asp
                980                 985                 990
    Met Leu Val Ala Gly Pro Asn Lys Asp Arg Ile Gln Glu Leu Lys Ala
                995                 1000                1005
    Gln Leu Ala Arg Glu Phe Glu Met Lys Asp Leu Gly Pro Ala Asn Lys
                1010                1015                1020
```

Ile Leu Gly Met Gln Ile His Arg Asp Arg Asn Asn Met Lys Ile Trp
1025                1030                1035                1040

Leu Ser Gln Lys Asn Tyr Leu Lys Ile Leu Arg Arg Phe Asn Met
            1045                1050                1055

Gln Asp Cys Lys Ser Ile Ser Thr Ser Leu Pro Val Asn Phe Lys Leu
        1060                1065                1070

Ser Ser Ser Met Cys Pro Ser Asn Glu Ala Glu Arg Lys Glu Met Ser
    1075                1080                1085

Arg Val Pro Tyr Ala Ser Ala Val Gly Ser Leu Met Phe Ala Met Ile
    1090                1095                1100

Cys Thr Arg Pro Asp Ile Ala Gln Ala Val Gly Val Val Ser Arg Tyr
1105                1110                1115                1120

Met Ala Asn Pro Gly Gly Glu His Trp Ile Ala Val Lys Arg Ile Leu
            1125                1130                1135

Arg Tyr Ile Arg Gly Thr Ser Asp Val Ala Leu Cys Tyr Gly Gly Ser
            1140                1145                1150

Glu Phe Thr Val Arg Gly Tyr Val Asp Ser Asp Phe Ala Gly Asp Leu
    1155                1160                1165

Asp Lys Arg Lys Ser Thr Thr Gly Tyr Val Phe Thr Leu Ala Gly Ala
    1170                1175                1180

Ala Val Ser Trp Val Ser Lys Leu Gln Thr Val Val Ala Leu Ser Thr
1185                1190                1195                1200

Thr Glu Ala Glu Tyr Met Ala Ala Thr Gln Ala Cys Lys Lys Ala Ile
            1205                1210                1215

Trp Ile Gln Arg Leu Leu Glu Glu Leu Gly His Lys Gln Gln Lys Ile
            1220                1225                1230

Leu Val Phe Cys Asp Ser Gln Ser Ala Leu His Ile Ala Arg Asn Pro
    1235                1240                1245

Ala Phe His Ser Arg Thr Lys His Ile Gly Val Gln Tyr His Phe Val
    1250                1255                1260

Arg Glu Val Val Glu Asp Gly Ser Val Asp Leu Gln Lys Ile His Thr
1265                1270                1275                1280

Lys Glu Asn Leu Ala Asp Val Leu Thr Lys Pro Ile Asn Thr Asp Lys
            1285                1290                1295

Phe Val Trp Ser Arg Ser Ser Cys Gly Leu Ala Glu Thr
            1300                1305

<210> SEQ ID NO 9
<211> LENGTH: 5454
<212> TYPE: DNA
<213> ORGANISM: Citrus sinensis cv. Jingxian

<400> SEQUENCE: 9
ttgaaagtca tggctggcgc cggccatcta gatggccggt gccaaccatt caacattcaa      60
cacggcccgc cattgttggt ggtgccgtgt tgaatgactc caataaaaaa aaaaaaaaaa     120
aagagccaaa attttggcta tataaagagg gcttcccacc ctcattttc attccaatct     180 tgagatccaa ttttgtagag agaattgaga gttgtgagaa gtgattcttg caagagcaaa     240
gaattttgtg tgcttagtga tttgagagtt tgggtgtatt ggggttttgg gtagtgagct     300
aaaatactac aatacttgta actccttttc actagtataa tatttctttc tgtcttcgcc     360
cgtggacgta ggctaaaagc cgaaccacgt aatttctggt gtcctctatt gtgcttgttc     420 tttatttat tttcaatttc attttagctg cggtcctgct tcacccacca atttcctaac     480

```
agtggtatca gagctattgg ttgtatttt  ggagtcagga attgttcacg tattcacgta    540
tacggtgtac ggcactattc aattatacgg catacgatac tattcacgta tacggagtac    600
ggcactattc acgtatacgg cgtacggcac tattcacgta tacggcgtac ggcactattc    660
acgtatacgg tgtacggtac tattcatgta tacggtacta ttcacgtgaa acggtggaag    720
cgatccaaga attttgcggt gcaaagcagg gaatagtggt gtgagtaaag caactgtgtg    780
attctgtaca tgtctaggaa agttctgtca caaaggcgat aagagcttaa ggagtctggg    840
ttttaagtgg gaccattgtg acccctccag tctttcctgg gaactttcct ggtgtgcatt    900
ctcacacata ctcacaacta ttcaaggtgg tacactaact tgtgtgcggt atttatcaac    960
aaaatggcgg caaagtatga aattgagaag tttaacggaa ataattttc  gttgtggaaa   1020 atgaagatga aagctgtatt gaggaaaaat aattgtttgg cagcaattgg agaaaggccc   1080
atggagataa ctgatgacaa gtggaacgag gtagacagca acgccatttc tgatctacac   1140
ttggcacttg cggatggagt attatccagt gtggcagaga aaaatacggc gaaggaaatt   1200
tgggatactc tcacaaaatt gtacgaggcc aagtcactac acaacaaaat cttcttgaag   1260
aggaaactct atactcttcg aatggcggaa tctacaatgg tgaccgacca catcaacacc   1320
ttgaagactt tattttcaca acttacaacg ttgggtcata atatagagga aaatgaacgt   1380
gcagagcttc tacttcaaag tctaccagat tcgtatgatc aactcatcat caacctgacg   1440
aacaacaatc cagtggacag tctagttttc gacgatgttg cagcctccgt actaaatgag   1500
gagagcaggc ggaaaaataa ggaaaataga caagcaagtt cgcagcaagc ggaggcgcta   1560
tcggtgacga gagggagatc aacgaacgt  ggccccagtg ggagtcaaaa tcatggtaga   1620
tcaaaatcta gaagtaagaa gaatgttaaa tgctacaatt gtggcaagaa agggcacgtc   1680
aaaaaggagt gttggagtaa tcagaagaga agagagggta aagaacctga gtcatcaaat   1740
gctcaggggt gtgtagcaag tacctcggat gatggcgaaa tactctacag cgaggcaaca   1800
attgtttcag aaggcagaaa acgactttct gatgtctggc ttatagactc aggagctacc   1860
tggcacatga cctctaggag agaatggttc cacacatatg aacctatctc aggaggatct   1920
gtatatatgg gtaacgatca tgccttggag atcgctggta ttggtactat caaaataaaa   1980
atgtttgatg gtacaattcg cacaattgag gaggtacgac atgtcaacgg cctaaagaaa   2040
aatctattgt ctttgggaca aatggatagt catgggtgca aaactcatgt ggagaatgga   2100
attatgaaga tcgttaaagg cgcgcttgta ttgatgaagg cagaaaagat ctgtgctaat   2160
ctattcatgc ttaaaggaga aacactacag gaggctgatg cgtgtgtcgc gtcaaatgga   2220
gaagaatcaa cgatgatgtg gcatctcaaa ctcggccaca tgtcagaaca aggcttgaag   2280
attctctctg agcgaaaatt gcctccgggg ctcaaatcgg taagtttacc attttgcgag   2340
cattgtgtta caagtaagca gcatagatta aaattcagta gatctattgc tagaagtaaa   2400
tgcattctcg acttgattca ttctgatgtt tgggaatcac cggatatatc catgggaggt   2460
gcaaagtaca tggtgacttt cattgatgat tattccagaa gatgttgggt gtatccaatt   2520
aagaaaaagt cagatgtatt tcctgtgttt aaagaataca agcgtgggt  ggaacttgaa   2580 tctggtaaaa agatcaagtg cttgaggaca gataatggtg gagaatatac agacagcgag   2640
tttcttgctt tctgtaagca agaaggtatt cagagacagt tcacggtggc atacactcct   2700
caacaaaatg gagtggcaga acggatgaac agaactctta cagaaagaat aagagctatg   2760
ttgaggactg ctggtctacc taattcattc tgggcagaag cagccaaaac tgcctgttat   2820
atagtaaatc gatcgccatc tacagctatt gggctgaaga cagcgatgga gatgtggact   2880
```

```
ggaaagccag ctgattattc ctacctacat gcatttggat gtcctgtgta cgtgatgtac   2940
aatgcccaag aaagaacaaa gctggatcca aaatctagaa aatgtatctt cttggggtat   3000
gctgatggag taaaggggta tcgtctgtgg gaccccactg cccataagat cgtcatcagc   3060
agagatgtta tctttgtaga agatcaactg caaagaaaag atggagatga tggcactgta   3120
aaagaaaagt ctgagactgt gccagtatat gtcgaaaata atccagaaaa ttcagattct   3180
tctgaagcag caccagagca cgaggaacaa gaaccagtcg agtccgaggc tccagaagtt   3240
cgtcggtcaa ctcgtgagag acgaccgcca acgtggcact cggaatatgt cacagagatc   3300
aacgttgcat actgtcttct aacagaggat ggagagcctt caactttcca tgaagcttta   3360
aacagcttag atgttgcttt gtggatgaca gcaatgcagg aagaaattga agctctacac   3420
aagaacaaga catgggaact tgtaccacta ccacacggaa gaaaagccat ggaaacaaa    3480 tgggtctaca agatcaaacg tgatggcaat gaccaagtgg agcggtatcg tgcgagactg   3540
gtagtgaaag atatgctca gaaagaaggt attgacttca cgagatatt ttctccggtg     3600 gttcgactca caacagtcag aatagttttg gcaatgtgtg ccacatttga cctacatcta   3660
gagcagttag atgtgaaaac tgcatttctt catggagaac ttgaagaaga aatatatatg   3720
ctccaaccag aaggttttgc agaaacagga aaggagaact tggtttgcag gttgaacaaa   3780
tctctatacg gtctcaaaca ggcgccgagg tgttggtata agagatttga ttccttcatt   3840
atgagccttg gatacaacag actcagttca gaccattgtg catattacaa gaggtttgaa   3900
gataatgatt tcatcatttt gctgttgtat gtggatgaca tgttggtagc aggtcccaac   3960
aaagatcgaa tccaagaatt gaaggcacag ttggctaggg agtttgaaat gaaggacttg   4020
ggaccagcaa acaagattct agggatgcaa attcaccgag acagaaataa caggaagatt   4080
tggctctcac agaagaatta tttgaagaaa atcttgcggc gcttcaacat gcaagattgt   4140
aagtcaattt ctaccccact tcctgttaat ttcaaattat cctcaagtat gtgtcctagc   4200
aatgaagcgg agaggaagga gatgtctcga gtaccgtatg catcagcagt gggaagtttg   4260
atgttcgcta tgatatgcac aagaccggac attgcacaag cagtgggagc agtcagtcga   4320
tacatggcga atcctggtgg agagcattgg atagctgtga agaggattct gagatacatc   4380
agaggaacct caaatgttgc attatgttat ggaggatcag agtttactgt cagaggctat   4440
gtggattcag attttgctgg agatcttgat aaaaggaaat ccactactgg ttatgtgttt   4500
acacttgcgg gagcagctgt aagctgggtt tctaaactgc agaccgttgt ggctttatct   4560
acaacagaag cagagtacat ggcagctaca caagcttgca aggaagctat ttggatacaa   4620
agattattgg aggagcttgg gcacaaacaa cagaaaattc ctgtgttttg tgacagtcag   4680
agtgccttgc acattgcaag gaatccagcc tttcattcca ggacaaagca cataggagtc   4740
cagtatcact tcgttcgtga agtagtggaa gatggaagtg tggatttaca gaaaatccat   4800
acgaaggaga acctagcaga tgttttgacc aagtcgataa atactgataa gtttgtctgg   4860
agtagatcct cctgtggcct agcagcaacg taggcaacat gactatggcg aagcagaaag   4920
gatggtgtgg agattgattg gtcctcaatc aaatctccaa gtgggagaat gttgaaagtc   4980
atggctggcg ccggccatct agatggccgg tgccaaccat tcaacattca acacggcccg   5040
ccattgttgg tggtgccgtg ttgaatgact ccaataaaaa aaaaaaaaa aaagagccaa   5100 aattttggct atataaagag gcttccacc cctcattttt cattccaatc ttgagatcca    5160
attttgtaga gagaattgag agttgtgaga agtgattctt gcaagagcaa agaattttgt   5220
```

```
gtgcttagtg attcgagagt ttgggtgtat tggggttttg ggtagtgagc taaaatacta      5280
caatacttgt aactcctttt cactagtata atatttcttt ctgtcttcgc ccgtggacgt      5340
aggctaaaag ccgaaccacg taatttctgg tgtcctctat tgtgcttgtt ctttatttta      5400
ttttcaattt cattttagct gcggtcctgc ttcacccacc aatttcctaa cagt            5454
```

<210> SEQ ID NO 10
<211> LENGTH: 1309
<212> TYPE: PRT
<213> ORGANISM: Citrus sinensis cv. Jingxian

<400> SEQUENCE: 10

```
Met Ala Ala Lys Tyr Glu Ile Glu Lys Phe Asn Gly Asn Asn Phe Ser
 1               5                  10                  15

Leu Trp Lys Met Lys Met Lys Ala Val Leu Arg Lys Asn Asn Cys Leu
            20                  25                  30

Ala Ala Ile Gly Glu Arg Pro Met Glu Ile Thr Asp Asp Lys Trp Asn
        35                  40                  45

Glu Val Asp Ser Asn Ala Ile Ser Asp Leu His Leu Ala Leu Ala Asp
    50                  55                  60

Gly Val Leu Ser Ser Val Ala Glu Lys Asn Thr Ala Lys Glu Ile Trp
65                  70                  75                  80

Asp Thr Leu Thr Lys Leu Tyr Glu Ala Lys Ser Leu His Asn Lys Ile
                85                  90                  95

Phe Leu Lys Arg Lys Leu Tyr Thr Leu Arg Met Ala Glu Ser Thr Met
            100                 105                 110

Val Thr Asp His Ile Asn Thr Leu Lys Thr Leu Phe Ser Gln Leu Thr
        115                 120                 125

Thr Leu Gly His Asn Ile Glu Glu Asn Glu Arg Ala Glu Leu Leu Leu
    130                 135                 140

Gln Ser Leu Pro Asp Ser Tyr Asp Gln Leu Ile Ile Asn Leu Thr Asn
145                 150                 155                 160

Asn Asn Pro Val Asp Ser Leu Val Phe Asp Asp Val Ala Ala Ser Val
                165                 170                 175

Leu Asn Glu Glu Ser Arg Arg Lys Asn Lys Glu Asn Arg Gln Ala Ser
            180                 185                 190

Ser Gln Gln Ala Glu Ala Leu Ser Val Thr Arg Gly Arg Ser Thr Glu
        195                 200                 205

Arg Gly Pro Ser Gly Ser Gln Asn His Gly Arg Ser Lys Ser Arg Ser
    210                 215                 220

Lys Lys Asn Val Lys Cys Tyr Asn Cys Gly Lys Lys Gly His Val Lys
225                 230                 235                 240

Lys Glu Cys Trp Ser Asn Gln Lys Arg Arg Glu Gly Lys Glu Pro Glu
                245                 250                 255

Ser Ser Asn Ala Gln Gly Cys Val Ala Ser Thr Ser Asp Asp Gly Glu
            260                 265                 270

Ile Leu Tyr Ser Glu Ala Thr Ile Val Ser Glu Gly Arg Lys Arg Leu
        275                 280                 285

Ser Asp Val Trp Leu Ile Asp Ser Gly Ala Thr Trp His Met Thr Ser
    290                 295                 300

Arg Arg Glu Trp Phe His Thr Tyr Glu Pro Ile Ser Gly Gly Ser Val
305                 310                 315                 320

Tyr Met Gly Asn Asp His Ala Leu Glu Ile Ala Gly Ile Gly Thr Ile
                325                 330                 335
```

-continued

```
Lys Ile Lys Met Phe Asp Gly Thr Ile Arg Thr Ile Glu Glu Val Arg
            340                 345                 350
His Val Asn Gly Leu Lys Lys Asn Leu Leu Ser Leu Gly Gln Met Asp
        355                 360                 365
Ser His Gly Cys Lys Thr His Val Glu Asn Gly Ile Met Lys Ile Val
    370                 375                 380
Lys Gly Ala Leu Val Leu Met Lys Ala Glu Lys Ile Cys Ala Asn Leu
385                 390                 395                 400
Phe Met Leu Lys Gly Glu Thr Leu Gln Glu Ala Asp Ala Cys Val Ala
                405                 410                 415
Ser Asn Gly Glu Glu Ser Thr Met Met Trp His Leu Lys Leu Gly His
            420                 425                 430
Met Ser Glu Gln Gly Leu Lys Ile Leu Ser Glu Arg Lys Leu Pro Pro
        435                 440                 445
Gly Leu Lys Ser Val Ser Leu Pro Phe Cys Glu His Cys Val Thr Ser
    450                 455                 460
Lys Gln His Arg Leu Lys Phe Ser Arg Ser Ile Ala Arg Ser Lys Cys
465                 470                 475                 480
Ile Leu Asp Leu Ile His Ser Asp Val Trp Glu Ser Pro Asp Ile Ser
                485                 490                 495
Met Gly Gly Ala Lys Tyr Met Val Thr Phe Ile Asp Asp Tyr Ser Arg
            500                 505                 510
Arg Cys Trp Val Tyr Pro Ile Lys Lys Ser Asp Val Phe Pro Val
        515                 520                 525
Phe Lys Glu Tyr Lys Ala Trp Val Glu Leu Glu Ser Gly Lys Lys Ile
    530                 535                 540
Lys Cys Leu Arg Thr Asp Asn Gly Gly Glu Tyr Thr Asp Ser Glu Phe
545                 550                 555                 560
Leu Ala Phe Cys Lys Gln Gly Ile Gln Arg Gln Phe Thr Val Ala
                565                 570                 575
Tyr Thr Pro Gln Gln Asn Gly Val Ala Glu Arg Met Asn Arg Thr Leu
            580                 585                 590
Thr Glu Arg Ile Arg Ala Met Leu Arg Thr Ala Gly Leu Pro Asn Ser
        595                 600                 605
Phe Trp Ala Glu Ala Lys Thr Ala Cys Tyr Ile Val Asn Arg Ser
    610                 615                 620
Pro Ser Thr Ala Ile Gly Leu Lys Thr Ala Met Glu Met Trp Thr Gly
625                 630                 635                 640
Lys Pro Ala Asp Tyr Ser Tyr Leu His Ala Phe Gly Cys Pro Val Tyr
                645                 650                 655
Val Met Tyr Asn Ala Gln Glu Arg Thr Lys Leu Asp Pro Lys Ser Arg
            660                 665                 670
Lys Cys Ile Phe Leu Gly Tyr Ala Asp Gly Val Lys Gly Tyr Arg Leu
        675                 680                 685
Trp Asp Pro Thr Ala His Lys Ile Val Ile Ser Arg Asp Val Ile Phe
    690                 695                 700
Val Glu Asp Gln Leu Gln Arg Lys Asp Gly Asp Gly Thr Val Lys
705                 710                 715                 720
Glu Lys Ser Glu Thr Val Pro Val Tyr Val Glu Asn Asn Pro Glu Asn
                725                 730                 735
Ser Asp Ser Ser Glu Ala Ala Pro Glu His Glu Glu Gln Pro Val
            740                 745                 750
Glu Ser Glu Ala Pro Glu Val Arg Arg Ser Thr Arg Glu Arg Arg Pro
```

```
                755                 760                 765
Pro Thr Trp His Ser Glu Tyr Val Thr Glu Ile Asn Val Ala Tyr Cys
770                 775                 780

Leu Leu Thr Glu Asp Gly Glu Pro Ser Thr Phe His Glu Ala Leu Asn
785                 790                 795                 800

Ser Leu Asp Val Ala Leu Trp Met Thr Ala Met Gln Glu Glu Ile Glu
                805                 810                 815

Ala Leu His Lys Asn Lys Thr Trp Glu Leu Val Pro Leu Pro His Gly
            820                 825                 830

Arg Lys Ala Ile Gly Asn Lys Trp Val Tyr Lys Ile Lys Arg Asp Gly
        835                 840                 845

Asn Asp Gln Val Glu Arg Tyr Arg Ala Arg Leu Val Val Lys Gly Tyr
    850                 855                 860

Ala Gln Lys Glu Gly Ile Asp Phe Asn Glu Ile Phe Ser Pro Val Val
865                 870                 875                 880

Arg Leu Thr Thr Val Arg Ile Val Leu Ala Met Cys Ala Thr Phe Asp
                885                 890                 895

Leu His Leu Glu Gln Leu Asp Val Lys Thr Ala Phe Leu His Gly Glu
            900                 905                 910

Leu Glu Glu Glu Ile Tyr Met Leu Gln Pro Glu Gly Phe Ala Glu Thr
        915                 920                 925

Gly Lys Glu Asn Leu Val Cys Arg Leu Asn Lys Ser Leu Tyr Gly Leu
    930                 935                 940

Lys Gln Ala Pro Arg Cys Trp Tyr Lys Arg Phe Asp Ser Phe Ile Met
945                 950                 955                 960

Ser Leu Gly Tyr Asn Arg Leu Ser Ser Asp His Cys Ala Tyr Tyr Lys
                965                 970                 975

Arg Phe Glu Asp Asn Asp Phe Ile Ile Leu Leu Leu Tyr Val Asp Asp
            980                 985                 990

Met Leu Val Ala Gly Pro Asn Lys Asp Arg Ile Gln Glu Leu Lys Ala
        995                 1000                1005

Gln Leu Ala Arg Glu Phe Glu Met Lys Asp Leu Gly Pro Ala Asn Lys
    1010                1015                1020

Ile Leu Gly Met Gln Ile His Arg Asp Arg Asn Asn Arg Lys Ile Trp
1025                1030                1035                1040

Leu Ser Gln Lys Asn Tyr Leu Lys Lys Ile Leu Arg Arg Phe Asn Met
                1045                1050                1055

Gln Asp Cys Lys Ser Ile Ser Thr Pro Leu Pro Val Asn Phe Lys Leu
            1060                1065                1070

Ser Ser Ser Met Cys Pro Ser Asn Glu Ala Glu Arg Lys Glu Met Ser
        1075                1080                1085

Arg Val Pro Tyr Ala Ser Ala Val Gly Ser Leu Met Phe Ala Met Ile
    1090                1095                1100

Cys Thr Arg Pro Asp Ile Ala Gln Ala Val Gly Ala Val Ser Arg Tyr
1105                1110                1115                1120

Met Ala Asn Pro Gly Gly Glu His Trp Ile Ala Val Lys Arg Ile Leu
                1125                1130                1135

Arg Tyr Ile Arg Gly Thr Ser Asn Val Ala Leu Cys Tyr Gly Gly Ser
            1140                1145                1150

Glu Phe Thr Val Arg Gly Tyr Val Asp Ser Asp Phe Ala Gly Asp Leu
        1155                1160                1165

Asp Lys Arg Lys Ser Thr Thr Gly Tyr Val Phe Thr Leu Ala Gly Ala
    1170                1175                1180
```

```
Ala Val Ser Trp Val Ser Lys Leu Gln Thr Val Val Ala Leu Ser Thr
1185                1190                1195                1200

Thr Glu Ala Glu Tyr Met Ala Ala Thr Gln Ala Cys Lys Glu Ala Ile
            1205                1210                1215

Trp Ile Gln Arg Leu Leu Glu Glu Leu Gly His Lys Gln Lys Ile
        1220                1225                1230

Pro Val Phe Cys Asp Ser Gln Ser Ala Leu His Ile Ala Arg Asn Pro
        1235                1240                1245

Ala Phe His Ser Arg Thr Lys His Ile Gly Val Gln Tyr His Phe Val
    1250                1255                1260

Arg Glu Val Val Glu Asp Gly Ser Val Asp Leu Gln Lys Ile His Thr
1265                1270                1275                1280

Lys Glu Asn Leu Ala Asp Val Leu Thr Lys Ser Ile Asn Thr Asp Lys
            1285                1290                1295

Phe Val Trp Ser Arg Ser Ser Cys Gly Leu Ala Ala Thr
        1300                1305

<210> SEQ ID NO 11
<211> LENGTH: 1227
<212> TYPE: DNA
<213> ORGANISM: Citrus sinensis cv. Moro

<400> SEQUENCE: 11
gatccaattt tgtagagaga attgagagtt gtgagaagtg attcttgcaa gagcaaagaa      60
ttttgtgtgc ttagtgattt gagagtttgg gtgtattggg gttttgggta gtgagctaaa    120
atactacaat acttgtaact cctttcact agtataatat ttcttctgt cttcgcccgt      180
ggacgtaggc taaaagccga accacgtaat ttctgtagaa gtagtttcct tgtggatgca    240
agacaagcac gtcactctct ccgaaaaggc ttaattgatc gacgtagcat gaggtaagca    300
catatactac acatagggtc tttatggcgg attccttagg agttcgtaaa ggtgcatgga    360
caggagagga agatgatctt cttaggaaat gcattgagaa atatggggaa gcaaaatggc    420
atcaagttcc tctaagagca ggattgcatc gatgccggaa aagctgtaga ctgcggtggc    480
tgaactatct caacccgaat atcaaacgag gagaatttgc agcagatgaa gttgatttaa    540
ttttaaggct ccataagctg ctgggcaaca gatggtcact gattgtgggc aggcttccgg    600
gaagaacagc gaacgatgtg aagaatttt ggaacacgca cctgcgcaag aaagtggata    660
aatgctgcaa gaataataaa gagatgaaag caaaagctga aaggtggaa aagatcaata    720
tcataaaacc tcaacctcgg accttcgcta aaaactcaca atggttgaag gcaagggaa    780
tgacttcaaa taatttgcaa ttaggagatt acaatctcgg caaacaatcc accccgtctg    840
atcatcatca tcatcatcaa cagcagcagg agaatgaaac tgaatctgta tggtgggaaa    900
gcttttatt cggagatgaa ttggatcaac aaggaatttc aagctcattg agtcggccag    960
aagaggaatc tactacggca atatttttg ccgaaaagtc tccagtagtg acaaaggtga   1020
cagaaaatag agtcattgaa gcaggccaga gttgtccgac tgatgacttc gctttcgacg   1080
cggaactttg ggatcttctc aatgcaaagt aagaaaaaaa gaaaaattac ttcaacttgc   1140
tgtccttaaa tttactactt cgtaatctat cttttttcca agcaataaat atgcaattaa   1200
atcaagcaaa aaaaaaaaaa aaaaaaa                                       1227

<210> SEQ ID NO 12
<211> LENGTH: 262
<212> TYPE: PRT
```

<213> ORGANISM: Citrus sinensis cv. Moro

<400> SEQUENCE: 12

```
Met Ala Asp Ser Leu Gly Val Arg Lys Gly Ala Trp Thr Gly Glu Glu
 1               5                  10                  15
Asp Asp Leu Leu Arg Lys Cys Ile Glu Lys Tyr Gly Glu Ala Lys Trp
                20                  25                  30
His Gln Val Pro Leu Arg Ala Gly Leu His Arg Cys Arg Lys Ser Cys
            35                  40                  45
Arg Leu Arg Trp Leu Asn Tyr Leu Asn Pro Asn Ile Lys Arg Gly Glu
        50                  55                  60
Phe Ala Ala Asp Glu Val Asp Leu Ile Leu Arg Leu His Lys Leu Leu
65                  70                  75                  80
Gly Asn Arg Trp Ser Leu Ile Val Gly Arg Leu Pro Gly Arg Thr Ala
                85                  90                  95
Asn Asp Val Lys Asn Phe Trp Asn Thr His Leu Arg Lys Lys Val Asp
            100                 105                 110
Lys Cys Cys Lys Asn Asn Lys Glu Met Lys Ala Lys Ala Glu Lys Val
        115                 120                 125
Glu Lys Ile Asn Ile Ile Lys Pro Gln Pro Arg Thr Phe Ala Lys Asn
    130                 135                 140
Ser Gln Trp Leu Lys Gly Lys Gly Met Thr Ser Asn Asn Leu Gln Leu
145                 150                 155                 160
Gly Asp Tyr Asn Leu Gly Lys Gln Ser Thr Pro Ser Asp His His His
                165                 170                 175
His His Gln Gln Gln Glu Asn Glu Thr Glu Ser Val Trp Trp Glu
            180                 185                 190
Ser Phe Leu Phe Gly Asp Glu Leu Asp Gln Gln Gly Ile Ser Ser Ser
        195                 200                 205
Leu Ser Arg Pro Glu Glu Glu Ser Thr Thr Ala Asn Ile Phe Ala Glu
    210                 215                 220
Lys Ser Pro Val Val Thr Lys Val Thr Glu Asn Arg Val Ile Glu Ala
225                 230                 235                 240
Gly Gln Ser Cys Pro Thr Asp Asp Phe Ala Phe Asp Ala Glu Leu Trp
                245                 250                 255
Asp Leu Leu Asn Ala Lys
            260
```

<210> SEQ ID NO 13
<211> LENGTH: 918
<212> TYPE: DNA
<213> ORGANISM: Citrus sinensis cv. Jingxian

<400> SEQUENCE: 13

```
acgtattatt atacaagcag ctgttctgta ggctctttaa attttataaa aaaagagagt    60
tgagtaagtg taggtgctaa ttaaattttg atttttaggg taagcacata tactacacat   120
agggtcttta tggcggattc cttaggagtt cgtaaaggtg catggacagg agaggaagat   180
gatcttctta ggaaatgcat tgagaaatat ggggaagcaa atggcatca agttcctcta   240
agagcaggat tgcatcgatg ccggaaaagc tgtagactgc ggtggctgaa ctatctcaac   300
ccgaatatca aacgaggaga atttgcagca gatgaagttg atttaatttt aaggctccat   360
aagctgctgg gcaacagatg gtcactgatt gtgggcaggc ttccgggaag aacagcgaac   420
gatgtgaaga atttttggaa cacgcacctg cgcaagaaag tggataaatg ctgcaagaat   480
```

-continued

```
aataaagaga tgaaagcaaa agctgagaag gtggaaaaga tcaatatcat aaaacctcaa    540
cctcggacct tcgctaaaaa ctcacaatgg ttgaagggca agggaatgac ttcaaataat    600
ttgcaattag gagattacaa tctcggcaaa caatccaccc cgtctgatca tcatcatcat    660
catcaacagc agcaggagaa tgaaactgaa tctgtatggt gggaaagctt tttattcgga    720
gatgaattgg atcaacaagg aatttcaagc tcattgagtc ggccagaaga ggaatctact    780
acggcaaata ttttttgccga aaagtctcca gtagtgacaa aggtgacaga aaatagagtc    840
attgaagcag gccagagttg tccgactgat gacttcgctt tcgacgcgga actttgggat    900
cttctcaatg caaagtaa                                                  918
```

<210> SEQ ID NO 14
<211> LENGTH: 262
<212> TYPE: PRT
<213> ORGANISM: Citrus sinensis cv. Jingxian

<400> SEQUENCE: 14

```
Met Ala Asp Ser Leu Gly Val Arg Lys Gly Ala Trp Thr Gly Glu Glu
  1               5                  10                  15

Asp Asp Leu Leu Arg Lys Cys Ile Glu Lys Tyr Gly Glu Ala Lys Trp
             20                  25                  30

His Gln Val Pro Leu Arg Ala Gly Leu His Arg Cys Arg Lys Ser Cys
         35                  40                  45

Arg Leu Arg Trp Leu Asn Tyr Leu Asn Pro Asn Ile Lys Arg Gly Glu
     50                  55                  60

Phe Ala Ala Asp Glu Val Asp Leu Ile Leu Arg Leu His Lys Leu Leu
 65                  70                  75                  80

Gly Asn Arg Trp Ser Leu Ile Val Gly Arg Leu Pro Gly Arg Thr Ala
                 85                  90                  95

Asn Asp Val Lys Asn Phe Trp Asn Thr His Leu Arg Lys Lys Val Asp
            100                 105                 110

Lys Cys Cys Lys Asn Asn Lys Glu Met Lys Ala Lys Ala Glu Lys Val
        115                 120                 125

Glu Lys Ile Asn Ile Ile Lys Pro Gln Pro Arg Thr Phe Ala Lys Asn
    130                 135                 140

Ser Gln Trp Leu Lys Gly Lys Gly Met Thr Ser Asn Asn Leu Gln Leu
145                 150                 155                 160

Gly Asp Tyr Asn Leu Gly Lys Gln Ser Thr Pro Ser Asp His His His
                165                 170                 175

His His Gln Gln Gln Gln Glu Asn Glu Thr Glu Ser Val Trp Trp Glu
            180                 185                 190

Ser Phe Leu Phe Gly Asp Glu Leu Asp Gln Gln Gly Ile Ser Ser Ser
        195                 200                 205

Leu Ser Arg Pro Glu Glu Ser Thr Thr Ala Asn Ile Phe Ala Glu
    210                 215                 220

Lys Ser Pro Val Val Thr Lys Val Thr Glu Asn Arg Val Ile Glu Ala
225                 230                 235                 240

Gly Gln Ser Cys Pro Thr Asp Asp Phe Ala Phe Asp Ala Glu Leu Trp
                245                 250                 255

Asp Leu Leu Asn Ala Lys
            260
```

<210> SEQ ID NO 15
<211> LENGTH: 792
<212> TYPE: DNA

<213> ORGANISM: Citrus sinensis

<400> SEQUENCE: 15

| | |
|---|---|
| ggataggtga tagttgagaa ttgagaagta aaaagataaa ttcaaacaaa actaaagaaa | 60 |
| tagaaagaga tgagggttgt gacaattagt tggtgtgtat agaaaaaaaa tgaattttta | 120 |
| aatcatttca taaggtatgt ttagaaagcg gttctcactt ttcagtcaaa caggggtgcc | 180 |
| aatagttcag ctcaaatcca attcttttt gggctttgca aagctaagcc caaaaacctt | 240 |
| cacgagtggt gacctatact ccgattctgg gaatgcgaag attccatgtt tcctagtggt | 300 |
| taccactctt tggtccaatc aacattttgc acacaattaa gttatttttg acttctctaa | 360 |
| tacagtaata ttttgttgcg tttggtgact ctgtttaaaa ttaggttaat tcaatgccgt | 420 |
| acaattttga tgagagtt acaagaccgg ccagaacttt tcttaatatg acaaaacata | 480 |
| attcgcaaac gccatgtgag cctgccaata ataatatgga gtatatggtg cggtggcagc | 540 |
| agtagctgat atctttagtg cggattgacg atattggcgc tgcacgcaat aaaatattga | 600 |
| caattcaaag cacccatcgc tttatttact tagcagtgaa ttatggtctc ctctccactt | 660 |
| agaaaatgcg ccaaaaacaa gtaagagagc atcattttc tcttcttcct ctgagatccc | 720 |
| tctgtttctt ttatctcaat tattgactcc tctccacttt cttttgtctt tctcatttct | 780 |
| ctgcgctctg cc | 792 |

<210> SEQ ID NO 16
<211> LENGTH: 3788
<212> TYPE: DNA
<213> ORGANISM: Citrus sinensis

<400> SEQUENCE: 16

| | |
|---|---|
| gaattctcga tcaaattaat cgggtgaaaa ttagggtcag gtcaaattgc tatttctagt | 60 |
| agtgactgtt gtatcttcag caacggtaac aaggaattta tgggaatggc cgtcgatttg | 120 |
| gtaatggtac ttataagaat attgtcatag acagagaaca ctacatagat agttctatat | 180 |
| tacaactatc tatttctatt tgactataac cttcttttc ttattttctt ctcttctcgt | 240 |
| aagagtccct gtataatag ctaaaatcta aggagttgaa ctattagcac tcctctaatc | 300 |
| tcctcgcaaa actcctcttt atatttacac ttttatcttc gaataaaatt tcactaaaag | 360 |
| gagaagtaaa aattgaaatc atgattcatg ctaccattac ggccaacatt ttacacccca | 420 |
| cctacgcgtt gctttgacat caacataaaa caagaaaaaa atttagaat tgtttctcaa | 480 |
| aattaataat tatgccacta tttagtagta ttacacacac acacacacac acacacacac | 540 |
| atatacacag tagttttctg gtcagggatt ttaaaataca ggaaagttcg agaaagcttt | 600 |
| aaaccgcac ggctttaaag gcttacagtt ttaagccttt aaagccatgc agttttaaaa | 660 |
| ctttaccgca ctttcttgta ctctaaaatt tcggactgaa acatttatat atatatatat | 720 |
| atatatatat aaatcagtaa gccatttctc atgatggcaa agatctatca tcaacgtcta | 780 |
| atggaagtta tttcttctat tagaaggcat gtaccttaaa accggtaagt taaactcata | 840 |
| aaaagtttga gcaattgaca aattttaaca aaacagcaag taaagaaaaa tgagtaggga | 900 |
| gaaaaatgc aaagaaatta agataattga gataggtgat agttgagaat tgagaagtaa | 960 |
| aaagataaat acaaacaaaa ctaaagaaat ataagagat gagggtcgtg acaattagtt | 1020 |
| ggtgtgaata gaaaaaaaat gaattttaa atcatttcat aaggtatgtt tagaaagcgg | 1080 |
| ttctcacttt tcagtcatac aggggtgcca atagttcagc tcaaatccaa ttcttttg | 1140 |
| ggctttgcaa agctaagccc aaaaaccttc acgagtggtg tcctatactc cgattctggg | 1200 |

```
aatgcgaaga ttccatgttt cctagtggtt accactcttt ggtccaatca acattttgca   1260
cacaattaag ttattttta cttctctaat acagtaatat tttgttgtgt ttggtaactc    1320
tgtttaaaat taggtcaatt caatgccgta tgattttgag atgagagtta caagaccggc   1380
cagaactttt cttaatatga caaaacataa ttcgcaaacg ccatgtgaac ctgccaataa   1440
taatatggag tatatggtgc ggtggcagca gtagctgata tctttagtgc ggattgacga   1500
tattggcgct gcacgcaata aaatattgac aattcaaagc acccattgct ttatttactt   1560
agcagtgaat tatggtctcc cctccactta gaaaatgcgc caaaaacaag taagagagca   1620
tcatttttct cttcttcctc tgagattcct ctgtttcttt tatctcaatt attgactcct   1680
ctccactttc ttttgtcttt ctcatttctc tgcgctctgg catggcaact cttcttagcc   1740
cgttttctcc ttctccttta gctaaagttt cgcaaataat tgattcaaca tcatcacctt   1800
cattttccct atttccatta ggccgccaaa atgcatgttc aagaaaggcg gatcatcatc   1860
atcatcacag gatccggaca agcaagtttg gtaacttcct agagttgaca ccggagtcgg   1920
tacctgaatt cttagacttt gatctcccct ggtttcatcc gtccgatcgt attcgatatg   1980
acgtgatcat cattggcact ggaccagccg gcctccgtct agctgagcaa gtctcatcgc   2040
gtcatagtgt caaggtatgt tgtgttgatc cttcacctct ttctacgtgg cctaacaact   2100
atggagtttg ggttgatgag tttgaagaca taggacttgt agactgtttg gacaaaactt   2160
ggccgatgac ttgtgttttt attaatgatc acaagaccaa gtatctagac aggccctacg   2220
gtcgtgttag tagaaatatt ttgaagacaa agttattaga gaattgtgtt tcaaatggag   2280
ttaagtttca taaggctaaa gtttggcacg tgaatcatca ggagttcgag tcttcgattg   2340
tttgtgatga tgggaatgag attaaggcta gcttgattgt tgatgctagt ggctttgcta   2400
gtagttttgt tgagtatgat aagccaagaa accatggata ccaaattgct catgggattt   2460
tagctgaggt tgagagtcac ccttttgatt tagacaaaat ggttctcatg gattggagag   2520
attcccattt agggaatgag ccttacttgc gagctagcaa tttgaagctc ccaacttttc   2580
tctatgcaat gccatttgat tcaaatttgg tattttaga agaaacatct ttggttagta   2640
ggccagtttt gtcatataaa gaggttaaga gcagaatggc agcgaggtta aggcatatgg   2700
gaattagagt taaagagtg attgaagatg aaaaatgttt gattccaatg ggaggtcctc    2760
tgcctgtgat cccacaaagt gtgatggcta ttggcggcac gtctggttta atccatcctg   2820
caactgggta tatggtggct cggaccatgg ctctggcccc tgccttggct gatgcaatag   2880
ctgaatgcct tggctcaacc aggatgatca gaggcaggcc acttcatcag aaagtgtgga   2940 atggggttgtg gccaattgac agaagatgca ataggagtt ttattcattt ggtatggaga    3000
ctttgttgaa gctggatttg aaggggacta ggagattctt tgatgctttc tttgatttga   3060
atccttacta ctggcatggg tttctgtcct caaggttgtc tcttgcagag cttgctggcc   3120
taagcttgtc tctctttgga cacgcctcga attcttccag gttggatatt gttaccaagt   3180
gccctgttcc tctggttaaa atgatgggga atcttgccct tgaaaccatt tgaagattaa   3240
atgttcttga ataattagcg tctcttgcag tacacagtaa catgttatga atacaacgaa   3300
tttaaaaagt ggatgtcggt atcattggtg cacttgaaaa gatggataat agaaatgaaa   3360
agatccgatt atatggttga aaatgatggc tttatacatg ttattgtgtt tgtgtttcac   3420
tttataagtg aagaaagtgt ttctgacctt cgcttttatt tgtatcaaat ccaaatgtac   3480
aaaatgcagt gaacacccac ccaggggcga agccagaaat ttttcgaag tccaagtatt    3540
```

-continued

```
atcgcagcta aaagtataaa acttaattaa gaagctcatt aatatataag aaaataaatc    3600
aaatctcaaa agtaattcaa ttacaattaa aaacgattta agttgtgctt tacgatactt    3660
ttgagtatta aatttatcta ttatcaaatt tgaatcgata gtatgtacaa ttctctttca    3720
ttataaataa tcatacaatc tgatataaac tcattctcta tcttatttcg aagtggtgtc    3780
ttgatatc                                                             3788
```

<210> SEQ ID NO 17
<211> LENGTH: 503
<212> TYPE: PRT
<213> ORGANISM: Citrus sinensis

<400> SEQUENCE: 17

```
Met Ala Thr Leu Leu Ser Pro Phe Ser Pro Ser Pro Leu Ala Lys Val
 1               5                  10                  15

Ser Gln Ile Ile Asp Ser Thr Ser Ser Pro Ser Phe Ser Leu Phe Pro
            20                  25                  30

Leu Gly Arg Gln Asn Ala Cys Ser Arg Lys Ala Asp His His His His
        35                  40                  45

His Arg Ile Arg Thr Ser Lys Phe Gly Asn Phe Leu Glu Leu Thr Pro
    50                  55                  60

Glu Ser Val Pro Glu Phe Leu Asp Phe Asp Leu Pro Trp Phe His Pro
65                  70                  75                  80

Ser Asp Arg Ile Arg Tyr Asp Val Ile Ile Gly Thr Gly Pro Ala
                85                  90                  95

Gly Leu Arg Leu Ala Glu Gln Val Ser Ser Arg His Ser Val Lys Val
            100                 105                 110

Cys Cys Val Asp Pro Ser Pro Leu Ser Thr Trp Pro Asn Asn Tyr Gly
        115                 120                 125

Val Trp Val Asp Glu Phe Glu Asp Ile Gly Leu Val Asp Cys Leu Asp
    130                 135                 140

Lys Thr Trp Pro Met Thr Cys Val Phe Ile Asn Asp His Lys Thr Lys
145                 150                 155                 160

Tyr Leu Asp Arg Pro Tyr Gly Arg Val Ser Arg Asn Ile Leu Lys Thr
                165                 170                 175

Lys Leu Leu Glu Asn Cys Val Ser Asn Gly Val Lys Phe His Lys Ala
            180                 185                 190

Lys Val Trp His Val Asn His Gln Glu Phe Glu Ser Ser Ile Val Cys
        195                 200                 205

Asp Asp Gly Asn Glu Ile Lys Ala Ser Leu Ile Val Asp Ala Ser Gly
    210                 215                 220

Phe Ala Ser Ser Phe Val Glu Tyr Asp Lys Pro Arg Asn His Gly Tyr
225                 230                 235                 240

Gln Ile Ala His Gly Ile Leu Ala Glu Val Glu Ser His Pro Phe Asp
                245                 250                 255

Leu Asp Lys Met Val Leu Met Asp Trp Arg Asp Ser His Leu Gly Asn
            260                 265                 270

Glu Pro Tyr Leu Arg Ala Ser Asn Leu Lys Leu Pro Thr Phe Leu Tyr
        275                 280                 285

Ala Met Pro Phe Asp Ser Asn Leu Val Phe Leu Glu Glu Thr Ser Leu
    290                 295                 300

Val Ser Arg Pro Val Leu Ser Tyr Lys Glu Val Lys Ser Arg Met Ala
305                 310                 315                 320

Ala Arg Leu Arg His Met Gly Ile Arg Val Lys Arg Val Ile Glu Asp
```

```
                        325                 330                 335
Glu Lys Cys Leu Ile Pro Met Gly Gly Pro Leu Pro Val Ile Pro Gln
                340                 345                 350

Ser Val Met Ala Ile Gly Gly Thr Ser Gly Leu Ile His Pro Ala Thr
            355                 360                 365

Gly Tyr Met Val Ala Arg Thr Met Ala Leu Ala Pro Ala Leu Ala Asp
        370                 375                 380

Ala Ile Ala Glu Cys Leu Gly Ser Thr Arg Met Ile Arg Gly Arg Pro
385                 390                 395                 400

Leu His Gln Lys Val Trp Asn Gly Leu Trp Pro Ile Asp Arg Arg Cys
                405                 410                 415

Asn Arg Glu Phe Tyr Ser Phe Gly Met Glu Thr Leu Leu Lys Leu Asp
            420                 425                 430

Leu Lys Gly Thr Arg Arg Phe Phe Asp Ala Phe Asp Leu Asn Pro
        435                 440                 445

Tyr Tyr Trp His Gly Phe Leu Ser Ser Arg Leu Ser Leu Ala Glu Leu
        450                 455                 460

Ala Gly Leu Ser Leu Ser Leu Phe Gly His Ala Ser Asn Ser Ser Arg
465                 470                 475                 480

Leu Asp Ile Val Thr Lys Cys Pro Val Pro Leu Val Lys Met Met Gly
                485                 490                 495

Asn Leu Ala Leu Glu Thr Ile
            500

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
ggrktkagra arggtdcatg gac                                          23

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19 ccarwatty ttsacatcrt twgc                                          24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
ttcccggaag cctgcccaca atca                                         24

<210> SEQ ID NO 21
<211> LENGTH: 25
<212> TYPE: DNA
<213> ORGANISM: Artificial Sequence
<220> FEATURE:
<223> OTHER INFORMATION: Primer
```

<400> SEQUENCE: 21
catggacagg agaggaagat gatct                                        25

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
cttactttgc attgagaaga tccca                                        25

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ttcccggaag cctgcccaca atca                                         24

<210> SEQ ID NO 24
<211> LENGTH: 26
<212> TYPE: DNA
<213> ORGANISM: Artificial Sequence
<220> FEATURE:
<223> OTHER INFORMATION: Primer

<400> SEQUENCE: 24
caacttcatc tgctgcaaat tctcct                                       26

<210> SEQ ID NO 25
<211> LENGTH: 50
<212> TYPE: DNA
<213> ORGANISM: Artificial Sequence
<220> FEATURE:
<223> OTHER INFORMATION: Primer

<400> SEQUENCE: 25
ggggacaagt ttgtacaaaa aagcaggcta tggcggattc cttaggagtt             50

<210> SEQ ID NO 26
<211> LENGTH: 50
<212> TYPE: DNA
<213> ORGANISM: Artificial Sequence
<220> FEATURE:
<223> OTHER INFORMATION: Primer

<400> SEQUENCE: 26
gggaccactt tgtacaagaa agctgggtct tactttgcat tgagaagatc             50

<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
cctctcctgt ccatgcacct ttacgaac                                     28

<210> SEQ ID NO 28
<211> LENGTH: 29

```
<212> TYPE: DNA
<213> ORGANISM: Artificial Sequence
<220> FEATURE:
<223> OTHER INFORMATION: Primer

<400> SEQUENCE: 28
gaggaacttg atgccatttt gcttcccca                                              29

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
cattgaagca ggccagagtt gtccgactga tgac                                        34

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
ctctcctgtc catgcacctt tacgaactcc taag                                        34

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
gagagtatac cgtatgcgta caca                                                   24

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
acacgtagct attggaccac cct                                                    23

<210> SEQ ID NO 33
<211> LENGTH: 34
<212> TYPE: DNA
<213> ORGANISM: Artificial Sequence
<220> FEATURE:
<223> OTHER INFORMATION: Primer

<400> SEQUENCE: 33
gccgaaaagt ctccagtagt gacaaaggtg acag                                        34

<210> SEQ ID NO 34
<211> LENGTH: 34
<212> TYPE: DNA
<213> ORGANISM: Artificial Sequence
<220> FEATURE:
<223> OTHER INFORMATION: Primer

<400> SEQUENCE: 34
```
tcgctgttct tcccggaagc ctgcccacaa tcag        34

<210> SEQ ID NO 35
<211> LENGTH: 26
<212> TYPE: DNA
<213> ORGANISM: Artificial Sequence
<220> FEATURE:
<223> OTHER INFORMATION: Primer

<400> SEQUENCE: 35
ccgaaataca gaatgctcaa atggga        26

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
agcacctaca cttactcaac tctc        24

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
agctgctggg caacagatgg t        21

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
cttcacatcg ttcgctgttc        20

<210> SEQ ID NO 39
<211> LENGTH: 19
<212> TYPE: DNA
<213> ORGANISM: Artificial Sequence
<220> FEATURE:
<223> OTHER INFORMATION: Primer

<400> SEQUENCE: 39
gcccgtggac gtaggctaa        19

<210> SEQ ID NO 40
<211> LENGTH: 26
<212> TYPE: DNA
<213> ORGANISM: Artificial Sequence
<220> FEATURE:
<223> OTHER INFORMATION: Primer

<400> SEQUENCE: 40
aagaacaagc acaaaagaaa atacca        26

<210> SEQ ID NO 41
<211> LENGTH: 21
<212> TYPE: DNA
<213> ORGANISM: Artificial Sequence

```
<220> FEATURE:
<223> OTHER INFORMATION: Primer

<400> SEQUENCE: 41
tgacagtcag agtgccttgc a                                              21

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tcctatgtgc tttgtcctgg aa                                             22

<210> SEQ ID NO 43
<211> LENGTH: 255
<212> TYPE: PRT
<213> ORGANISM: Petunia x hybrida

<400> SEQUENCE: 43
```

Met Ser Thr Ser Asn Ala Ser Thr Ser Gly Val Arg Lys Gly Ala Trp
 1               5                  10                  15

Thr Glu Glu Glu Asp Leu Leu Arg Glu Cys Ile Asp Lys Tyr Gly
            20                  25                  30

Glu Gly Lys Trp His Leu Val Pro Val Arg Ala Gly Leu Asn Arg Cys
         35                  40                  45

Arg Lys Ser Cys Arg Leu Arg Trp Leu Asn Tyr Leu Arg Pro His Ile
 50                  55                  60

Lys Arg Gly Asp Phe Ser Leu Asp Glu Val Asp Leu Ile Leu Arg Leu
 65                  70                  75                  80

His Lys Leu Leu Gly Asn Arg Trp Ser Leu Ile Ala Gly Arg Leu Pro
                 85                  90                  95

Gly Arg Thr Ala Asn Asp Val Lys Asn Tyr Trp Asn Thr His Leu Arg
            100                 105                 110

Lys Lys Leu Ile Ala Pro His Asp Gln Lys Gln Glu Ser Lys Asn Lys
         115                 120                 125

Ala Val Lys Ile Thr Glu Asn Asn Ile Ile Lys Pro Arg Pro Arg Thr
130                 135                 140

Phe Ser Arg Pro Ala Met Asn Asn Phe Pro Cys Trp Asn Gly Lys Ser
145                 150                 155                 160

Cys Asn Lys Asn Thr Ile Asp Lys Asn Glu Gly Asp Thr Glu Ile Ile
                165                 170                 175

Lys Phe Ser Asp Glu Lys Gln Lys Pro Glu Glu Ser Ile Asp Asp Gly
            180                 185                 190

Leu Gln Trp Trp Ala Asn Leu Leu Ala Asn Asn Ile Glu Ile Glu Glu
         195                 200                 205

Leu Val Ser Cys Asn Ser Pro Thr Leu Leu His Glu Glu Thr Ala Pro
210                 215                 220

Ser Val Asn Ala Glu Ser Ser Leu Thr Gln Gly Gly Ser Gly Leu
225                 230                 235                 240

Ser Asp Phe Ser Val Asp Ile Asp Asp Ile Trp Asp Leu Val Ser
                245                 250                 255

```
<210> SEQ ID NO 44
<211> LENGTH: 274
<212> TYPE: PRT
```

<213> ORGANISM: Solanum lycopersicum

<400> SEQUENCE: 44

Met Asn Ser Thr Ser Met Ser Leu Gly Val Arg Lys Gly Ser Trp
1               5                   10                  15

Thr Asp Glu Glu Asp Phe Leu Leu Arg Lys Cys Ile Asp Lys Tyr Gly
            20                  25                  30

Glu Gly Lys Trp His Leu Val Pro Ile Arg Ala Gly Leu Asn Arg Cys
        35                  40                  45

Arg Lys Ser Cys Arg Leu Arg Trp Leu Asn Tyr Leu Arg Pro His Ile
    50                  55                  60

Lys Arg Gly Asp Phe Glu Gln Asp Glu Val Asp Leu Ile Leu Arg Leu
65                  70                  75                  80

His Lys Leu Leu Gly Asn Arg Trp Ser Leu Ile Ala Gly Arg Leu Pro
                85                  90                  95

Gly Arg Thr Ala Asn Asp Val Lys Asn Tyr Trp Asn Thr Asn Leu Leu
            100                 105                 110

Arg Lys Leu Asn Thr Thr Lys Ile Val Pro Arg Glu Lys Ile Asn Asn
        115                 120                 125

Lys Cys Gly Glu Ile Ser Thr Lys Ile Glu Ile Lys Pro Gln Arg
    130                 135                 140

Arg Lys Tyr Phe Ser Ser Thr Met Lys Asn Val Thr Asn Asn Val
145                 150                 155                 160

Ile Leu Asp Glu Glu Glu His Cys Lys Glu Ile Ile Ser Glu Lys Gln
                165                 170                 175

Thr Pro Asp Ala Ser Met Asp Asn Val Asp Pro Trp Trp Ile Asn Leu
            180                 185                 190

Leu Glu Asn Cys Asn Asp Asp Ile Glu Glu Asp Glu Glu Val Val Ile
        195                 200                 205

Asn Tyr Glu Lys Thr Leu Thr Ser Leu Leu His Glu Glu Ile Ser Pro
    210                 215                 220

Pro Leu Asn Ile Gly Glu Gly Asn Ser Met Gln Gln Gly Gln Ile Ser
225                 230                 235                 240

His Glu Asn Trp Gly Glu Phe Ser Leu Asn Leu Pro Pro Met Gln Gln
                245                 250                 255

Gly Val Gln Asn Asp Asp Phe Ser Ala Glu Ile Asp Leu Trp Asn Leu
            260                 265                 270

Leu Asp

<210> SEQ ID NO 45
<211> LENGTH: 307
<212> TYPE: PRT
<213> ORGANISM: Vitis vinifera

<400> SEQUENCE: 45

Met Glu Ser Leu Gly Val Arg Lys Gly Ala Trp Ile Gln Glu Glu Asp
1               5                   10                  15

Val Leu Leu Arg Lys Cys Ile Glu Lys Tyr Gly Glu Gly Lys Trp His
            20                  25                  30

Leu Val Pro Leu Arg Ala Gly Leu Asn Arg Cys Arg Lys Ser Cys Arg
        35                  40                  45

Leu Arg Trp Leu Asn Tyr Leu Lys Pro Asp Ile Lys Arg Gly Glu Phe
    50                  55                  60

Ala Leu Asp Glu Val Asp Leu Met Ile Arg Leu His Asn Leu Leu Gly
65                  70                  75                  80

```
Asn Arg Trp Ser Leu Ile Ala Gly Arg Leu Pro Gly Arg Thr Ala Asn
                85                  90                  95

Asp Val Lys Asn Tyr Trp His Gly His His Leu Lys Lys Lys Val Gln
            100                 105                 110

Phe Gln Glu Glu Gly Arg Asp Lys Pro Gln Thr His Ser Lys Thr Lys
        115                 120                 125

Ala Ile Lys Pro His Pro His Lys Phe Ser Lys Ala Leu Pro Lys Phe
    130                 135                 140

Glu Leu Lys Thr Thr Ala Val Asp Thr Phe Asp Thr Gln Val Ser Thr
145                 150                 155                 160

Ser Ser Lys Pro Ser Ser Thr Ser Pro Gln Pro Asn Asp Asp Ile Ile
                165                 170                 175

Cys Trp Glu Ser Leu Leu Ala Glu His Ala Gln Met Asp Gln Glu Thr
            180                 185                 190

Asp Phe Ser Ala Ser Gly Glu Met Leu Ile Ala Ser Leu Arg Thr Glu
        195                 200                 205

Glu Thr Ala Thr Gln Lys Lys Gly Pro Met Asp Gly Met Ile Glu Gln
    210                 215                 220

Ile Gln Gly Gly Glu Gly Asp Ile Ile Trp Trp Glu Ser Leu Leu Ala
225                 230                 235                 240

Glu His Ala Gln Met Asp Gln Glu Thr Asp Phe Ser Ala Ser Gly Glu
                245                 250                 255

Met Leu Ile Ala Ser Leu Arg Thr Glu Glu Thr Ala Thr Gln Lys Lys
            260                 265                 270

Gly Pro Met Asp Gly Met Ile Glu Gln Ile Gln Gly Gly Glu Gly Asp
        275                 280                 285

Phe Pro Phe Asp Val Gly Phe Trp Asp Thr Pro Asn Thr Gln Val Asn
    290                 295                 300

His Leu Ile
305

<210> SEQ ID NO 46
<211> LENGTH: 249
<212> TYPE: PRT
<213> ORGANISM: Ipomoea batatas

<400> SEQUENCE: 46

Met Val Ile Ser Ser Val Trp Leu Glu Ser Ser Arg Val Arg Lys
 1               5                  10                  15

Gly Ala Trp Ser Glu Glu Glu Asp Gln Leu Leu Arg Asp Cys Ile Gln
            20                  25                  30

Lys Tyr Gly Glu Gly Lys Trp His Leu Ile Pro Leu Arg Ala Gly Leu
        35                  40                  45

Asn Arg Cys Arg Lys Ser Cys Arg Leu Arg Trp Leu Asn Tyr Leu Arg
    50                  55                  60

Pro Asp Ile Lys Arg Gly His Phe Ser Val Asp Glu Val Asp Leu Ile
65                  70                  75                  80

Leu Arg Leu His Arg Leu Leu Gly Asn Arg Trp Ser Leu Ile Ala Gly
                85                  90                  95

Arg Ile Pro Gly Arg Thr Ala Asn Asp Val Lys Asn Phe Trp Asn Thr
            100                 105                 110

His Leu Gln Lys Lys Val Ser Ala Met Ala Ser Ser Arg Gln Asp Ser
        115                 120                 125

Tyr Trp Lys Gly Lys Ala Pro Glu Ile Thr Glu Asn Thr Val Val Arg
```

```
                130                 135                 140
Pro Arg Pro Arg Arg Phe Leu Lys Ala Ser Ser Ser Pro Thr Thr Leu
145                 150                 155                 160

Leu Thr Glu Asn Ala Thr Lys Val Val Gly Tyr Asp Gly Gln Leu Gln
                165                 170                 175

Gly His Met Thr Thr Gln Pro Glu Thr Thr Ser Asn Leu Leu Met Glu
            180                 185                 190

Asn Phe Gln Gln Lys Asn Leu Thr Thr Thr Leu Pro Ser Ala Leu Glu
        195                 200                 205

Thr Thr Pro His Asp Asn Val Lys Trp Trp Glu Asp Val Leu Ser Asp
    210                 215                 220

Lys Glu Leu Asn Asp Glu Gly Gln Ile Cys Trp Ser Glu Phe Ser Thr
225                 230                 235                 240

Asp Ile Asp Leu Ser Glu Leu Leu Ser
                245

<210> SEQ ID NO 47
<211> LENGTH: 248
<212> TYPE: PRT
<213> ORGANISM: Arabidopsis thaliana

<400> SEQUENCE: 47

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
                20                  25                  30

Trp His Gln Val Pro Val Arg Ala Gly Leu Asn Arg Cys Arg Lys Ser
            35                  40                  45

Cys Arg Leu Arg Trp Leu Asn Tyr Leu Lys Pro Asn Ile Lys Arg Gly
50                  55                  60

Lys Leu Ser Ser Asp Glu Val Asp Leu Leu Arg Leu His Arg Leu Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Thr Asn Val Tyr Lys Pro Arg Pro Arg
    130                 135                 140

Ser Phe Ser Gly Asn Asn Asp Cys Asn His Leu Asn Ala Pro Pro Lys
145                 150                 155                 160

Val Asp Val Asn Pro Pro Cys Leu Gly Leu Asn Thr Asn Asn Val Cys
                165                 170                 175

Asp Asn Asn Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Met Leu Val Pro Glu Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

-continued

```
<210> SEQ ID NO 48
<211> LENGTH: 220
<212> TYPE: PRT
<213> ORGANISM: Antirrhinum majus

<400> SEQUENCE: 48

Met Glu Lys Asn Cys Arg Gly Val Arg Lys Gly Thr Trp Thr Lys Glu
1               5                   10                  15

Glu Asp Thr Leu Leu Arg Gln Cys Ile Glu Glu Tyr Gly Glu Gly Lys
            20                  25                  30

Trp His Gln Val Pro His Arg Ala Gly Leu Asn Arg Cys Arg Lys Ser
        35                  40                  45

Cys Arg Leu Arg Trp Leu Asn Tyr Leu Arg Pro Asn Ile Lys Arg Gly
    50                  55                  60

Arg Phe Ser Arg Asp Glu Val Asp Leu Ile Val Arg Leu His Lys Leu
65                  70                  75                  80

Leu Gly Asn Lys Trp Ser Leu Ile Ala Gly Arg Ile Pro Gly Arg Thr
                85                  90                  95

Ala Asn Asp Val Lys Asn Phe Trp Asn Thr His Val Gly Lys Asn Leu
            100                 105                 110

Gly Glu Asp Gly Glu Arg Cys Arg Lys Asn Val Met Asn Thr Lys Thr
        115                 120                 125

Ile Lys Leu Thr Asn Ile Val Arg Pro Arg Ala Arg Thr Phe Thr Gly
    130                 135                 140

Leu His Val Thr Trp Pro Arg Glu Val Gly Lys Thr Asp Glu Phe Ser
145                 150                 155                 160

Asn Val Arg Leu Thr Thr Asp Glu Ile Pro Asp Cys Glu Lys Gln Thr
                165                 170                 175

Gln Phe Tyr Asn Asp Val Ala Ser Pro Gln Asp Glu Val Glu Asp Cys
            180                 185                 190

Ile Gln Trp Trp Ser Lys Leu Leu Glu Thr Thr Glu Asp Gly Glu Leu
        195                 200                 205

Gly Asn Leu Phe Glu Glu Ala Gln Gln Ile Gly Asn
    210                 215                 220

<210> SEQ ID NO 49
<211> LENGTH: 20
<212> TYPE: PRT
<213> ORGANISM: Artificial Sequence
<220> FEATURE:
<223> OTHER INFORMATION: R2R3 Myb domain with a signature motif for
      interaction with bHLH proteins from the clade 3f
<220> FEATURE:
<221> NAME/KEY: UNSURE
<222> LOCATION: (3)...(4)
<223> OTHER INFORMATION: Xaa can be any amino acid
<220> FEATURE:
<221> NAME/KEY: UNSURE
<222> LOCATION: (6)...(8)
<223> OTHER INFORMATION: Xaa can be any amino acid
<220> FEATURE:
<221> NAME/KEY: UNSURE
<222> LOCATION: (10)...(15)
<223> OTHER INFORMATION: Xaa can be any amino acid
<220> FEATURE:
<221> NAME/KEY: UNSURE
<222> LOCATION: (17)...(19)
<223> OTHER INFORMATION: Xaa can be any amino acid

<400> SEQUENCE: 49

Asp Leu Xaa Xaa Arg Xaa Xaa Xaa Leu Xaa Xaa Xaa Xaa Xaa Xaa Leu
1               5                   10                  15
```

```
Xaa Xaa Xaa Arg
            20

<210> SEQ ID NO 50
<211> LENGTH: 7
<212> TYPE: PRT
<213> ORGANISM: Artificial Sequence
<220> FEATURE:
<223> OTHER INFORMATION: Conserved sequence motif of R2R3 Myb regulators
      of anthocyanin biosynthesis
<220> FEATURE:
<221> NAME/KEY: UNSURE
<222> LOCATION: (3)...(3)
<223> OTHER INFORMATION: Xaa can be any amino acid
<220> FEATURE:
<221> NAME/KEY: UNSURE
<222> LOCATION: (6)...(6)
<223> OTHER INFORMATION: Xaa can be Ser or Thr

<400> SEQUENCE: 50

Lys Pro Xaa Pro Arg Xaa Phe
 1               5
```